US008328876B2

(12) United States Patent
Behnam et al.

(10) Patent No.: US 8,328,876 B2
(45) Date of Patent: Dec. 11, 2012

(54) BONE MATRIX COMPOSITIONS AND METHODS

(75) Inventors: Keyvan Behnam, Redbank, NJ (US); Christopher Cioffi, North Brunswick, NJ (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1140 days.

(21) Appl. No.: 10/584,981

(22) PCT Filed: Dec. 31, 2004

(86) PCT No.: PCT/US2004/043999
§ 371 (c)(1),
(2), (4) Date: Jun. 29, 2006

(87) PCT Pub. No.: WO2005/065396
PCT Pub. Date: Jul. 21, 2005

(65) Prior Publication Data
US 2007/0154563 A1    Jul. 5, 2007

Related U.S. Application Data

(60) Provisional application No. 60/533,537, filed on Dec. 31, 2003.

(51) Int. Cl.
*A61K 38/01* (2006.01)
(52) U.S. Cl. ............... 623/23.63; 623/23.61; 623/16.11; 424/422; 424/423
(58) Field of Classification Search .................. None
See application file for complete search history.

(56) References Cited

U.S. PATENT DOCUMENTS

| | | | |
|---|---|---|---|
| 4,172,128 A | 10/1979 | Thiele et al. | |
| 4,294,753 A | 10/1981 | Urist | |
| 4,394,370 A | 7/1983 | Jefferies | |
| 4,430,760 A | 2/1984 | Smestad | |
| 4,440,370 A | 4/1984 | Rood | |
| 4,440,750 A | 4/1984 | Glowacki et al. | |
| 4,455,256 A | 6/1984 | Urist | |
| 4,472,840 A | 9/1984 | Jefferies | |
| 4,485,097 A | 11/1984 | Bell | |
| 4,563,350 A | 1/1986 | Nathan et al. | |
| 4,619,989 A | 10/1986 | Urist | |
| 4,657,548 A | 4/1987 | Nichols | |
| 4,678,470 A | 7/1987 | Nashef et al. | |
| 4,743,259 A | 5/1988 | Bolander et al. | |
| 4,755,184 A | 7/1988 | Silverberg | |
| 4,761,471 A | 8/1988 | Urist | |
| 4,774,228 A | 9/1988 | Seyedin et al. | |
| 4,774,322 A | 9/1988 | Seyedin et al. | |
| 4,787,906 A | 11/1988 | Haris | |
| 4,789,663 A | 12/1988 | Wallace | ........................ 514/21 |
| 4,789,732 A | 12/1988 | Urist | |
| 4,795,804 A | 1/1989 | Urist | |
| 4,804,744 A | 2/1989 | Sen | |
| 4,810,691 A | 3/1989 | Seyedin et al. | |
| 4,843,063 A | 6/1989 | Seyedin et al. | |
| 4,902,296 A | 2/1990 | Bolander et al. | |
| 5,041,138 A | 8/1991 | Vacanti et al. | |
| 5,073,373 A | 12/1991 | O'Leary | ....................... 424/422 |
| 5,106,748 A | 4/1992 | Wozney et al. | |
| 5,166,187 A | 11/1992 | Collombel et al. | |
| 5,211,664 A | 5/1993 | Tepic et al. | |
| 5,236,456 A * | 8/1993 | O'Leary et al. | ............... 424/422 |
| 5,266,683 A | 11/1993 | Oppermann et al. | |
| 5,270,300 A | 12/1993 | Hunziker | |
| 5,284,655 A | 2/1994 | Bogdansky et al. | |
| 5,290,558 A | 3/1994 | O'Leary et al. | |
| 5,290,763 A | 3/1994 | Poser et al. | |
| 5,314,476 A | 5/1994 | Prewett et al. | |
| 5,336,264 A | 8/1994 | Constanz et al. | |

(Continued)

FOREIGN PATENT DOCUMENTS

DE    2 253 086    10/1972

(Continued)

OTHER PUBLICATIONS

Landesman et al, "In Vivo Analysis of the Half-Life of the Osteoinductive Potential of Demineralized Bone Matrix Using Diffusion Chambers" Calcif Tissue Int (1989), vol. 45, No. 6, p. 348-353.*

(Continued)

*Primary Examiner* — Allison Ford

(57) ABSTRACT

The present invention provides methods of improving the osteogenic and/or chondrogenic activity of a bone matrix, e.g., a dermineralized bone matrix (DBM), by exposing the bone matrix to one or more treatments or conditions. In preferred embodiments the bone matrix is derived from human bone. The treatment or condition may alter the structure of the bone matrix and/or cleave one or more specific proteins. Cleavage may generate peptides or protein fragments that have osteoinductive, osteogenic, or chondrogenic activity. Preferred treatments include collagenase and various other proteases. The invention further provides improved bone and cartilage matrix compositions that have been prepared according to the inventive methods and methods of treatment using the compositions. The invention further provides methods of preparing, testing, and using the improved bone matrix compositions. Ona assay comprises exposing relatively undifferentiated mesenchymal cells to a bone matrix composition and measuring expression of a marker characteristic of osteoblast or chondrocyte lineage(s). Increased expression of the marker relative to the level of the marker in cells that have been exposed to a control matrix (e.g., an inactivated or untreated matrix) indicates that the treatment or condition increased the osteogenic and/or chondrogenic activity of the bone matrix. Suitable cells include C2C12 cells. A suitable marker is alkaline phosphatase. The inventive methods increase the osteogenic and/or chondrogenic activity of human DBM when tested using this assay system.

22 Claims, 8 Drawing Sheets

U.S. PATENT DOCUMENTS

| | | | |
|---|---|---|---|
| 5,354,557 A * | 10/1994 | Oppermann et al. | 424/423 |
| 5,378,469 A | 1/1995 | Kemp et al. | |
| 5,385,887 A | 1/1995 | Yim et al. | |
| 5,405,390 A | 4/1995 | O'Leary et al. | |
| 5,490,962 A | 2/1996 | Cima et al. | |
| 5,501,706 A | 3/1996 | Arenberg | |
| 5,507,813 A | 4/1996 | Dowd et al. | |
| 5,518,680 A | 5/1996 | Cima et al. | |
| 5,531,735 A | 7/1996 | Thompson | |
| 5,563,124 A | 10/1996 | Damien et al. | |
| 5,571,189 A | 11/1996 | Kuslich | |
| 5,607,269 A | 3/1997 | Dowd et al. | |
| 5,618,339 A | 4/1997 | Ito | |
| 5,658,882 A | 8/1997 | Celeste et al. | |
| 5,723,012 A | 3/1998 | Fages et al. | |
| 5,725,579 A | 3/1998 | Fages et al. | |
| 5,776,193 A | 7/1998 | Kwan et al. | |
| 5,788,959 A | 8/1998 | Singh | |
| 5,807,437 A | 9/1998 | Sachs et al. | |
| 5,830,493 A | 11/1998 | Yokota et al. | |
| 5,846,484 A | 12/1998 | Scarborough et al. | |
| 5,877,005 A | 3/1999 | Castor et al. | |
| 5,894,070 A | 4/1999 | Hansson et al. | |
| 5,899,939 A | 5/1999 | Boyce et al. | |
| 5,902,562 A | 5/1999 | Lagasse et al. | |
| 5,912,131 A | 6/1999 | Eyre | |
| 6,007,580 A | 12/1999 | Lehto et al. | |
| 6,018,095 A | 1/2000 | Lerch et al. | |
| 6,030,635 A | 2/2000 | Gertzman et al. | |
| 6,117,646 A | 9/2000 | Qvist | 435/7.93 |
| 6,120,558 A | 9/2000 | Poddevin et al. | |
| 6,124,273 A | 9/2000 | Drohan et al. | |
| 6,143,030 A | 11/2000 | Schroder | |
| 6,149,864 A | 11/2000 | Dillow et al. | |
| 6,162,258 A | 12/2000 | Scarborough et al. | |
| 6,180,606 B1 | 1/2001 | Chen et al. | |
| 6,197,325 B1 | 3/2001 | MacPhee et al. | |
| 6,217,614 B1 | 4/2001 | Fages et al. | |
| 6,245,537 B1 | 6/2001 | Williams et al. | |
| 6,294,041 B1 | 9/2001 | Boyce et al. | |
| 6,294,187 B1 | 9/2001 | Boyce et al. | |
| 6,311,690 B1 | 11/2001 | Jefferies | |
| 6,326,018 B1 | 12/2001 | Gertzman et al. | |
| 6,352,667 B1 | 3/2002 | English | |
| 6,372,257 B1 | 4/2002 | Marchosky | |
| 6,387,391 B1 | 5/2002 | Shikinami et al. | |
| 6,436,138 B1 | 8/2002 | Dowd et al. | |
| 6,440,444 B2 | 8/2002 | Boyce et al. | |
| 6,465,168 B1 | 10/2002 | Castor et al. | |
| 6,468,543 B1 | 10/2002 | Gilbertson et al. | |
| 6,478,825 B1 | 11/2002 | Winterbottom et al. | |
| 6,592,886 B1 | 7/2003 | Zimmermann | |
| 6,595,998 B2 | 7/2003 | Johnson et al. | |
| 6,599,515 B1 | 7/2003 | Delmotte | |
| 6,616,698 B2 | 9/2003 | Scarborough | |
| 6,618,698 B1 | 9/2003 | Beausoleil et al. | |
| 6,623,749 B2 | 9/2003 | Williams et al. | |
| 6,648,919 B2 | 11/2003 | Ferree | |
| 6,696,073 B2 | 2/2004 | Boyce et al. | |
| RE38,522 E | 5/2004 | Gertzman et al. | |
| 6,740,093 B2 | 5/2004 | Hochschuler et al. | |
| 6,752,831 B2 | 6/2004 | Sybert et al. | |
| 6,783,546 B2 | 8/2004 | Zucherman | |
| 6,843,807 B1 | 1/2005 | Boyce et al. | |
| 6,884,428 B2 | 4/2005 | Binette et al. | |
| 6,884,778 B2 | 4/2005 | Jo et al. | |
| 6,911,212 B2 | 6/2005 | Gertzman et al. | |
| 6,953,594 B2 | 10/2005 | Lee et al. | |
| 6,969,404 B2 | 11/2005 | Ferree | |
| 6,989,029 B2 | 1/2006 | Bonutti | |
| 7,001,390 B2 | 2/2006 | Gebhardt et al. | |
| 7,008,591 B2 | 3/2006 | Kafesjian et al. | |
| 7,019,192 B2 | 3/2006 | Gertzman et al. | |
| 7,025,771 B2 | 4/2006 | Kuslich et al. | |
| 7,045,141 B2 | 5/2006 | Merboth et al. | |
| 7,060,287 B1 | 6/2006 | Hubbard et al. | |
| 7,108,832 B2 | 9/2006 | Christensen et al. | |
| 7,163,691 B2 | 1/2007 | Knaack et al. | |
| 7,179,299 B2 | 2/2007 | Edwards et al. | |
| 7,208,015 B2 | 4/2007 | Pointillart et al. | |
| 7,220,282 B2 | 5/2007 | Kuslich | |
| 7,226,481 B2 | 6/2007 | Kuslich | |
| 7,241,303 B2 | 7/2007 | Reiss et al. | |
| 7,261,720 B2 | 8/2007 | Stevens et al. | |
| 2001/0031254 A1 | 10/2001 | Bianchi et al. | |
| 2001/0043258 A1 | 11/2001 | Ohki | |
| 2002/0058947 A1 | 5/2002 | Hochschuler et al. | |
| 2002/0068974 A1 | 6/2002 | Kuslich et al. | |
| 2002/0077701 A1 | 6/2002 | Kuslich | |
| 2002/0133166 A1 | 9/2002 | McKay et al. | |
| 2002/0197297 A1 | 12/2002 | Risbud et al. | |
| 2003/0008328 A1 | 1/2003 | Wironen et al. | |
| 2003/0039676 A1 | 2/2003 | Boyce et al. | |
| 2003/0044445 A1 | 3/2003 | Kay et al. | |
| 2003/0065392 A1 | 4/2003 | Fan et al. | |
| 2003/0072677 A1 | 4/2003 | Kafesjian et al. | |
| 2003/0129178 A1 | 7/2003 | Wegman et al. | |
| 2003/0143258 A1 | 7/2003 | Knaack et al. | |
| 2003/0152548 A1 | 8/2003 | Mikos et al. | |
| 2003/0194708 A1 | 10/2003 | Binnerts et al. | |
| 2004/0023387 A1 | 2/2004 | Morris et al. | |
| 2004/0024457 A1 | 2/2004 | Boyce et al. | |
| 2004/0059364 A1 | 3/2004 | Gaskins et al. | |
| 2004/0072322 A1 | 4/2004 | Thorne | |
| 2004/0146543 A1 | 7/2004 | Shimp et al. | |
| 2004/0220615 A1 | 11/2004 | Lin | |
| 2004/0249464 A1 | 12/2004 | Bindseil et al. | |
| 2005/0008620 A1 | 1/2005 | Shimp et al. | |
| 2005/0008672 A1 | 1/2005 | Winterbottom et al. | |
| 2005/0020506 A1 | 1/2005 | Drapeau et al. | |
| 2005/0027033 A1 | 2/2005 | Knaack et al. | |
| 2005/0037978 A1 | 2/2005 | Damien | |
| 2005/0131417 A1 | 6/2005 | Ahern et al. | |
| 2005/0244450 A1 | 11/2005 | Reddi | |
| 2005/0244457 A1 | 11/2005 | Reddi | |
| 2005/0251267 A1 | 11/2005 | Winterbottom et al. | |
| 2005/0283255 A1 | 12/2005 | Geremakis et al. | |
| 2006/0216321 A1 | 9/2006 | Lyu et al. | |
| 2006/0216323 A1 | 9/2006 | Knaack et al. | |
| 2006/0287732 A1 | 12/2006 | Pezeshkian | |
| 2007/0073401 A1 | 3/2007 | Pointillart et al. | |
| 2007/0093896 A1 | 4/2007 | Malinin | |
| 2007/0098756 A1 | 5/2007 | Behnam | |
| 2007/0110820 A1 | 5/2007 | Behnam | |
| 2007/0118222 A1 | 5/2007 | Lang | |
| 2007/0125700 A1 | 6/2007 | Ding et al. | |
| 2007/0142916 A1 | 6/2007 | Olson et al. | |
| 2007/0154563 A1 | 7/2007 | Behnam et al. | |
| 2007/0162132 A1 | 7/2007 | Messerli | |
| 2007/0178158 A1 | 8/2007 | Knaack et al. | |
| 2007/0231788 A1 | 10/2007 | Behnam et al. | |
| 2008/0027546 A1 | 1/2008 | Semler et al. | |
| 2008/0069852 A1 | 3/2008 | Shimp et al. | |
| 2008/0091270 A1 | 4/2008 | Miller et al. | |
| 2008/0260794 A1 | 10/2008 | Lauritzen et al. | |
| 2009/0087471 A1 | 4/2009 | Shimp et al. | |
| 2009/0130173 A1 | 5/2009 | Behnam et al. | |
| 2009/0155378 A1 | 6/2009 | Behnam et al. | |
| 2009/0157087 A1 | 6/2009 | Wei et al. | |
| 2009/0192474 A1 | 7/2009 | Wei et al. | |
| 2009/0220605 A1 | 9/2009 | Wei et al. | |

FOREIGN PATENT DOCUMENTS

| | | |
|---|---|---|
| DE | 693 24 117 T2 | 6/1994 |
| EP | 0 082 621 | 6/1983 |
| EP | 0 212 474 | 3/1987 |
| EP | 0 309 241 | 3/1989 |
| EP | 0 148 155 | 4/1989 |
| EP | 0 332 826 A1 | 9/1989 |
| EP | 0 440 991 | 8/1991 |
| EP | 0 567 391 A | 10/1993 |
| EP | 0 603 920 A1 | 6/1994 |
| EP | 0 621 020 A1 | 10/1994 |
| EP | 0781564 A2 | 7/1997 |
| JP | 01/179689 | 7/1989 |
| WO | WO 88/00205 | 1/1988 |
| WO | WO 88/01517 | 3/1988 |

| | | |
|---|---|---|
| WO | WO 90/03733 | 4/1990 |
| WO | WO-94/21298 | 9/1994 |
| WO | WO 95/31948 | 11/1995 |
| WO | WO 96/39170 | 12/1996 |
| WO | WO 00/13615 | 3/2000 |
| WO | WO 00/45870 | 8/2000 |
| WO | WO 00/47736 | 8/2000 |
| WO | WO 01/28461 A2 | 4/2001 |
| WO | WO 01/70136 A2 | 9/2001 |
| WO | WO 01/79342 A2 | 10/2001 |
| WO | WO 02/069818 A2 | 9/2002 |
| WO | WO 03/025271 A1 | 3/2003 |
| WO | WO-03/030956 A3 | 4/2003 |
| WO | WO 2004/073563 A | 9/2004 |
| WO | WO 2005/065396 A2 | 7/2005 |
| WO | WO-2005/072656 A1 | 8/2005 |
| WO | WO 2005/081699 A2 | 9/2005 |
| WO | WO 2006/076712 | 7/2006 |
| WO | WO 2007/053850 | 5/2007 |
| WO | WO 2007/133451 | 11/2007 |

OTHER PUBLICATIONS

Robey et al, Calcif Tissue Int, 1985, vol. 37, p. 453-460.*
Canalis, et al., *Endocrine Reviews*, 24(2): 218-235, 2003.
Crowe et al., *J. Nutr.*, 130(8): Aug. 2006, 2000.
Cui, et al., *The EMBO Journal*, 17(16): 4735-4743, 1998.
Cui, et al., *Genes & Developmet*, 15: 2797-2802, 2001.
Driessens et al., *Universitat Politecnica de Catalunya*, Barcelona, Spain, 31: 855-77.
Dubois, et al., *American J. of Pathology*, 158(1): 305-316, 2001.
Edwards et al., *Clinical Orthopaedics & Rel. Res.*, 357: 219-228, 1998.
Glowacki et al., *Clinics in Plastic Surgery*, 12(2): 233-41, 1985.
Han et al., *J. Orthop. Res.*, 21(4):648-54, 2003.
Jain et al., *Biochem. et Biophys. Acta*, 860: 448-61, 1986.
Katz, *Scientific American*, 106-116, 1960.
Kawai and Urist, *Clin. Orthopaedics and Related Res.*, 233: 262-267, 1988.
Kubler, et al., *J. Craniomaxillofac. Surg.*, 19(7): 283-288, 1991.
Lee, et al., *Nature*, 424: 389, 2003.
Lotz, *Clin. Orthopaedics and Related Res.*, 391S: S108-S115, 2001.
Mulliken et al., *Calcif. Tissue Int.*, 33: 71-6, 1981.
Neigel et al., *Opthal. Plast. Reconstr. Surg.*, 12(2): 108-20, 1996.
Paralkar, et al., *PNAS*, 100(11): 6736-6740, 2003.
Ray et al., "Bone implants", *J. Bone & Joint Surgery*, 39-A(5):1119-28, 1957.
Russell et al., *Orthopaedics*, 22(5): 524-31, 1999.
Ueland et al., *J. Clin. Endocrinol.& Metab.*, 84(1): 123-7, 1999.
Urist, *Science*, 150: 893-99, 1965.
Urist et al., *J. Histochem. & Cytochem.*, 22(2): 88-103, 1974.
Urist et al., *J. Theor. Biol.*, 38: 155-67, 1973.
Van den Berg et al., *Clin. Orthopaedics and Related Res.*, 391S: S244-S250, 2001.
Whiteman et al., *J. Hand. Surg (British and European Volume)*, 18B: 487-90, 1993.
Whittaker, et al, *Celltransmissions*, 17(1): 3-14.
Xiaobo et al., *Clin. Orthop. & Rel. Res.*, 293: 360-5, 1993.
Zhang et al., *J. Periodontol.*, 68(11): 1076-84, 1997.
International Search Report for PCT/US05/003092, date of mailing on Jun. 23, 2005.
Written Opinion of International Searching Authority, PCT/ US05/003092, date of mailing on Jun. 23, 2005.
International Search Report, PCT/US2004/43999, date of mailing Jul. 25, 2005.
Written Opinion of International Searching Authority, PCT/US2004/43999, date of mailing Jul. 25, 2005.
Landesman, Richard et al., "In Vivo Analysis of the Half-Life of the Osteoinductive Potential of Demineralized Bone Matrix Using Diffusion Chambers", *Calcif. Tissue Int.*, vol. 45, No. 6 1989 , 348-353.
Laursen, Malene et al., "Optimal Handling of freshcancellous bone graft-Different peroperative storing techniques evaluated by in vitro osteobalst-like cell metabolism", *Acta Orthop Scand.*, vol. 74, No. 4 2003 , 491.

Ou, Wenbin et al. "Effects of Glycerol in the Refolding and Unfolding of Creatine Kinase," *Tsinghua Science and Technology*, 7(4): 352-367 (Aug. 2002).
Ou, Wenbin et al. "Molecular Mechanism for Osmolyte Protection of Creatine Kinase Against Guanidine Denaturation," *Eur. J. Biochem.*, 268: 5901-5911 (2001).
Aspenberg et al., "Monkey Bone Matrix Induces Bone Formation in the Athymic Rat, but Not in Adult Monkeys," *J. of Orthop. Res.* 9:20-25 (1991).
Aspenberg P. et al., "Bone morphogenetic protein induces bone in the squirrel monkey, but bone matrix does not", *Acta Orthop Scand.* 63(6): 619-22 (Dec. 1992).
Blumenthal et al. "The use of collagen membrane barriers in conjunction with combined demineralized bone-collagen gel implants in human infrabony defects," *J. Periodontal* 61(6): 319-327 (Jun. 1990).
Bolander et al.,"The Use of Demineralized Bone Matrix in the Repair of Segmental Defects", *The Journal of Bone and Joint Surgery*, 68-A (8): 1264-1273. 1986.
Bravo, D.A. et al., "Accurate and Efficient Cleavage of the Human Insulin Proreceptor by the Human Proprotein-Processing Protease Furin," *Journal Biol Chem.* 269: 25830-25873.
Cameron, A. et al., "Polyarginines are potent inhibitors," *J. Biol. Chem.* 275: 36741-36749 (2000).
Canalis et al., "Stimulation of DNA and Collagen Synthesis by Autologous Growth Factor in Cultured Fetal Rat Calvaria," *Science*, 210:1021-1023 (1980).
Caplanis et al., "Effect of allogenic freeze-dried demineralized bone matrix on guided tissue regeneration in dogs," *J. Periodontal*, 851-856 (Aug. 1998).
Constantino, et al. "Bone Healing and Bone Substitutes," *Facial Plastic Surgery* 18(1): pp. 14-26 (2002).
Deatherage et al., "Packaging and Delivery of Bone Induction Factors in a Collagenous Implant," *Collagen Rel. Res.* 7:225-231 (1987).
Elliott, J.C., "Structure and Chemistry of the Apatites and Other Calcium Orthophosphates", Elsevier Science B.V., Amsterdam (1994).
Enlow, Donald H., "Principles of Bone Remodeling: An Account of Post-natal Growth and remodeling Processes in Long Bones and the Mandible," Charles C. Thomas, Springfield, Ill., (1963).
Farley et al., "Human Skeletal Growth Factor: Characterization of the Mitogenic Effect on Bone Cells in Vitro," *Biochem*, 21:3508-3513 (1982).
Flemmig, et al. "Long-Term Maintenance of Alveolar Bone Gain After Implantation of Autolyzed, Antigen-Extracted, Allogenic Bone in Periodontal Intraosseous Defects," *J. Periodontal*, 69(1): 47-53 (Jan. 1998).
Fujishiro, et al. "Histological evaluation of an impacted bone graft substitute composed of a combination of mineralized and demineralized allograft in a sheep vertebral bone defect," *Journal of Biomedical Materials Research Part A*, 538-544 (Aug. 4, 2006).
Gamradt, et al. "Bone Graft for Revision Hip Arthroplasty", *Clin. Ortho. and Related Research*, 417: 183-194 (2003).
Gepstein et al. "Bridging Large Defects in Bone by Demineralized Bone Matrix in the Form of a Powder," *The Journal of Bone and Joint Surgery*, 69A(7): 984-991 (1987).
Glowacki, "Cellular Reactions to Bone-Derived Material," *Clin. Ortho. and Related Research*, 324: 47-54 (1996).
Han, C. et al. "Autolysed Antigen-Extracted Allogeneic Boen for Repair of Diaphyseal Boen Defects in Rabbits," *Yonsei Medical Journal*, 31(3): 251-257 (1990).
Hollinger, et al. "A comparison of four particulate bone derivatives," *Clin. Ortho. and Related Research*, 267: 255-263 (Jun. 1991).
Hunziker et al., "Repair of Partial Thickness Defects in Articulate Cartilage: Cell Recruitment From the Synovial Membrane", *Journal Bone Joint Surg.*, 78-A: 721-733 (1996).
Iwata et al. "Chemosterilized Autolyzed Antigen-Extracted Allogeneic (AAA) Bone Matrix Gelatin for Repair of Defects from Excision of Benign Bone Tumors," *Clin. Ortho and Related Research*, 154: 150-155 (1981).
Janovec, et al. "Autolyzed Antigen-Extracted Allogeneic Bone for Bridging Segmented Diaphyseal Bone Defects in Rabbits," *Clin. Ortho. and Related Research*, 229: 249-256 (Apr. 1988).

Jean et al., "Alpha 1-Antitrypsin Portland, a bioengineered serpin highly selective for furin: Application as an antipathogenic agent", *Proc. Natl. Acad. Sci.*, USA 95: 7293-7298 (1998).

Johnson et al. "Human Bone Mortphogenetic Protein Allografting for Reconstruction of Femoral Nonunion," *Clin. Ortho. and Related Research*, 371: 61-74 (2000).

Johnson et al. "Preliminary explorations of reconstructive surgery with implants of autolyzed antigen-extracted allogeneic (AAA) bone supercharged with bone morphogenetic protein (BMP)," *Bone Grafts, Derivatives and Substitutes*, published by Butterworth-Heinemann, Oxford, pp. 363-376 (1994).

Johnson et al. "Resistant Nonunions and Partial or Complete Segmental Defects of Long Bones," *Clin. Ortho. and Related Research*, 277: 229-237 (Apr. 1992).

Kaban et al., "Treatment of Jaw Defects with Demineralized Bone Implants", *Journal of Oral and Maxillofacial Surgery*, pp. 623-626 (Jun. 6, 1989).

Kasten et al., "Comparison of Human Bone Marrow Stromal Cells Seeded on Calcium-Deficient Hydroxyapatite, Betatricalcium Phosphate and Demineralized Bone Matrix", *Biomaterials*, 24(15):2593-603 (2003).

Krysan, D.J., et al., "Quantitative Characterization of Furin Specificity", *Journal Biol. Chem.* 274, pp. 23229-23234 (1999).

Kubler et al. "Osteoinductive, morphologic, and biomechanical properties of autolyzed, antigen-extracted, allogeneic human bone," *J. Oral Maxillofac Surg*, 51: 1346-1357 (1993).

Kubler et al. "Repair of human skull defects using osteoinductive bone alloimplants," *J. of Cranio Maxillofac. Surg.* 23: 337-346 (1995).

Lewandrowski et al., "Flexural Rigidity in Partially Demineralized Diaphyseal Bone Grafts", *Clin, Ortho. Rel. Res.*, 317: 254-262 (1995).

Lewandrowski et al. "Improved Osteoinduction of Cortical Bone Allografts: A Study of the Effects of Laser Perforation and Partial Demineralization" *J. Orthop. Res.* vol. 15(5): 748-756 (1997).

Lewandrowski et al. "Kinetics of cortical bone demineralization: Controlled demineralization—a new method for modifying cortical bone allografts", *Journal of Biomedical Materials Research*, vol. 31: 365-372 (1996).

Lewandrowski et al. "Mechanical Properties of Perforated and Partially Demineralized Bone Grafts," *Clin. Ortho. and Related Research*, 353: 238-246 (1998).

Lewandrowski et al., "An Electron Microscopic Study on the Process of Acid Demineralization of Cortical Bone," *Calcified Tissue Int.* 61:294-297 (1997).

Lieberman, et al. "Treatment of Osteonecrosis of the Femoral Head with Core Decompression and Human Bone Morphogenetic Protein," *Clin. Ortho. and Related Research*, 429: 139-145 (2004).

Mellonig, James. "Bone Allografts in Periodontal Therapy," *Clin. Ortho. and Related Research*, 324: 116-125 (1996).

Mellonig, "Decalcified freeze-dried bone allograft as an implant material in human periodontal defects," *The Int'l Journal of Periodontics and Restorative Dentistry*, pp. 41-45 (1984).

Miloslav et al., "Autolyzed antigen-extracted allogeneic bone for bridging segmented diaphyseal bone defects in rabbits," *Clinical Orthopaedics and Related Research*, 229: 249-256 (Apr. 1988).

Nade et al. "Decalcified Bone as a Substrate for Osteogenesis," *Bone Joint Surg.* 59(2): 189-1996 (1977).

Nogami et al., "Sustrata Prepared from Bone Matrix for Chondrogenesis in Tissue Culture", *The Journal of Cell Biology*, 62: 510-519 (1974).

Nogami et al., "Transmembrane Bone Matrix Gelatin—Induced Differentiation of Bone", *Calcif. Tiss. Res.*, 19: 153-163 (1975).

Oberg et al. "Bone formation after implantation of autolysed antigen extracted allogeneic bone in ovariectomized rabbits," *Int. J. Oral Maxillofac. Surg.* 32: 628-632 (2003).

Oberg et al. "Bone healing after implantation of hydroxyapatite granules and blocks (Interpore 200) combined with autolyzed antigen-extracted allogeneic bone and fibrin glue," *Int. J. Oral. Maxillofac. Surg.* 23: 110-114 (1994).

"Organic Reactions", John Wiley and Sons, New York, NY (1991), vol. 40, table of contents.

Ousterhout. "Clinical Experience in Cranial and Facial Reconstruction with Demineranzeds Boned," *Ann. Plast. Surg.* 15(5): 367-373 (1995).

Peel SA et al., "In search of the ideal bone morphogenetic protein delivery system: in vitro studies on demineralized bone matrix, purified, and recombinant bone morphogenetic protein", *J. Craniofac. Surg.*, 14(3): 284-91 (May 2003).

Reddi et al., "Biochemical Sequences in the Transformation of Normal Fibroblasts in Adolescent Rats," *Proc. Natl. Acad. Sci. USA*, 69(6): 1601-1605 (1972).

Ripamonti et al. "Bone induction in a composite allogeneic bone/alloplastic implant," *J. Oral Maxillofac. Surg.* 47: 963-969 (1989).

Ripamonti et al. "The induction of bone in osteogenic composites of bone matrix and porous hydroxyapatite replicas: Experimental study on the baboon," *Oral Maxillofac. Surg.* 9: 817-830 (1991).

Ripamonti. "Bone induction in nonhuman primates: an experimental study on the baboon," *Clin. Ortho. and Related Research*, 269: 284-294 (Aug. 1991).

Ripamonti. "Calvarial regeneration in primates with autolyzed antigen-extracted allogeneic bone," *Clin. Ortho. and Related Research*, 282: 293-303 (Sep. 1992).

Rodd, "Chemistry of Carbon Compounds", Elsevier Science Publishers, Amsterdam (1989), Supplement to the 2nd Edition, table of contents.

Ronningen et al. "Bone formation enhanced by induction," *Acta Orthop Scan* 56: 67-71 (1985).

Ronningen et al. "Osteogenesis promoted by bone matrix combined with marrow," *Acta Orthop Scand* 5Z: 15-18 (1986).

Rosenquist et al. "Effects of bone grafting on maxillary bone healing in the growing pig," *J. Oral Maxillofac. Surg.* 40: 566-569 (1982).

Rosenthal et al. "Demineralized bone implants for nonunion fractures, bone cysts, and fibrous lesions," *Clin. Ortho. and Related Research* 362: 61-69 (1999).

Sailer et al. "Application of purified bone morphogenetic protein (BMP) in cranio-maxillo-facial surgery," *Jour. of Cranio-Maxillo-Facial Surgery* 22: 2-11 (1994).

Sambrook, et al. Molecular Cloning: A Laboratory Manual, $3^{rd}$ ed., Cold Spring Harbor Laboratory Press, Cold Spring Harbor (2001), table of contents only.

Sampath and Reddi, "Homology of bone-inductive proteins from human, monkey, bovine, and rat extracellular matrix," *Proc. Nat. Acad. Sci.* 80:6591-6594 (1983).

Sampath et al., "Bovine osteogenic protein is composed of dimmers of OP-1 and BMP-2A, Two members of the transforming growth factor-beta superfamily," *J. Biol. Chem.*, 5:265(22): pp. 13198-205 (Aug. 1990).

Sampath et al., "Isolation of osteogenin, an extracellular matrix-associated, bone-inductive protein, by heparin affinity chromatography," *Proc. Natl. Acad. Sci.* 84(7): 7109-7113 (1987).

Schmid et al. "Osteoinduction in tibial defects in the dog," *Unfallchirurgie* 19: 1-8 (1993).

Schwarz et al., "Dog bone less osteogenetic than rat bone," *Acta. Orthop. Scan.* 60(6): 693-695 (1989).

Schwarz et al. "Decalcified and undecalcified cancellous bone block implants do not heal diaphyseal defects in dogs," *Arch. Orthop. Trauma Surg.* 111:47-50 (1991).

Serini et al., "Class 3 semaphorins control vascular morphogenesis by inhibiting integrin function," *Nature*, 424:391-397 (Jul. 2003).

Smith, Michael et al. "March's Advanced Organic Chemistry", $5^{th}$ edition, John Wiley and Sons, New York, NY (Mar. 2001).

Steadman et al., "Microfracture: Surgical Technique and Rehabilitation to Treat Chondral Defects", *Clin. Orthop.*, 391 S:362-369 (2001).

Steiner, D.F., "The proprotein convertases," *Curr. Opinion Chem. Biol.* 2: 31-39 (1998).

Temenoff et al., "Effect of poly(ethylene glycol) molecular weight on tensile and swelling properties of oligo(poly(ethylene glycol) fumarate) hydrogels for cartilage tissue engineering", *OPF Hydrogel Material Properties*, John Wiley & Sons, Inc., pp. 429-437 (2001).

Terashima et al., Chondrogenesis in Outgrowths of Muscle Tissue onto Modified Bone Matrix in Tissue Culture, *Clinical Orthopaedics and Related Research*, 127: 248-256 (Sep. 1977).

Todescan et al., "A Small Animal Model for Investigating Endosseous Dental Implants: Effect of Graft Materials on healing of Endoss, Porous-Surfaced Implants Placed in a Fresh Extraction Socket," *The Journal of Oral and Maxillofacial Implants*, 2(2): 217-223 (1987).

Toriumi et al. "Demineralized Bone," Arch Otolaryngol Head Neck Surg. 116: 676-680 (Jun. 1990).

Urist. "The Bone Induction Principle," *Clin. Ortho. Rel. Res.*, 55: 243-283 (1967).

Urist et al., "Bone morphogenesis in Implants of Insoluble Bone Gelatin," *Proc. Natl. Acad. Sci.*,, 70(12): 3511-5 (Dec. 1973).

Urist et al., "A Chemosterilized Antigen-Extracted Autodigested Alloimplant for Bone Banks," *Arch Surg.* vol. 110: 416-428 (Apr. 1975).

Urist et al., "Cartilage Tissue Differentiation from Mesenchymal Cells Derived from Mature Muscle in Tissue Culture", In Vitro, 14(8): 697-706 (1978).

Urist et al. "Intertransverse Process Fusion with the Aid of Chemosterilized Autolyzed Antigen-Extracted Allogeneic (AAA) Bone," *Clin. Ortho. and Related Research*, 154: 97-113 (1981).

Urist et al., "Human Bone Morphogenetic Protein (hBMP)," *Proc. Soc. Exp. Biol.* 173:194-199 (1983).

Urist et al., "Purification of bovine bone morphogenetic protein by hydroxyapatite chromatography," *Prop. Natl. Acad. Sci.* 81:371-375 (1984).

Van den Ouweland, A.M.W. et al., "Structural homology between the human *fur* gene product and the subtilisin-like protease encoded by yeast *KEX2*," *Nucl. Acid Res.* 18(3): 664 (1990).

Wang et al., "Purification and characterization of other distinct bone-inducing factors," *Proc. Nat. Acad. Sci.* 85:9484-9488 (1988).

Wang et al., "Recombinant human bone morphogenetic protein induces bone formation," *Proc. Nat. Acad. Sci.* 87:2220-2224 (1990).

White et al., "Effective terminal sterilization using supercritical carbon dioxide," *Journal of Biotechnology*, 123: 504-515 (2006).

Wise, D.L., "Encyclopedia Handbook of Biomaterials and Bioengineering Part B", Applications New York: Marcel Decker (1995). vol. 1. table of contents.

Young et al. "Morphological changes of autoclaved autogenic bone implantation and autoclaved autogenic bone supplemented with allogenic demineralized bone matrix in rat parietal bone," *Histol Histopathol.* 11: 361-369 (1996).

\* cited by examiner

| Overall Approach | More Specific Example |
|---|---|
| Bone, Cartilage, or Extract Thereof ----------> | Bone Matrix |
| + | + |
| Biological, Chemical Agent or Condition* --------> | Collagenase |
| Substrate(s) ------------------------------------------> | Collagen ----> Collagen fragments |

* 1) Biological agent (e.g., protease, lipase, etc.)

* 2) Chemical agent (e.g., CNBr, LiCl, etc.)

* 3) Condition (e.g., heat, radiation)

Figure 1A

Overall Approach                                     More Specific Example

Bone, Cartilage, or Extract Thereof   -------------->        Bone Matrix

+                                                +

Biological, Chemical Agent or Condition* ------------>    PPC (e.g., furin)

Substrate(s) ---------------------------------------------->   Propeptide ----> Mature peptide
                                                          (e.g., proBMP2)    (mature BMP2)

* 1) Site-specific (e.g., PPCs)

* 2) Amino acid-specific (e.g., trypsin, papain)

* 3) Semi-specific (e.g., pepsin)
    a) Exogenous protease, lipase, glycosidase
    b) Endogenous protease, lipase, glycosidase

Figure 1B

BONE MATRIX COMPOSITIONS AND METHODS

CROSS-REFERENCE TO RELATED APPLICATION

This application claims priority to, and the benefit of, U.S. Provisional Patent Application Ser. No. 60/533,537, filed Dec. 31, 2003, which is incorporated herein by reference.

BACKGROUND

The rapid and effective repair of bone and cartilage defects caused by injury, disease, wounds, surgery, etc., has long been a goal of orthopaedic surgery. Toward this end, a number of compositions and materials have been used or proposed for use in the repair of bone and cartilage defects. The biological, physical, and mechanical properties of the compositions and materials are among the major factors influencing their suitability and performance in various orthopaedic applications.

Autologous cancellous bone ("ACB") is considered the gold standard for bone grafts. ACB is osteoconductive, is non-immunogenic, and, by definition, has all of the appropriate structural and functional characteristics appropriate for the particular recipient. Unfortunately, ACB is only available in a limited number of circumstances. Some individuals lack ACB of appropriate dimensions and quality for transplantation. Moreover, donor site morbidity can pose serious problems for patients and their physicians.

Much effort has been invested in the identification or development of alternative bone graft materials. Demineralized bone matrix ("DBM") implants have been reported to be particularly useful (see, for example, U.S. Pat. Nos. 4,394,370; 4,440,750; 4,485,097; 4,678,470; and 4,743,259; Mulliken et al., *Calcif. Tissue Int.* 33:71, 1981; Neigel et al., *Opthal. Plast. Reconstr. Surg.* 12:108, 1996; Whiteman et al., *J. Hand. Surg.* 18B:487, 1993; Xiaobo et al., *Clin. Orthop.* 293:360, 1993; each of which is incorporated herein by reference). Demineralized bone matrix is typically derived from cadavers. The bone is removed aseptically and/or treated to kill any infectious agents. The bone is then particulated by milling or grinding and then the mineral component is extracted (e.g., by soaking the bone in an acidic solution). The remaining matrix is malleable and can be further processed and/or formed and shaped for implantation into a particular site in the recipient. Demineralized bone prepared in this manner contains a variety of components including proteins, glycoproteins, growth factors, and proteoglycans. Following implantation, the presence of DBM induces cellular recruitment to the site of implantation. The recruited cells may eventually differentiate into bone forming cells. Such recruitment of cells leads to an increase in the rate of wound healing and, therefore, to faster recovery for the patient.

Current methods of articular cartilage restoration include (1) stimulation of fibrocartilaginous repair; (2) osteochondral grafting; and (3) autologous chondrocyte implantation. The results achieved using fibrocartilagenous repair are difficult to assess and deteriorate over time. Osteochondral grafting requires harvesting of cartilage with a layer of subchondral bone and implanting it into the articular defect site. The graft is fixed to the host by healing onto the host bone. Osteochondral grafts have the mechanical properties of normal articular cartilage, but this technique risks donor site morbidity and disease transmission.

Autologous chondrocyte implantation introduces isolated chondrocytes into the defect site after a period of ex vivo processing (see, e.g., U.S. Pat. Nos. 5,041,138; 5,206,023; 5,786,217; and 6,080,194, incorporated herein by reference). The cells are contained in vivo by a patch of periosteum, which is sutured to the surrounding host cartilage. The cells attach to the defect walls and produce extracellular matrix in situ. Although being able to use autologous cells and expand the cells ex vivo are significant advantages of this technique, loss of cell adherence, phenotypic dedifferentiation, and extracellular matrix production are proven difficulties.

A variety of approaches have been explored in an attempt to recruit progenitor cells or chondrocytes into an osteochondral or chondral defect. For example, penetration of subchondral bone has been performed in order to access mesenchymal stem cells (MSCs) in the bone marrow, which have the potential to differentiate into cartilage and bone. (Steadman, et al., "Microfracture: Surgical Technique and Rehabilitation to Treat Chondral Defects", *Clin. Orthop.*, 391 S:362-369 (2001). In addition, some factors in the body are believed to aid in the repair of cartilage. For example, it has been observed that transforming growth factors beta (TGF-β) have the capacity to recruit progenitor cells into a chondral defect from the synovium or elsewhere when TGF-β is loaded in the defect (Hunziker, et al., "Repair of Partial-Thickness Defects in Articular Cartilage: Cell Recruitment From the Synovial Membrane", *J. Bone Joint Surg.*, 78-A:721-733 (1996)). However, the application of growth factors to bone and cartilage implants has not resulted in the increase in osteoinductive or chondrogenic activity, respectively, expected.

Each of U.S. Pat. Nos. 5,270,300 and 5,041,138 describes a method for treating defects or lesions in cartilage which provides a matrix, possibly composed of collagen, with pores, which are large enough to allow cell population and contain growth factors (e.g., TGF-β) or other factors (e.g. angiogenesis factors) appropriate for the type of tissue desired to be regenerated.

Overall, current bone and cartilage graft formulations have various drawbacks. First, while the structures of most bone or cartilage matrices are relatively stable, the active factors within the matrices are rapidly degraded. The biologic activity of the matrix implants may be significantly degraded within 6-24 hours after implantation, and in most instances matrices are believed to be fully inactivated by about 8 days. Therefore, the factors associated with the matrix are only available to recruit cells to the site of injury for a short time after implantation. For much of the healing process, which may take weeks to months, the implanted material may provide little or no assistance in recruiting cells.

SUMMARY OF THE INVENTION

The present invention provides improved bone and cartilage matrices and methods for their production. According to certain embodiments of the invention a bone matrix is exposed to a treatment or condition that increases at least one biological activity of the bone matrix. The biological activities that may be increased include, but are not limited to, osteoinductive activity, osteogenic activity, chondrogenic activity, wound healing activity, neurogenic activity, contraction-inducing activity, mitosis-inducing activity, differentiation-inducing activity, chemotactic activity, angiogenic or vasculogenic activity, exocytosis or endocytosis-inducing activity, etc.

In certain embodiments of the invention the matrix is exposed to a biological or chemical agent or to a combination of agents. The agent may be a cleavage agent, e.g., a protease such as collagenase(s), or a chemical agent such as cyanogen bromide. The matrix may be exposed to multiple treatments either together or sequentially.

While not wishing to be bound by any theory, the treatment may alter the primary, secondary, tertiary, and/or quaternary structure of a component of the bone matrix (e.g., collagen, a bone morphogenetic protein, etc.) so as to increase the biological activity of the matrix. An inventive treatment or condition may "open up" the structure of the matrix, e.g., so as to allow biologically active molecules to be more readily released from or diffuse within the matrix and/or to allow components such as nutrients or growth-stimulatory molecules to enter the matrix. In certain embodiments the treatment or condition cleaves proteins present in the matrix (e.g., proteins such as bone morphogenetic proteins), which may result in conversion of an inactive protein into an active form, and/or may generate an active molecule that is less susceptible to degradation than a longer molecule from which it is derived.

The treatment or condition may cleave an inhibitory factor that would otherwise inhibit a positively acting agent (by which is meant an agent that enhances a biological activity of the bone matrix). For example, a variety of proteins or protein fragments are known to inhibit the osteoinductive and/or osteogenic activity of certain bone morphogenetic proteins such as BMP-2. In certain embodiments of the invention the inhibitory effect of a protein or protein fragment is reduced by exposing a bone or cartilage matrix to a treatment or condition. The treatment or condition may cause the cleavage or degradation of the inhibitory agent. The treatment or condition may block the interaction of the inhibitory agent with its target (e.g., BMP-2) or may inhibit synthesis, secretion, post-translational modification, transport, etc., of the inhibitory agent. For example, the bone matrix may be exposed to antibody to an inhibitory agents or the antibody can be added to the bone matrix.

In certain embodiments of the invention the matrix contains peptides or protein fragments that increase the osteoinductive or chondrogenic properties of the matrix. The peptides or protein fragments may be exogenously added to the matrix. The invention also encompasses matrices comprising other agents, e.g., agents that improve the osteogenic and/or chondrogenic activity of the matrix by either transcriptional or post-transcriptional regulation of the synthesis of bone or cartilage enhancing or inhibiting factors by cells within the matrix.

In certain embodiments of the invention the treatment or condition increases the biological activity of the matrix in vitro. For example, in certain embodiments of the invention the treated bone matrix composition displays increased osteoinductive and/or osteogenic activity, measured using a tissue culture assay such as that described in Example 10, as compared with the osteoinductive and/or osteogenic activity of an otherwise identical untreated bone matrix composition. Osteoinductive and/or osteogenic activity may be assessed by determining the ability of an appropriate cell line or primary cells in culture to differentiate along an osteoblastic or chondroblastic pathway. For example, the cells may display increased production of a marker characteristic of osteoblasts and/or chondrocytes. One such marker is alkaline phosphatase. Appropriate cells include, but are not limited to, mesenchymal stem cell lines, mesenchymal cell lines, preosteoblastic, osteoblastic, or chondroblastic cell lines and primary cells, e.g., primary cells derived from mesenchymal tissue. Preferably the treatment or condition also increases the biological activity in vivo, i.e., after implantation into a subject at a site such as a bone defect.

The invention provides a method of preparing a bone matrix comprising the steps of: (i) providing a bone matrix; and (ii) exposing the bone matrix to a treatment or condition that increases at least one biological activity of the bone matrix. In certain embodiments of the invention the exposing step comprises contacting the bone matrix with at least one bioactive agent, e.g., a protease such as collagenase. In certain embodiments of the invention the treatment or condition cleaves at least one protein present in the bone matrix, e.g., to alter the structure of at least one component of the bone matrix and/or to generate osteoinductive peptides or protein fragments, wherein the treatment or condition causes an increase in a biological activity of the bone matrix contacted with the bioactive agent.

The invention further provides a method of increasing the osteoinductivity of a bone matrix, the method comprising the steps of: (i) providing a bone matrix; and (ii) exposing the bone matrix to a treatment or condition that generates active osteoinductive peptides or protein fragments, wherein the peptides or protein fragments cause an increase in osteoinductivity of the bone matrix contacted with the protease. The treatment may be with a chemical cleavage agent such as cyanogen bromide. The condition may be a pH or temperature. In various embodiments of the invention the bone matrix comprises mineralized bone matrix, partially demineralized bone matrix, demineralized bone matrix, deorganified bone matrix, anorganic bone matrix, or a mixture thereof. In various embodiments of the invention the peptides or protein fragments are derived from a growth factor.

The invention also provides a method of increasing at least one biological activity of a bone matrix comprising the step of contacting a bone matrix with at least one agent that selectively degrades an inhibitor of the biological activity, wherein the bone matrix has increased biological activity resulting in improved bone formation compared to a bone matrix not contacted with the agent. The biological activity is preferably osteoinductive, osteogenic, or chondrogenic activity. The agent may be a bioactive agent, a chemical agent, etc. Similar methods are provided for cartilage matrices.

In another aspect, the invention provides a bone matrix composition for implantation at a bone defect site which comprises a bone matrix exposed to a treatment or condition, wherein the treatment or condition increases at least one biological activity of the bone matrix. Preferably the treatments and conditions described herein result in bone matrices with improved bone formation upon implantation into a subject compared to a bone matrix not exposed to the treatment or condition. In certain embodiments the bone matrix is treated with at least one bioactive agent, e.g., a protease such as collagenase. In certain embodiments of the invention the treatment causes cleavage of inactive proteins to generate osteoinductive peptides or protein fragments, wherein the osteoinductivity of the treated matrix compared to an untreated matrix is increased resulting in improved bone formation. In any of the various embodiments of the invention the bone matrix may comprise mineralized bone matrix, partially demineralized bone matrix, demineralized bone matrix, deorganified bone matrix, anorganic bone matrix, or a mixture thereof. In various embodiments of the invention the peptides or protein fragments are derived from a growth factor.

In another aspect, the invention provides an implantable bone growth inducing composition comprising: (i) a bone matrix; and (ii) a peptide or protein fragment that is capable of enhancing the osteoinductivity of the bone matrix. The invention further features an implantable cartilage repair graft composition comprising: (i) a cartilage repair matrix; and (ii) at least one peptide or protein fragment that is capable of enhancing the chondrogenic activity of the cartilage repair. The bone matrix component of the inventive compositions may comprise mineralized bone matrix, partially demineralized bone matrix, demineralized bone matrix, deorganified bone matrix, anorganic bone matrix, or mixtures thereof. In certain embodiments of the invention the peptide or protein fragment is derived from a growth factor.

The invention further provides a method of preparing a bone matrix composition, the method comprising the steps of: (i) providing a bone matrix; and (ii) adsorbing into the bone matrix peptides or protein fragments that are capable of enhancing the osteoinductivity of the bone matrix. The invention also includes a method of preparing a cartilage repair matrix composition, the method comprising the steps of: (i) providing a cartilage repair matrix; and (ii) adsorbing into the matrix peptides or protein fragments that are capable of enhancing the chondrogenic activity of the cartilage repair matrix.

In certain embodiments of the invention a bone matrix composition comprises an agent that acts as a stabilizer or diffusion barrier, e.g., a polymer selected from the group consisting of starches, dextrans, cellulose, polyesters, polycarbonates, polyarylates, and PLGA.

The invention further provides a bone or cartilage matrix composition comprising:
(i) a bone or cartilage matrix; and (ii) a transcription modulator, wherein the transcription modulator modulates transcription of a bone or cartilage enhancing or inhibiting factor. The transcription modulator can be, for example, a small molecule, a transcription factor, an engineered transcription modulating protein, or a vector that provides a template for intracellular synthesis of a transcription factor or engineered transcription modulating protein. The invention also includes a method of increasing the osteoinductive, osteoconductive, or chondrogenic properties of a bone repair matrix or a cartilage repair matrix comprising the step of introducing a transcription modulator into the matrix, wherein the transcription modulator modulates transcription of a bone or cartilage enhancing or inhibiting factor.

The invention further provides methods of treating a bone or cartilage defect, or a disease or condition that results in deterioration of bone or cartilage, by implanting any of the various compositions of the invention into a subject.

This application refers to various patents, patent applications, journal articles, and other publications, all of which are incorporated herein by reference. In addition, the following standard reference works are incorporated herein by reference: *Current Protocols in Molecular Biology, Current Protocols in Immunology, Current Protocols in Protein Science,* and *Current Protocols in Cell Biology*, John Wiley & Sons, N.Y., edition as of July 2002; Sambrook, Russell, and Sambrook, *Molecular Cloning. A Laboratory Manual*, $3^{rd}$ ed., Cold Spring Harbor Laboratory Press, Cold Spring Harbor, 2001; Rodd 1989 "Chemistry of Carbon Compounds", vols. 1-5 and supps, Elsevier Science Publishers, 1989; "Organic Reactions", vols 1-40, John Wiley and Sons, New York, N.Y., 1991; March 2001, "Advanced Organic Chemistry", 5th ed. John Wiley and Sons, New York, N.Y. In the event of a conflict between the specification and any of the incorporated references, the specification shall control. Where numerical values herein are expressed as a range, endpoints are included.

BRIEF DESCRIPTION OF THE DRAWING

FIG. 1A illustrates treating a bone and/or cartilage matrix with a biological or chemical agent or condition that alters the structure of the bone matrix.

FIG. 1B illustrates how bone and/or cartilage preparations may be combined with biological or chemical agents (or conditions) that act on their substrates to generate peptide(s) or proteins fragment(s) that enhance the osteogenic, and/or chondrogenic activity of the preparation(s).

DEFINITIONS

Figure 2:
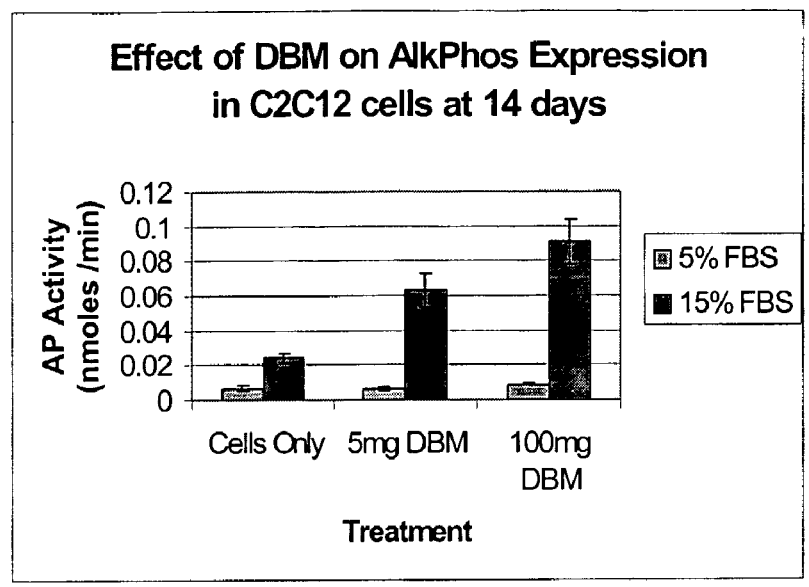
FIG. 2 is a bar graph showing alkaline phosphate activity in C2C12 cells cultured with DBM using a method corresponding to the work of Peel et al., referenced below. Cells were treated with DBM using transwell inserts in α-MEM containing either 5% (left bars in each group) or 15% FBS (right bars in each group).

Antibody, as used herein refers to any immunoglobulin or a derivative thereof which maintains binding ability, or any protein having a binding domain which is homologous or largely homologous to an immunoglobulin binding domain. Such proteins may be derived from natural sources, or partly or wholly synthetically produced (e.g., using recombinant DNA techniques, chemical synthesis, etc.). The antibody can be of any species, e.g., human, rodent, rabbit, goat, chicken, etc. The antibody may be a member of any immunoglobulin class, including any of the human classes: IgG, IgM, IgA, IgD, and IgE. In various embodiments of the invention the antibody may be a fragment of an antibody such as an Fab', F(ab')$_2$, scFv (single-chain variable) or other fragment that retains an antigen binding site, or a recombinantly produced scFv fragment, including recombinantly produced fragments. See, e.g., Allen, T., *Nature Reviews Cancer*, Vol. 2, 750-765, 2002, and references therein. Monovalent, bivalent or multivalent antibodies can be used. The antibody may be a chimeric or "humanized" antibody in which, for example, a variable domain of rodent origin is fused to a constant domain of human origin, thus retaining the specificity of the rodent antibody. It is noted that the domain of human origin need not originate directly from a human in the sense that it is first synthesized in a human being. Instead, "human" domains may be generated in vitro, in phage, in rodents whose genome incorporates human immunoglobulin genes, etc. See, e.g., Vaughan, et al., (1998), *Nature Biotechnology*, 16: 535-539. The antibody may be partially or completely humanized. An antibody may be polyclonal or monoclonal, though for purposes of the present invention monoclonal antibodies are generally preferred. Preferably the antibody specifically binds to its target on the cell surface, e.g., to a cell-type specific marker. Methods for producing antibodies that specifically bind to virtually any molecule of interest are known in the art. For example, monoclonal or polyclonal antibodies can be purified from natural sources, e.g., from blood or ascites fluid of an animal that produces the antibody (e.g., following immunization with the molecule or an antigenic fragment thereof) or can be produced recombinantly, in cell culture, etc. Antibodies that specifically bind to a number of proteins described herein are commercially available.

A peptide or protein fragment, or a bioactive agent, is associated with a bone or cartilage matrix or material (e.g., a bone particle) or other osteoinductive, osteogenic, or chondrogenic matrix or material according to the present invention if it is retained by the matrix or material long enough to affect its osteoinductive, osteogenic, or chondrogenic activity. Specific examples include 1) not freely diffusible from the matrix or material as determined in in vitro diffusion assays in simulated body fluids; and/or 2) has an extended half-life (e.g., at least 10%, 20%, 30%, 40%, 50%, or 100% longer) in the matrix or material as compared with free in solution. In some embodiments, associations are covalent; in others they are non-covalent. The bioactive agent may be rendered associated with a matrix or material by virtue of a physical interaction with one or more entities that are themselves associated with the matrix or material. Various stabilizing agents that can cause association with matrix are described in U.S. Ser. No. 10/271,140, filed Oct. 15, 2002, incorporated herein by reference.

Approximately is used herein to indicate that a value may vary within a range of 10% of the stated value.

Autograft, is used herein to refer to a tissue that is extracted from the intended recipient of an implant. Such material will be considered to be an autograft, even if it is prepared, processed, and/or expanded in tissue culture.

Bioactive agent or bioactive compound is used herein to refer to a compound or entity that alters, inhibits, activates, or otherwise affects biological or chemical events. For example, bioactive agents may include, but are not limited to, osteogenic or chondrogenic proteins or peptides, anti-AIDS substances, anti-cancer substances, antibiotics, immunosuppressants, anti-viral substances, enzyme inhibitors, hormones, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, angiogenic factors, anti-secretory factors, anticoagulants and/or antithrombotic agents, local anesthetics, ophthalmics, prostaglandins, anti-depressants, anti-psychotic substances, anti-emetics, and imaging agents. In certain embodiments, the bioactive agent is a drug. In some embodiments, the bioactive agent is a growth factor, cytokine, extracellular matrix molecule or a fragment or derivative thereof, for example, a cell attachment sequence such as RGD.

A more complete listing of bioactive agents and specific drugs suitable for use in the present invention may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", Edited by Susan Budavari et al., CRC Press, 1996; and the United States Pharmacopeia-25/National Formulary-20, published by the United States Pharmcopeial Convention, Inc., Rockville Md., 2001, each of which is incorporated herein by reference.

Biocompatible, as used herein, is intended to describe materials that upon administration in vivo, do not induce undesirable long-term effects.

Chemotactic, as used herein, means a substance having the ability to recruit cells from the host that have the potential for forming or repairing new bone or cartilage tissue and/or for contributing to such formation or repair (e.g., by providing growth factors). Certain chemotactic agents may also function as proliferation agents.

Chondrogenic, as used herein, means giving rise to or forming cartilage.

Chondrogenic activity refers to the cartilage forming ability of a matrix or material.

Demineralized, as used herein (e.g., in reference to a matrix), refers to any material generated by removing mineral material from tissue, e.g., bone tissue. In certain embodiments, the demineralized compositions described herein include preparations containing less than 5% calcium and preferably less than 1% calcium by weight. Partially demineralized bone (e.g., preparations with greater than 5% calcium by weight but containing less than 100% of the original starting amount of calcium) is also considered within the scope of the invention. In some embodiments, demineralized bone has less than 95% of its original mineral content.

Deorganified, as herein applied to matrices, particles, etc., refers to bone or cartilage matrices, particles, etc., that were subjected to a process that removes part of their original organic content. For example, in certain embodiments of the invention at least 5%, 10%, 20%, 30%, 40%, 50%, 60%, 70%, 80%, 90%, 95%, 98%, or even more of the original organic content may be removed, as determined based on weight. Matrices or particles that have been subjected to a process that removes essentially their entire original organic content are considered anorganic. For example, 99% or more of the organic content may be removed, as determined based on weight.

Diffusion barrier refers to any material, coating, film, or substance that decreases the rate of diffusion of a substance from one side of the barrier to the other side, and more specifically, from outside to in or vice versa. The diffusion barrier in certain embodiments may be a polymer including proteins, polysaccharides, cellulose, man-made polymer, PLGA, etc. that prevents the diffusion of activating agents (including water, enzymes, etc.) and/or degradatory enzymes into the DBM composition. The diffusion barrier may also prevent the movement of osteoinductive factors out of the DBM composition. In certain embodiments, the diffusion barrier is biodegradable, leading to the degradation, activation, or release of osteoinductive factors over an extended period of time. In other embodiments, the diffusion barrier may segmentally and/or regionally degrade to control the release rates in certain regions of the composition. For a more detailed description of diffusion barriers useful in stabilizing DBM compositions, see U.S. Ser. No. 10/271,140, filed Oct. 15, 2002; U.S. Ser. No. 60/392,462, filed Jun. 27, 2002; and U.S. Ser. No. 60/329,156, filed Oct. 12, 2001; each of which is incorporated herein by reference.

Generates, as used herein in relation to peptides or protein fragments, means to yield or to result in release of peptides and protein fragments. For example, a protease, chemical, or condition of the present invention can be contacted with a bone matrix to generate peptides and protein fragments having osteoinductive capability. The peptides can be generated, for example, by cleavage of a protein into active peptides or protein fragments, dissociation from a cofactor, changing the conformation of a peptide or protein, etc.

Operably linked or operably associated refers to a relationship between two nucleic acid sequences wherein the expression of one of the nucleic acid sequences is controlled by, regulated by, modulated by, etc., the other nucleic acid sequence. For example, the transcription of a nucleic acid sequence is directed by an operably linked promoter sequence; post-transcriptional processing of a nucleic acid is directed by an operably linked processing sequence; the translation of a nucleic acid sequence is directed by an operably linked translational regulatory sequence; the transport or localization of a nucleic acid or polypeptide is directed by an operably linked transport or localization sequence; and the post-translational processing of a polypeptide is directed by an operably linked processing sequence. Preferably a nucleic acid sequence that is operably linked to a second nucleic acid sequence is covalently linked, either directly or indirectly, to such a sequence, although any effective three-dimensional association is acceptable.

Osteogenic is used herein to refer to the ability of an agent, material, implant, etc. to enhance or accelerate the growth of new bone tissue by one or more mechanisms such as osteogenesis, osteoconduction, and/or osteoinduction.

Osteoinductive, as used herein, refers to the quality of being able to recruit cells from the host that have the potential to stimulate new bone formation. Any material that can induce the formation of ectopic bone in the soft tissue of an animal is considered osteoinductive. For example, most osteoinductive materials induce bone formation in athymic rats when assayed according to the method of Edwards et al. ("Osteoinduction of Human Demineralized Bone: Characterization in a Rat Model" *Clinical Orthopaedics & ReL. Res.*, 357:219-228, December 1998, incorporated herein by reference). In other instances, osteoinduction is considered to occur through cellular recruitment and induction of the recruited cells to an osteogenic phenotype. Osteoinductivity may also be determined in tissue culture as the ability to induce an osteogenic phenotype in culture cells (primary, secondary, or explants). The tissue culture method may be calibrated with an in vivo ectopic bone formation assay as described by Zhang et al. ("A quantitative assessment of osteoinductivity of human demineralized bone matrix"*J. Periodontol.* 68(11):1076-84, November 1997; incorporated herein by reference). Calibration of the in vitro assays against an art-accepted in vivo ectopic bone formation model may be desirable to confirm that the ability of a compound to induce an apparent "osteogenic" phenotype in tissue culture is correlated with the induction of new bone formation in vivo. BMP, IGF, TGF-$\beta$, and angiogenic factors are among the osteoinductive factors found to recruit cells from the marrow or perivascular space to the site of injury and then cause the differentiation of these recruited cells down a pathway responsible for bone formation. DBM isolated from either bone or dentin are both osteoinductive materials (Ray et al., "Bone implants" *J. Bone Joint Surgery* 39A: 1119, 1957; Urist, "Bone: formation by autoinduction" *Science* 150:893, 1965).

Osteoinductivity score refers to a score ranging from 0 to 4 as determined according to the method of Edwards et al. (1998) or an equivalent calibrated test. In the method of Edwards et al., a score of "0" represents no new bone formation; "1" represents 1%-25% of implant involved in new bone formation; "2" represents 26-50% of implant involved in new bone formation; "3" represents 51%-75% of implant involved in new bone formation; and "4" represents >75% of implant involved in new bone formation. In most instances, the score is assessed 28 days after implantation. However, the osteoinductivity score may be obtained at earlier time points such as 7, 14, or 21 days following implantation. In these instances it may be desirable to include a normal DBM control such as DBM powder without a carrier, and if possible, a positive control such as BMP. Occasionally osteoinductivity may also be scored at later timepoints such as 40, 60, or even 100 days following implantation. Percentage of osteoinductivity refers to an osteoinductivity score at a given time point expressed as a percentage of activity, of a specified reference score.

Osteoconductive, is used herein to refer to the ability of a non-osteoinductive substance to serve as a suitable template or substance along which bone may grow.

Markers for the purpose of the description of the invention may be any molecular moiety (e.g., protein, peptide, mRNA or other RNA species, DNA, lipid, carbohydrate) that characterizes, indicates, or identifies one or more cell type(s), tissue type(s), or embryological origin. A cellular marker may, but need not be, cell type specific. For example, a cell type specific marker is generally a protein, peptide, mRNA, lipid, or carbohydrate that is present at a higher level on or in a particular cell type or cell types of interest than on or in many other cell types. In some instances a cell type specific marker is present at detectable levels only on or in a particular cell type of interest. However, it will be appreciated that useful markers need not be absolutely specific for the cell type of interest. For example, certain CD molecules are present on the cells of multiple different types of leukocytes. In general, a cell type specific marker for a particular cell type is expressed at levels at least 3 fold greater in that cell type than in a reference population of cells which may consist, for example, of a mixture containing cells from a plurality (e.g., 5-10 or more) of different tissues or organs in approximately equal amounts. More preferably the cell type specific marker is present at levels at least 4-5 fold, between 5-10 fold, or more than 10-fold greater than its average expression in a reference population. Preferably detection or measurement of a cell type specific marker makes it possible to distinguish the cell type or types of interest from cells of many, most, or all other types. In general, the presence and/or abundance of most markers may be determined using standard techniques such as Northern blotting, in situ hybridization, RT-PCR, sequencing, microarray analysis, immunological methods such as immunoblotting, immunodetection, or fluorescence detection following staining with fluorescently labeled antibodies, oligonucleotide or cDNA microarray or membrane array, protein microarray analysis, mass spectrometry, etc. In the context of the present invention, markers of interest include markers characteristic of bone and/or cartilage-forming cells. Alkaline phosphatase is one such marker.

Polysaccharide, as used herein, refers to any polymer or oligomer of carbohydrate residues. The polymer may consist of anywhere from two to hundreds to thousands of sugar units. Polysaccharides may be purified from natural sources such as plants or may be synthesized de novo in the laboratory. Polysaccharides isolated from natural sources may be modified chemically to change their chemical or physical properties (e.g., phosphorylated, cross-linked). Polysaccharides may also be either straight or branch-chained. They may contain both natural and/or unnatural carbohydrate residues. The linkage between the residues may be the typical ether linkage found in nature or may be a linkage only available to synthetic chemists. Examples of polysaccharides include cellulose, maltin, maltose, starch, modified starch, dextran, and fructose. Glycosaminoglycans are also considered polysaccharides. Sugar alcohol, as used herein, refers to any polyol such as sorbitol, mannitol, xylitol, galactitol, erythritol, inositol, ribitol, dulcitol, adonitol, arabitol, dithioerythritol, dithiothreitol, glycerol, isomalt, and hydrogenated starch hydrolysates.

Proteases, as used herein, are protein-cleaving enzymes that cleave peptide bonds that link amino acids in protein molecules to generate peptides and protein fragments. A large collection of proteases and protease families has been identified. Some exemplary proteases include serine proteases, aspartyl proteases, acid proteases, alkaline proteases, metalloproteases, carboxypeptidase, aminopeptidase, cysteine protease, etc. An exemplary family of proteases is the proprotein convertase family, which includes furin (Dubois et al., *American Journal of pathology* (2001) 158(1):305-316). Members of the proprotein convertase family of proteases are known to proteolytically process proTGFs and proBMPs to their active mature forms (Dubois et al., *American Journal of Pathology* (2001) 158(1):305-316; Cui et al., *The Embo Journal* (1998) 17(16):4735-4743; Cui et al., *Genes & Development* (2001) 15:2797-2802, each incorporated by reference herein). Certain proteases are commercially available from chemical companies such as Aldrich-Sigma.

A peptide or protein fragment, as used herein, comprises a string of at least two amino acids linked together by peptide bond(s). Peptides and protein fragments preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a peptide may be modified, for example, by the addition of a chemical entity such as a carbohydrate group, a phosphate group, a farnesyl group, an isofarnesyl group, a fatty acid group, a linker for conjugation, functionalization, or other modification, etc. In various embodiments of the invention peptides and protein fragments may be cleavage products of longer proteins, e.g., proproteins, biologically inactive longer proteins, biologically active longer proteins, etc., which may or may not have undergone one or more posttranslational processing events.

Proliferation agent and mitogenic agent are used herein interchangeably to refer to the ability of a substance to enhance the proliferation of cells, e.g., cells of a subject, that have the potential to form new bone or cartilage or repair new bone or cartilage.

Purified, as used herein, means separated from one or more other molecules, compounds or entities with which it is naturally associated. A molecule, compound, or entity, etc., may be partially purified, substantially purified, or pure, where it is pure when it is removed from substantially all other compounds or entities, i.e., is preferably at least about 90%, more preferably at least about 91%, 92%, 93%, 94%, 95%, 96%, 97%, 98%, 99%, or greater than 99% pure. Purity may be quantified using either molar or weight percent.

Small molecule refers to organic compounds, whether naturally-occurring or artificially created (e.g., via chemical synthesis) that have relatively low molecular weight. Typically, small molecules have a molecular weight of less than about 1500 g/mol and have multiple carbon-carbon bonds.

Subject, as used herein, refers to an individual to whom an agent such as a bone repair matrix or cartilage repair matrix of the invention is to be delivered, e.g., for experimental, diagnostic, and/or therapeutic purposes. Preferred subjects are animals, for example, mammals, particularly domesticated mammals (e.g., dogs, cats, etc.), primates, or humans.

Targeting agent is any chemical entity that, when included in an inventive composition, will direct the composition to a particular site or cause the inventive composition to remain in a particular site within the recipient's body. A targeting agent may be a small molecule, peptide, protein, biomolecule, polynucleotide, etc. Typical targeting agents are antibodies, ligands of known receptors, and receptors. These targeting agents may be associated with the inventive composition through covalent or non-covalent interactions so that the inventive composition is directed to a particular tissue, organ, injured site, or cell type. A targeting agent, for example, may be associated with a peptide or protein fragment having osteoinductive or chondrogenic activity.

Vector, in general, refers to a nucleic acid molecule capable of mediating entry of, e.g., transferring, transporting, etc., a second nucleic acid molecule into a cell. The transferred nucleic acid is generally linked to, e.g., inserted into, the vector nucleic acid molecule. A vector may include sequences that direct autonomous replication, or may include sequences sufficient to allow integration into host cell DNA. Useful vectors include, for example, plasmids (typically DNA molecules although RNA plasmids are also known), cosmids, and viral vectors. As is well known in the art, the term viral vector may refer either to a nucleic acid molecule (e.g., a plasmid) that includes virus-derived nucleic acid elements that typically facilitate transfer or integration of the nucleic acid molecule (examples include retroviral or lentiviral vectors) or to a virus or viral particle that mediates nucleic acid transfer (examples include retroviruses or lentiviruses). As will be evident to one of ordinary skill in the art, viral vectors may include various viral components in addition to nucleic acid(s).

Xenogenic or xenogeneic is used herein to refer to a material intended for implantation that is obtained from a donor source of a different species than the intended recipient. For example, when the implant is intended for use in an animal such as a horse (equine), xenogenic tissue of, for example, bovine, porcine, caprine, etc, origin may be suitable.

DETAILED DESCRIPTION OF CERTAIN EMBODIMENTS

I. Introduction

The present invention provides improved bone and cartilage matrices that have been exposed to a treatment or condition that increases at least one biological activity of the matrix. In certain embodiments, the matrices contain peptides or protein fragments that increase the osteoinductive or chondrogenic properties of the bone or cartilage matrices. Below, certain aspects of preferred embodiments of the invention are described in more detail. Those of ordinary skill will appreciate that a variety of embodiments or versions of the invention are not specifically discussed below but are nonetheless within the scope of the present invention, as defined by the appended claims.

Bone is made up of collagen, mineral, and other non-collagenous proteins. Bone matrices can be mineralized, partially demineralized, demineralized, deorganified, anorganic, or mixtures of mineralized, partially demineralized, demineralized, deorganified, and/or anorganic. The present invention utilizes any one or a combination of mineralized, partially demineralized, demineralized, deorganified, or anorganic bone matrix. Demineralized bone matrix (DBM), as described herein, is comprised principally of proteins and glycoproteins, collagen being the primary protein component of DBM. While collagen is relatively stable, normally being degraded only by the relatively rare collagenase enzymes, various other proteins and active factors present in DBM are quickly degraded by enzymes present in the host. These host-derived enzymes include proteases and sugar-degrading enzymes (e.g., endo- and exo-glycosidases, glycanases, glycolases, amylase, pectinases, galacatosidases, etc.). Thus growth factor proteins in a DBM or added to a DBM may have a limited osteoinductive effect because they are rapidly inactivated by the proteolytic environment of the implant site or even within the DBM itself.

A similar problem arises in cartilage matrices, which also contain growth factors and other proteins that have a chondrogenic function or attract cells having a chondrogenic function. Cartilage is an avascular tissue composed of 5-10% by weight of living cells. Certain cartilage matrices are described in U.S. Pat. Nos. 5,270,300 and 5,041,138, incorporated herein by reference. Each of these patents describes a method for treating defects or lesions in cartilage, which provides a matrix, possibly composed of collagen, with pores large enough to allow cellular entry and population. The matrices further contain growth factors or other factors (e.g. angiogenesis factors) appropriate for the type of tissue regenerated. For example, TGF-β may be added to the matrix as a proliferation and chemotactic agent to induce differentiation of cartilage repair cells. However, such factors are potentially inactivated once they are implanted, resulting in a reduction in chondrogenic activity of cartilage matrices over time. Additional matrices for the generation and/or repair of cartilage include matrices comprising hydrogels, polymers, etc.

As mentioned above, a number of endogenous factors that play important roles in the development and/or repair of bone and/or cartilage have been identified. Bone morphogenetic proteins (BMP) such as BMP-2 and BMP-4 induce differentiation of mesenchymal cells towards cells of the osteoblastic lineage, thereby increasing the pool of mature cells, and also enhance the functions characteristic of differentiated osteoblasts (Canalis, E., et al., *Endocrine Rev.* 24(2):218-235, 2003). In addition, BMPs induce endochondral ossification and chondrogenesis. BMPs act by binding to specific receptors, which results in phosphorylation of a class of proteins referred to as SMADs. Activated SMADs enter the nucleus, where they regulate transcription of particular target genes. BMPs also activate SMAD-independent pathways such as those involving Ras/MAPK signaling. Unlike most BMPs such as BMP-2 and BMP-4, certain BMPs (e.g., BMP-3) act as negative regulators (inhibitors) of osteogenesis. In addition, it is noted that BMP-1 is distinct both structurally and in terms of its mechanism of action from other BMPs, which are members of the TGFβ superfamily. Unlike certain other BMPs (e.g., BMP-2, BMP-4), BMP-1 is not osteoinductive. Instead, BMP-1 is a collagenolytic protein that has also been shown to cleave chordin (an endogenous inhibitor of BMP-2 and BMP-4). Tolloid is a metalloprotease that is structurally related to BMP-1 and has proteolytic activity towards chordin. See, e.g., Canalis, et al., supra, for further details regarding the activities of BMPs and their roles in ostegenesis and chondrogenesis.

A variety of endogenous inhibitors of BMPs have been discovered in addition to chordin. These proteins act as BMP antagonists and include pseudoreceptors (e.g., Bambi) that compete with signaling receptors, inhibitory SMADs that block signaling, intracellular binding proteins that bind to activating SMADs, factors that induce ubiquitination and proteolysis of activating SMADs, and extracellular proteins that bind BMPs and prevent their binding to signaling receptors. Among the extracellular proteins are noggin, chordin, follistatin, members of the Dan/Cerberus family, and twisted gastrulation. These proteins, and their sequences are known and readily available to one of ordinary skill in the art.

II. Increasing the Biological Activity of a Bone or Cartilage Matrix

The present invention provides methods for increasing the biologic activity of a bone and/or cartilage matrix. The invention also provides bone or cartilage matrix compositions that have been exposed to a treatment, e.g., a biological or chemical agent, or condition that increases a biological activity of the matrix, relative to that of a matrix that has not been exposed to the treatment or condition. The biological activities that may be increased include, but are not limited to, osteoinductive activity, osteogenic activity, chondrogenic activity, wound healing activity, neurogenic activity, contraction-inducing activity, mitosis-inducing activity, differentiation-inducing activity, chemotactic activity, angiogenic or vasculogenic activity, exocytosis or endocytosis-inducing activity, etc. It will be appreciated that bone formation processes frequently include a first stage of cartilage formation that creates the basic shape of the bone, which then becomes mineralized (endochondral bone formation). Thus in many instances chondrogenesis may be considered an early stage of osteogenesis though of course it may also occur in other contexts.

The increase in biological activity may be assessed using any of a variety of in vitro or in vivo methods. For example, the ability of a treatment or condition to increase a biological activity of a matrix can be assessed using an assay such as the inventive tissue culture assays described in Section V and in Example 10. These assays measure the ability of a matrix to cause relatively undifferentiated mesenchymal lineage cells to display one or more features indicative of differentiation along an osteoblastic or chondrocytic lineage. The feature(s) can be expression of a marker characteristic of differentiation along an osteblastic or chondrocytic lineage, e.g., a marker that is normally expressed by osteoblast precursors, osteoblasts, chondrocytes, or precursors of chondrocytes. A preferred marker is alkaline phosphatase.

In certain embodiments of the invention the treatment or condition alters a biological activity of the matrix such that the matrix displays osteoinductive, osteogenic, and/or chondrogenic activity in a species in which a control matrix (e.g., an inactivated matrix or a matrix not exposed to the treatment or condition) does not show such activity (or shows it in a lesser amount). For example, a matrix exposed to the treatment or condition may display increased osteoinductive, osteogenic, and/or chondrogenic activity in human, dog, squirrel monkey, etc., as assessed either in vitro or in vivo.

In certain embodiments of the invention the matrix is exposed to a biological or chemical agent or to a combination of agents. The agent may be a cleavage agent, e.g., a protease such as collagenase(s), or a chemical agent such as cyanogen bromide. The cleavage agents may be applied either together or sequentially, optionally washing the matrix between application of different agents to remove residual agent. The matrix may be exposed to a variety of biological agents in addition to, or instead of, one or more proteases. Other enzymes include methylases, acylases, lipases, phospholipases, endo- and exo-glycosidases, glycanases, glycolases, amylase, pectinases, galacatosidases, etc. Chemical agents that perform similar reactions may be used. For example, a number of different alkylating agents are known. A variety of salts that can be present in high concentrations (e.g., at least 6 M, 7M, 8M, etc.) can be used. Exemplary salts include salts of various Group I elements, e.g., LiCl. Denaturing agents, e.g. denaturing salts such as guanidinium HCl can be used. It will be appreciated that where denaturing agents are used, care should be taken to avoid denaturing desired components present in the matrix, e.g., growth factors. In general, the biological and chemical agents are used in an effective amount and for a time sufficient to achieve a desired outcome, e.g., a desired increase in a biological activity of the matrix.

The matrix can be exposed to a physical condition instead of, or in addition to, a biological or chemical agent. For example, the matrix may be exposed to heat or cold for a suitable period of time, e.g., minutes, hours, or up to several days, where "heat" refers to temperatures above room temperature (about 23-25 degrees C.) and "cold" refers to temperatures below room temperature. Cycles of temperature change can be used, e.g., the matrix can be heated and cooled a plurality of times. The temperature may, for example, be at least 37 degrees C., at least 40, 50, 60, 70, 80, or 90 degrees C. Preferably the heat treatment is relatively gentle to avoid denaturing growth factors and other factors, typically proteins or peptides, that contribute to the osteogenic, osteoinductive, or chondrogenic activity of the matrix. One of ordinary skill in the art will know to avoid excessively high temperatures. The temperature may be 20 degrees C. or below, 15 degrees C. or below, 10 degrees C. or below, 0 degrees C. or below, etc. In general, the matrix may be exposed to any desired temperature in the presence or absence of other agents, solvents, etc. The matrix may be exposed to electromagnetic energy of any type, e.g., X-rays, microwaves, etc. Ionizing radiation, e.g., gamma-rays, beta-rays, etc., may be used. The treatment may be performed in the absence of oxygen or in a reduced oxygen environment. Following treatment, the level of biological activity may be determined through the use of any of the tests described herein, and those conditions leading to the preferred level of resultant activity may be chosen.

An alteration in physical structure may change at least one physical characteristic or parameter of the matrix. For example, the solubility of the matrix in one or more solvents (e.g., an aqueous medium) may be changed, e.g., increased, relative, for example, to the solubility of a standard DBM not exposed to the treatment. Preferably the aqueous medium is at physiological conditions, e.g., pH, osmotic pressure, salt concentration, etc. are within physiologically relevant ranges. For example, the pH may be approximately 7.2-8.0, or preferably 7.4-7.6. The osmotic pressure may be approximately 250-350 mosm/kg, 280-300 mosm/kg, etc. More generally, the pH may be between approximately 3-11, 4-10, 5-9, 6-8.5, etc. The osmotic pressure may be between 50-500 mosm/kg, 100-350 mosm/kg, etc. The salt concentration may be approximately 100-300 mM NaCl, e.g., approximately 150 mM NaCl. The aqueous medium may be tissue culture medium, blood, extracellular fluid, etc., and the physiological conditions may be conditions such as are typically found within these fluids and/or within a body tissue such as muscle. The solubility may be increased at any temperature, e.g., room temperature (~23-25 degrees), body temperature of a subject such as a human or animal, etc.

As described in Example 10, collagenase treatment of standard human DBM significantly increased its solubility relative to that of untreated standard human DBM. Thus the invention provides a human DBM composition exhibiting increased solubility in an aqueous medium compared to that of a standard DBM composition. The solubility of the human DBM composition is increased by exposure to an appropriate treatment or condition, e.g., collagenase treatment, radiation, heat, etc. The extent to which the solubility is increased may be varied by varying the nature of the treatment (e.g., the enzyme concentration) and/or the time over which it is applied. A combination of treatments may be used. In certain embodiments of the invention the solubility of the human DBM composition is greater than that of a standard DBM composition by between 10% and 4000% percent. For example, the solubility may be greater by between 10% and 100%, 100% and 500%, 500% and 1000%, 1000% and 2000%, 2000% and 3000%, 3000% and 4000% or any other range between 10% and 4000%. The solubility may be assessed at any time following the treatment. For example, the DBM may be placed in aqueous medium for a period of time such as 24-48 hours, 3, 4, 5, 6, or 7 days, 10 days, 14 days, etc. The amount of matrix remaining after the period of time is quantitated (e.g., dry weight is measured) and compared with the amount that was present initially. The extent to which the amount decreases after a period of time serves as an indicator of the extent of solubilization. The comparison may be to standard DBM prepared as described in Example 10 or to DBM prepared as described in references cited herein.

The solubility may be increased in vitro, in vivo, or both. In certain embodiments the increased solubility results in a composition that leaves less residual bone matrix at a site of implantation into a subject than is the case with standard DBM compositions. The invention therefore provides a human DBM composition, wherein implantation of the human DBM composition into a tissue (e.g., muscle) results in a residual amount of DBM within the tissue and wherein the area occupied by the human DBM composition divided by the area occupied by a standard DBM composition is less than or equal to 0.9 as determined after a period of time. The DBM is typically present as a collection of DBM material usually referred to as a nodule. The tissue may be muscle, e.g., rat muscle. The period of time is typically at least 24 hours, e.g., 24-72 hours, 1 week, 2 weeks, 4 weeks, 6 weeks, 8 weeks, etc. In other embodiments the area is less than or equal to 0.1-0.5, 0.5-0.9, or any intervening range. In certain embodiments of the invention the solubility of an inventive DBM composition is greater than that of human BMG Preferably the inventive human DBM composition exhibits higher biological activity than that of human BMG.

Other physical characteristics that may change as a result of exposure to the treatment or condition include, but are not limited to, porosity, hardness, strength, elasticity, conductivity, energy (e.g., light or heat) absorbance or scattering ability, transparency, etc. The alteration in physical structure may be observable using light and/or electron microscopy. For example, a change in the network architecture of the matrix may be observable.

If desired, one of ordinary skill in the art will be able to select appropriate parameters to evaluate or measure that reflect a change in one or more physical characteristics or parameters. Methods of measuring the parameters are generally known in the art. For example, the matrix can be characterized using various biophysical and optical instrumentation, such as circular dichroism (CD), dynamic light scattering, Fourier transform infrared (FTIR), atomic force microscopy (ATM), scanning electron microscopy (SEM), and transmission electron microscopy (TEM). Additionally, filament and pore size, fiber diameter, length, elasticity, and volume fraction may be determined using quantitative image analysis of scanning and transmission electron microscopy. The characterization can be performed on the matrix while in a particulate or fibrous form or after being molded into a larger shape such as an implant, e.g., as described below.

In certain embodiments of the invention the treatment or condition alters the physical structure of the matrix so as to increase its biological activity. Without wishing to be bound by any theory, altering the physical structure may "open up" the structure of the matrix, e.g., to allow biologically active molecules such as osteoinductive proteins or protein fragments, growth factors, etc., to be more readily released from or diffuse within the matrix and/or to allow components such as nutrients or growth-stimulatory molecules (e.g., molecules that upregulate collagen synthesis and/or induce cell proliferation) to enter the matrix. The treatment or condition may alter the structure of the matrix so as to facilitate the presentation of such molecules, e.g., on a surface of the matrix. The treatment or condition may alter the conformation of such molecules in a manner that facilitates interactions with target cells, e.g., cells that migrate towards or into the bone matrix. The treatment or condition may alter release kinetics of agents such as growth factors, differentiation factors, chemotactic factors, etc., from the matrix. Exemplary factors that upregulate collagen synthesis by osteoblasts include TGF-β, PDGF, IGF, IL-1, $PGE_2$, and certain BMPs. Certain treatments may alter, e.g., increase, the affinity of bone and/or cartilage forming cells and/or undifferentiated cells capable of differentiation into bone and/or cartilage forming cells for the matrix. For example, the treatment or condition may alter integrin binding sites (such as RGD sequences), e.g., by making them more available to cells. Other treatments include application or activation of cell adhesion molecules (CAMs), cadherins, etc., or application of an agent that activates such molecules. In certain embodiments, the matrix is converted to a gel through the use of any number of physical treatments (acid treatment, heating, ionic strength adjustment) known in the art. FIG. 1A (left side) illustrates treating a bone and/or cartilage matrix with a biological or chemical agent or condition that alters the structure of the bone matrix.

In certain embodiments of the invention alteration of the structure involves cleavage or partial degradation of one or more major structural component of the matrix such as collagen, e.g., components that typically make up at least 1%, 5%, 10%, 25%, 50%, 75%, 90% etc., of the dry weight of the matrix. In certain embodiments of the invention the secondary, tertiary, and/or quaternary structure of a major structural component of the matrix is altered. FIG. 1A (right side) illustrates a specific example of the general approach in which exposure to a biological or chemical agent or condition alters the structure of a bone matrix.

The alteration may include destruction of bonds that normally maintain the triple helical structure of collagen, bonds that hold collagen fibrils together, etc. DBM is a dense structure held together by crosslinked collagen. Most of the non-collagenous proteins (NCPs) are trapped within and/or attached to this framework. Certain agents such as collagenase can cut across the framework and thereby potentially allow access to the NCPs. The amount of collagen (or other structural protein) that is cleaved and/or degraded can vary. For example, in certain embodiments of the invention at least 10%, at least 25%, at least 50%, at least 75%, or at least 90% of the collagen originally present in the DBM is cleaved or degraded. Between 10-25%, 25-50%, 50-75%, 75-90%, 90-100%, or any other range such as 10-90%, 25-75%, etc., of the collagen may be cleaved or degraded. A polypeptide is considered to be cleaved if it is cleaved at a single site or at multiple sites. In certain embodiments of the invention the cleavage cleaves a crosslink. In certain embodiments of the invention at least a portion of the collagen is present as collagen fragments. For example, at least 10%, at least 25%, at least 50%, at least 75%, at least 90%, etc., of the collagen is present as collagen fragments in certain embodiments. Between 10-25%, 25-50%, 50-75%, 75-90%, 90-100%, or any other range such as 10-90%, 25-75%, etc., of the collagen may be present as collagen fragments. The fragments may remain associated with or present in or on the bone matrix or may diffuse away. A bone matrix can be exposed to any of a variety of different biological or chemical agents or conditions for different time periods in order to achieve a desired degree of cleavage or degradation of a structural component of the matrix such as collagen. The invention therefore provides a modified bone matrix comprising a collagen-containing bone matrix, wherein at least a portion of the collagen is cleaved or degraded. Matrices in which at least a portion of a different structural component of the matrix is cleaved or degraded are also provided.

In certain embodiments of the invention the matrix is exposed to a treatment or condition that generates peptides and protein fragments having osteoinductive or chondrogenic activity. In contrast to various longer proteins, certain peptides and protein fragments are less susceptible to proteolytic degradation and more likely to maintain their osteoinductive or chondrogenic properties in the proteolytic environment of the matrix or implant site. Many osteoinductive and chondrogenic proteins, for example, growth factors such as BMPs, cell signaling molecules, transcription factors, hormones, etc., have domains that are responsible for binding to receptors and/or initiating signal transduction in bone and cartilage growth pathways. These domains are capable of functioning independently as peptides and protein fragments. In certain embodiments, the present invention increases the osteoinductive or chondrogenic activity of bone and cartilage matrices by cleaving the osteoinductive and chondrogenic factors present in the matrix to generate active peptides or protein fragments and/or to generate active peptides or protein fragments that are less susceptible to degradation than their longer precursors. The increased number of factors in the matrix results in increased bone or cartilage formation.

In certain embodiments, the present invention provides methods of increasing the osteoinductivity of a bone matrix. As shown in FIG. 1B (left side) according to certain embodiments of the present invention, a bone or cartilage matrix composition, either mineralized, partially demineralized, demineralized, deorganified, anorganic, or a combination thereof, is contacted with at least one enzyme, such as a protease that cleaves one or more proteins in the bone matrix. Without wishing to be bound by any theory, the treatment may generate peptides or protein fragments having osteoinductive activity. Without limiting the theory of the present invention, the peptides or protein fragments generated, because they are already broken down and are less susceptible to further proteolytic degradation relative to the longer proteins from which they were derived, cause an increase in osteoinductivity of the bone matrix compared to a bone matrix not treated with a protease. The increase is also persistent over time since the peptides or protein fragments outlast longer protein precursors, which are subject to proteolytic breakdown.

In other embodiments, the present invention provides methods of increasing the chondrogenic activity of a cartilage repair matrix by providing a cartilage matrix and contacting a cartilage repair matrix with at least one protease that cleaves one or more proteins to generate peptides or protein fragments having chondrogenic activity. Since the peptides and protein fragments are not readily enzymatically degraded, generation of the active domains causes an increase in chondrogenic activity in the cartilage repair matrix compared to a cartilage repair matrix lacking a protease.

In addition to exposure to protease(s), the present invention provides methods of increasing the osteoinductivity of a bone matrix, or the chondrogenic activity of a cartilage repair matrix, by exposing the matrix to a lipase, a glycosidase, or any of a variety of other enzymes, or by including such enzymes in the matrix. The enzyme may alter the physical structure of the matrix and/or may generate peptides or protein fragments having the desired activity. In related embodiments, instead of a contacting the bone or cartilage matrix with an enzyme, the bone or cartilage matrix is contacted with a chemical or condition that alters the physical structure of the matrix and/or generates active peptide or protein fragments. For example, chemicals such as catalytic chemicals or reactive chemicals, such as acids, bases, cyanogen bromide (CNBr), etc., are known to digest or degrade proteins. Conditions that may cause protein degradation, resulting in the generation of active peptides and protein fragment domains include, for example, changes in temperature (e.g., heat or cold) and pH (e.g., acidic or basic conditions). Protein digestion or degradation that occurs via an agent such as protease that cleaves a substrate at one or more defined sites is referred to herein as specific degradation, or "cleavage", whereas protein digestion degradation that occurs via an agent or condition that cleaves a substrate at relatively random locations is referred to herein as non-specific degradation. Those skilled in the art will appreciate that a variety of biological or chemical agents or physical conditions can be used in the present invention. Degradation can be either partial or complete. Complete degradation means that the protein is broken down into individual amino acids. Generally partial degradation is sufficient to cause loss of biological activity and structural integrity.

In other embodiments, the present invention provides methods of increasing the osteoinductivity of bone matrix by exposing a bone matrix to at least one treatment (e.g., a biological or chemical agent) or condition that selectively degrades inhibitors of osteogenic activity. According to these embodiments, the resulting bone matrix has an increased osteoinductivity, osteogenic or chondrogenic activity compared to a bone matrix not exposed to the treatment or condition, because inhibition of an osteoinductive, osteogenic, or chondrogenic factor is blocked. This increases the overall osteogenic potential of the bone matrix. In related embodiments, the present invention provides methods of increasing the chondrogenic activity of a cartilage repair matrix by exposing the cartilage repair matrix to a treatment (e.g. a biological or chemical agent) or physical condition that selectively degrades inhibitors of chondrogenic activity, wherein the result is a cartilage repair matrix having improved cartilage formation compared to a cartilage repair matrix not exposed to the treatment or condition. By blocking the inhibition of chondrogenic factors, the overall chondrogenic activity of the matrix is increased. In general, agents that inhibit or reduce osteoinductive, osteogenic, or chondrogenic activity may be referred to as bone/cartilage inhibitory factors (BCIF).

As will be appreciated by those skilled in the art, factors having osteoinductive, osteogenic, and/or chondrogenic activity can be inhibited by a variety of mechanisms including proteolytic degradation, binding or sequestration of the factor, etc. The present invention provides methods of preventing such inhibition. In various embodiments of the invention, any biological or chemical agent or condition that reduces or prevents inhibition of osteoinductive or chondrogenic factors may be used in the present invention to increase the overall osteogenic or chondrogenic potential of a bone or cartilage matrix. A variety of proteins or protein fragments inhibit the osteoinductive and/or osteogenic activity of certain bone morphogenetic proteins such as BMPs-2, -4, -5, -6, and -7. Among these inhibitory agents are noggin, chordin, gremlin, Dan, Cerberus, the protein related to Dan and Cerberus (PRDC), caronte, Dante, sclerostin, follistatin, follistatin-related gene (FLRG), ventroptin, alpha2 HS-glycoprotein. For example, noggin blocks the effect of BMPs in cells of the osteoblastic lineage, and the addition of noggin to osteoblasts in culture blocks BMP-induced synthesis of collagen and non-collagen proteins and also inhibits the stimulatory effect of BMPs on alkaline phosphatase actvity. Chordin acts in a similar fashion. Further details regarding these inhibitory agents are found in Canalis, et al., supra, and references cited therein.

Certain collagen fragments are also believed to inhibit BMPs. For example, a potentially inhibitory collagen fragment corresponds to the C-terminal end of procollagen that is released during extracellular matrix remodeling and collagen assembly.

In accordance with the invention, the osteoinductive, osteogenic, and/or chondrogenic activity of a bone matrix composition is increased by exposing the bone matrix to a treatment or condition that inactivates, blocks, or degrades one or more of these inhibitory molecules. Bone or cartilage inhibitory factors (BCIF) can be inactivated or inhibited by a variety of methods. For example, a specific protease that cleaves or degrades the BCIF can be used. Another approach is to use an antibody that binds to the BCIF and blocks its interaction with a positively acting factor such as BMP-2 or BMP-4. The antibody may inhibit post-translational modification, transport, etc., of the inhibitory agent. Antibodies to the inhibitory agents mentioned herein (and others) are known in the art or could be generated using known methods without undue experimentation. Either polyclonal or monoclonal antibodies, or antigen-binding fragments thereof, can be used. Other agents having specific binding ability (e.g., affibodies) could likewise be used. One of ordinary skill in the art will be able to generate appropriate antibodies, affibodies, etc., based upon the known sequences of the inhibitory proteins. In certain embodiments the treatment or condition inactivates a BCIF that is normally expressed in osteoblasts and/or chondrocytes.

The invention therefore provides a modified bone matrix comprising a collagen-containing bone matrix, wherein at least a portion of an inhibitor of osteoinductive, osteogenic, or chondrogenic activity is cleaved or degraded. For example, at least 10%, at least 25%, at least 50%, at least 75%, or at least 90% of the inhibitor is cleaved or degraded in various embodiments of the invention. Between 10-25%, 25-50%, 50-75%, 75-90%, 90-100%, or any other range such as 10-90%, 25-75%, etc., of the inhibitor may be present as fragments. The fragments may remain associated with or present in or on the bone matrix or may diffuse away. A bone matrix can be exposed to any of a variety of different biological or chemical agents or conditions for different time periods in order to achieve a desired degree of cleavage or degradation of an inhibitor.

In certain embodiments of the invention a first agent or condition that alters the physical structure of the matrix is used in combination with a second agent or condition that cleaves or degrades a specific protein, e.g., an inhibitor of BMP. Typically, the first agent or condition selectively affects the collagen matrix, and the second agent or condition acts on a specific protein that is not a major structural component of the matrix. The specific protein generally makes up less than 1% of the dry weight of the matrix, e.g., less than 0.5%, less than 0.1%, etc. The specific protein can be a positively acting agent such as a BMP or BMP precursor, wherein cleavage of the BMP or BMP precursor generates active peptides or protein fragments. The specific protein can be a negatively acting factor, e.g., an inhibitor of a BMP or an inhibitor of a BMP signaling pathway, wherein cleavage or degradation of the inhibitor allows increased activity of the protein that it would otherwise inhibit. Exemplary treatments include a first treatment with collagenase and/or heat and a second treatment with one or more proteases selected from the group consisting of bone morphogenetic protein-1 (BMP-1), tolloid, pepsin, trypsin, papain, cathepsins such as cathepsin C or cathepsin K, and furin. The treatments may be applied in combination or sequentially. One or more rounds of treatment may be used, i.e., the treatments may alternate.

In certain embodiments of the invention, a first protease that cleaves a protein to generate active peptides or protein fragments can be used in combination with a second protease (or a chemical or condition) that blocks inhibition of one or more osteoinductive or chondrogenic factors. For example, the second protease may cleave or degrade a protein that would otherwise sequester an osteoinductive or chondrogenic factor, thereby releasing the factor and allowing it to become active. As another example, a protease inhibitor that inhibits a protease known to degrade an osteoinductive or chondrogenic factor can be included in the matrix. In other preferred embodiments, certain chemicals or conditions may be used in combination to both generate osteoinductive or chondrogenic peptides or protein fragments and block inhibition of such factors in bone and cartilage matrices. By combining the methods, as described herein, the osteoinductivity or chondrogenic activity of a bone or cartilage matrix, respectively may be further increased.

In other preferred embodiments, the present invention provides osteoinductive bone matrix compositions for implantation into a bone defect site. In certain preferred embodiments of the invention the compositions comprise a bone matrix including partially demineralized, demineralized, deorganified, or anorganic bone matrix, or a combination there of, treated with at least one protease. The protease causes cleavage of inactive proteins and/or proteins that are susceptible to cleavage or degradation in the body, to generate osteoinductive peptides or protein fragments. The osteoinductive peptide or protein fragments have increased osteoinductivity relative to the uncleaved protein(s) and/or are less susceptible to cleavage or degradation. The resulting bone matrix has an increased osteoinductivity compared to an untreated matrix, resulting in improved bone formation. In other embodiments of the invention, a chemical or condition that causes degradation or digestion of inactive proteins and/or cleavage of proteins that are susceptible to cleavage or degradation in the body, is used in order to generate osteoinductive peptides or protein fragments, resulting in a bone matrix having increased osteoinductivity. In yet other preferred embodiments, the bone repair matrix may include proteases or chemicals that generate osteoinductive peptides or protein fragments in combination with proteases or chemicals that block inhibitor(s) of osteoinductive factors. Such combined formulations result in a further increase in osteoinductivity of the bone matrix.

Cartilage repair matrix compositions are also provided for implantation into a cartilage defect site, which include a cartilage repair matrix treated with at least one protease that causes cleavage of inactive proteins and/or cleavage of proteins that are susceptible to cleavage or degradation in the body, to generate chondrogenic peptides or protein fragments that have increased activity relative to the uncleaved protein(s) and/or are less susceptible to cleavage or degradation. The treated cartilage repair matrix has increased chondrogenic activity compared to an untreated cartilage repair matrix, resulting in improved cartilage formation. The cartilage repair matrix compositions may further include one or more chemicals or conditions that increase or replace the function of the protease in generating peptides and protein fragments having chondrogenic activity. In other preferred embodiments, as recited herein, proteases, chemicals, or conditions that block inhibitors of chondrogenic activity may also be included. Such combined formulations result in a further increase in chondrogenic activity of the cartilage repair matrix.

Thus certain cartilage repair matrices of the invention include stromelysin, which acts to increase the amount of this peptide in the matrix. It has also been shown that two major proteases, an initial serine proteinase followed by a metalloproteinase, act in sequence to degrade this peptide (Dean M F and Sansom P., *Biochem J.* 2000 Jul. 15; 349(Pt 2):473-9). Therefore in certain embodiments of the invention inhibitor(s) of one or both of these proteases are included in the matrix in order to reduce degradation of the cartilage growth factor Link N peptide.

In other preferred embodiments, the present invention provides bone matrices containing one or more peptides or protein fragments having osteoinductive activity. The bone matrix including the osteoinductive peptides or protein fragments has enhanced osteoinductive properties and improved bone formation ability compared to a bone matrix lacking the peptides or protein fragments. In related embodiments, the present invention provides cartilage repair matrices containing peptides or protein fragments that are capable of enhancing the chondrogenic activity of the cartilage repair matrix, resulting in improved cartilage formation ability compared to a composition without the peptide or protein fragment.

A variety of peptides and protein fragments can be generated or included in the bone and cartilage matrices of the present invention, as long as they enhance the osteogenic, osteoinductive or chondrogenic activity of the matrix. In certain preferred embodiments, the peptides and protein fragments can be endogenous and/or exogenous to the matrix. For example, the peptides and protein fragments used in the invention can be derived from growth factors such as, for example, bone morphogenic proteins (e.g., BMP-2, BMP-3, BMP-4, BMP-5, BMP-6, BMP-7, BMP-8, BMP-9, BMP-10, BMP-11, BMP-12, and BMP-13), transforming growth factors (TGF) (e.g., from the TGF-β superfamily, e.g., TGF-β), osteogenic factors, vascularizing factors, macrophage colony stimulating factor (MCSF), insulin-like growth factor (e.g., IGF-1), angiogenic factors (e.g., vascular endothelial growth factor (e.g., VGEF), osteonectin, alpha-2-HS glycoprotein, osteocalcin, osteopontin, etc. In other preferred embodiments the peptides or protein fragments can be derived from any other collagenous or non-collagenous protein (for example, matrix GLA protein etc.) alone or in combination. In other preferred embodiments the peptides and protein fragments are derived from cell signaling molecules, transcription factors, or hormones. In yet other preferred embodiments the targets of the biological or chemical agents or conditions of the invention are growth factors agonists. There are also likely to be other unnamed or undiscovered osteoinductive and chondrogenic factors present in bone and cartilage matrix compositions.

In certain preferred embodiments, active peptides and protein fragments can be added in combination with any of a variety of growth factor agonists and bioactive agents (e.g., anti- or pro-inflammatory modulators or drugs), as described herein below. Certain preferred bioactive agents include hormones such as estrogen and parathyroid hormone or other endogenously produced molecules such as prostaglandins. For example, stimulation of the estrogen receptor-α stimulates the adaptive response of bone to mechanical loading, suggesting that estrogen may increase osteoinductivity of a bone matrix (see Lee et al., *Nature*, (July, 2003) 424:389).

Synthetic compounds that have osteoinductive or chondrogenic activity may also be included in the present bone and cartilage formulations. For example, agonists of EP2 receptor selective prostaglandin E2, such as the nonpeptidyl CP,533, 536, have been shown to induce bone healing, making such molecules prime candidates to include in, e.g., demineralized bone matrices etc, see Paralkar et al., *Proc. Natl, Acad. Sci., USA*, (May, 2003) 100(11): 6736-6740; Seppa, *Science News*, (May 2003) 163:309-310). Those skilled in the art will appreciate that other synthetic molecules having osteogenic or chondrogenic activity could also be included in a bone or cartilage matrix. Means of identifying such synthetic molecules are described in, for example, Paralkar et al., supra, or Seppa, supra. Other methods of identifying such synthetic molecule are known in the art.

Development of a vasculature around the implant site may also be important to forming new bone and/or cartilage tissues. Angiogenesis may be an important contributing factor for the replacement of new bone and cartilage tissues. In certain preferred embodiments of the invention, angiogenesis is promoted so that blood vessels are formed at the site to allow efficient transport of oxygen and other nutrients and growth factors to the developing bone or cartilage tissue. In particularly preferred embodiments, angiogenesis promoting factors are included in the bone or cartilage matrix to increase angiogenesis in that region. For example, class 3 semaphorins, e.g., SEMA3, controls vascular morphogenesis by inhibiting integrin function in the vascular system (Serini et al., *Nature*, (July 2003) 424:391-397, incorporated herein by reference) and may be included in the matrix.

In certain preferred embodiments of the present invention, cytokine inhibitors are added to the cartilage matrix to improve bone and cartilage repair. The presence of cytokines, particularly in cartilage, is associated with abnormal extracellular matrix remodeling and loss. A variety of cytokines may have this effect, including, interleukins such as members of the interleukin-1 (IL-1) family of cytokines (IL-1α, IL-1β, IL-18, and IL-1ra), see Lotz, *Clinical Orthopaedics and Related Research*, (2001) 391S: S108-S115). Transforming growth factor-β can compensate for the catabolic effects of IL-1 and enhance cartilage repair, (see van den Berg et al., *Clinical Orthopaedics and Related Research*, (2001) 391S: S2244-S250r). In addition, it has been shown that transforming growth factor-β and bone morphogenetic protein-2 induce chondrophyte formation at the margins of arthritic joints, contributing to spontaneous cartilage repair and chondrophyte formation in arthritic joints (van den Berg et al., supra.). Thus, in certain preferred embodiments of the invention, cartilage matrices include cytokine inhibitors such as transforming growth factor-β and bone morphogenetic protein-2.

In other preferred embodiments, the peptides or protein fragments of the invention, whether generated in the matrix or added to the matrix mechanically, are covalently or non-covalently attached to the matrix using standard methods, which are well known in the art. Those skilled in the art will further appreciate that in some cases this may require modification of the peptide or protein fragment with a chemical entity or group.

Other preferred embodiments of the present invention provide methods of preparing a bone matrix composition, which include 1) providing the bone matrix, and 2) introducing into and/or adsorbing onto the bone matrix peptides or protein fragments that are capable of enhancing the osteoinductivity of the bone matrix, resulting in improved bone formation ability, as compared to a composition without the peptides or protein fragments. Similarly, these methods applied to cartilage include 1) providing a cartilage repair matrix, and 2) introducing into and/or adsorbing onto the cartilage repair matrix peptides or protein fragments that are capable of enhancing the chondrogenic activity of the cartilage repair matrix, resulting in improved cartilage formation ability compared to a composition without the peptides and protein fragments.

In another embodiment, the present invention provides methods of treating a bone or cartilage defect, by implanting the inventive bone or cartilage matrix compositions into an animal, preferably a human, at the site of the bone or cartilage defect. In certain embodiments demineralized bone (either cortical, cancellous, cortical/cancellous or combinations thereof) most often in the shape of fibers is treated with the proprotein convertase, furin, which specifically activates BMPs, as shown schematically in FIG. 1B (right side). The matrix is contacted with furin, BMPs are activated and furin and other unwanted components are then optionally washed away from the matrix. Any one of: the type of the matrix, the shape of the matrix, the type of treatment, and the specific peptides and proteins activated, as well as an optional inactivation step, may be substituted, with another, as described herein.

A variety of post treatment steps can be used to eliminate a biological or chemical agent such as protease and/or unwanted components from the bone or cartilage matrix in addition to, or instead of, a washing step. In certain embodiments of the invention the agent(s) and/or unwanted component(s) are inactivated by heat, chemicals, or quenching with excess substrate. In other embodiments, the agent(s) and/or unwanted component(s) are not inactivated or removed from the bone or cartilage matrix.

In certain preferred embodiments of the invention, one or more enzymes, such as proteases, lipases, glycosidases, are added to the matrix to activate the osteoinductive or chondrogenic factors already present (e.g., to convert one or more factors from an inactive to an active form or from an active form to a more active form, or from a form that is susceptible to degradation to a form that is less susceptible to degradation, e.g., a form that has a longer half-life). In other preferred embodiments, one or more chemical treatments or application of a condition with or without simultaneous enzymatic treatment activates osteoinductive or chondrogenic factors. Many of the growth factors responsible for the osteoinductive or chondrogenic activity of the matrix exist in cryptic form, in the matrix, until activated. Activation can involve the change of a pre or pro function of a factor, or release of the function from a second factor or entity, which binds to the first growth factor. For example, proteolytic cleavage results in separation of the inactive proprotein (e.g., a proprotein from the TGF superfamily of proproteins, e.g., TGF-β) and release of an active, mature peptide. As proteins of bone and cartilage matrices degrade naturally or artificially, they break down into peptides and protein fragments that contain active domains and function as receptor ligands and signal transducers in bone and cartilage growth signaling pathways. The present invention promotes these reactions for the enhancement of osteoinductive and chondrogenic signaling in the bone and cartilage matrices of the invention.

The methods of the invention may be similar to processes that naturally occur in the body. As is well known in the art, many proteins undergo proteolytic cleavage following translation. The simplest form of this is the removal of the initiation methionine. Many proteins are synthesized as inactive precursors that are activated under proper physiological conditions by limited proteolysis. Pancreatic enzymes and enzymes involved in clotting are examples of the latter. Inactive precursor proteins that are activated by removal of polypeptides are termed, proproteins.

Proteins that are membrane bound or are destined for excretion are synthesized by ribosomes associated with the membranes of the endoplasmic reticulum (ER). The ER associated with ribosomes is termed rough ER (RER). This class of proteins all contain an N-terminus termed a signal sequence or signal peptide. The signal peptide is usually 13-36 predominantly hydrophobic residues. The signal peptide is recognized by a multi-protein complex termed the signal recognition particle (SRP). This signal peptide is removed following passage through the endoplasmic reticulum membrane. The removal of the signal peptide is catalyzed by signal peptidase. Proteins that contain a signal peptide are called preproteins to distinguish them from proproteins. However, some proteins that are destined for secretion are also further proteolyzed following secretion and, therefore contain pro sequences. This class of proteins is termed preproproteins.

A complex example of post-translational processing of a preproprotein is the cleavage of prepro-opiomelanocortin (POMC) synthesized in the pituitary. This preproprotein undergoes complex cleavages, the pathway of which differs depending upon the cellular location of POMC synthesis. Another is example of a preproprotein is insulin. Since insulin is secreted from the pancreas it has a prepeptide. Following cleavage of the 24 amino acid signal peptide the protein folds into proinsulin. Proinsulin is further cleaved yielding active insulin which is composed of two peptide chains linked together through disulfide bonds. Still other proteins (of the enzyme class) are synthesized as inactive precursors called zymogens. Zymogens are activated by proteolytic cleavage such as is the situation for several proteins of the blood clotting cascade. In certain embodiments, the present invention may mimic and/or enhance certain naturally occurring processes that result in production of active molecules from inactive precursors.

In preferred embodiments, the invention provides highly osteoinductive bone matrices by treating bone and cartilage preparations of various forms with enzymes, chemicals, or conditions, which process any immature osteoinductive proproteins into their active mature forms. Similarly, the invention further provides highly chondrogenic cartilage repair matrices by treating cartilage grafts with proteases, chemicals, or conditions that process any immature chondrogenic factors into their active mature forms.

A wide variety of agents, selected from biological agents such as enzymes, chemicals, and conditions can be used in the present invention to generate osteoinductive peptides and protein fragments, and these are well known in the art. The proteases, chemicals, and conditions of the present can be site specific, amino acid site specific, protein specific, semi-site-specific, lipid specific, or sugar specific, etc.

The enzymes of the invention may be obtained from endogenous, exogenous, autogenic (autologous), allogenic, or xenogenic sources. They may be purified from natural sources or produced recombinantly. In many embodiments the enzymes are purchased from commercial sources (Worthington Biochemical Industries, Sigma, etc.) and either used directly or subsequently purified to be free of contaminants which may negatively affect the activity of the final product. According to the present invention, enzymes, peptides or protein fragments (e.g., generated by particular proteases) and other treatments may also be purified by conventional methods (see, e.g., Sambrook et al., *Molecular Cloning: A Laboratory Manual*, Cold Spring Harbor Press, N.Y.; Ausubel et al. "*Current Protocols in Molecular Biology*, Greene Publishing Associates, New York, V 1 & 2 1996). Purification can be carried out by a variety of chromatographic techniques. Size exclusion chromatography is commonly used. Other methods include ion exchange, hydrophobic interaction, and affinity chromatography. Peptides or protein fragments may be used in the bone or cartilage repair matrix as unpurified preparations as long as the peptides or protein fragments maintain their osteoinductive or chondrogenic activity. Alternatively, the enzymes, peptides or protein fragments can be synthesized artificially using conventional techniques, produced recombinantly, etc. It may be preferable to use preparations having a high degree of purity. For example, an enzyme preparation may contain at least 90%, at least 95%, at least 98%, at least 99% of the enzyme by weight. The preparation may be essentially free of bacterial components, particularly bacterial components that could cause inflammatory or immunological reactions in a host, such as endotoxin, lipopolysaccharide, etc. Preparations having a purity greater than 99.5% can be used.

A particularly preferred protease is a collagenase. Collagenases and their activity on collagens of various types have been extensively studied. A number of collagenase preparations are available from Worthington Biochemical Corporation, Lakewood, N.J. As described on the company's web site and well known in the art, collagen consists of fibrils composed of laterally aggregated, polarized tropocollagen molecules (MW 300,000). Each tropocollagen unit consists of three helically wound polypeptide α-chains around a single axis. The strands have repetitive glycine residues at every third position and numerous proline and hydroxyproline residues, with the particular amino acid sequence being characteristic of the tissue of origin. Tropocollagen units combine uniformly to create an axially repeating periodicity. Cross linkages continue to develop and collagen becomes progressively more insoluble and resistant to lysis on aging. Gelatin results when soluble tropocollagen is denatured, for example on mild heating, and the polypeptide chains become randomly dispersed. In this state the strands may readily be cleaved by a wide variety of proteases.

In general, a variety of different collagenases known in the art can be used. Collagenases are classified in section 3.4.24 under the International Union of Biochemistry and Molecular Biology (NC-IUBMB) enzyme nomenclature recommendations (see, e.g., 3.4.24.3, 3.4.24.7, 3, 4.24.19). The collagenase can be of eukaryotic (e.g., mammalian) or prokaryotic (bacterial) origin. Bacterial enzymes differ from mammalian collagenases in that they attack many sites along the helix. Collagenase may cleave simultaneously across all three chains or attack a single strand. Preferably the collagenase cleaves Type I collagen, e.g., degrades the helical regions in native collagen preferentially at the Y-Gly bond in the sequence Pro-Y-Gly-Pro- where Y is most frequently a neutral amino acid. This cleavage yields products susceptible to further peptidase digestion. Any protease having one or more of these activities associated with collagenase may be used as a collagenase in accordance with the present invention.

It will be appreciated that crude collagenase preparations contain not only several collagenases but also a sulfhydryl protease, clostripain, a trypsin-like enzyme, and an aminopeptidase. This combination of collagenolytic and proteolytic activities is effective at breaking down intercellular matrices, the essential part of tissue dissociation. Crude collagenase is inhibited by metal chelating agents such as cysteine, EDTA or o-phenanthroline but not DFP. It is also inhibited by α2-macroglobulin, a large plasma glycoprotein. $Ca^{2+}$ is required for enzyme activity. Therefore it is preferable to avoid collagenase inhibiting agents when treating bone matrix with collagenase. In addition, although the additional proteases present in some collagenase preparations may aid in breaking down tissue, they may also cause degradation of desired matrix constituents such as growth factors. Therefore, it may be preferable to use a highly purified collagenase that contains minimal secondary proteolytic activities along with high collagenase activity. For example, a collagenase preparation may contain at least 90%, at least 95%, at least 98%, at least 99% collagenase by weight. The preparation may be essentially free of bacterial components, particularly bacterial components that could cause inflammatory or immunological reactions in a host, such as endotoxin, lipopolysaccharide, etc. Preparations having a purity greater than 99.5% can be used. A suitable preparation is chromatographically purified CLSPA collagenase from Worthington Biochemical Corporation. It may be desirable to include various protease inhibitors that do not inhibit collagenase but that inhibit various proteases that digest BMP. For example, protease inhibitors that are known to protect BMP activity from degradation include N-ethyl maleimide, benzamidine hydrochloride, iodoacetic acid, PMSF, AEBSF, E-64. Bestatin may also be used, particularly if the preparation contains aminopeptidase activity. Any of these protease inhibitors (or others) can be included in a bone matrix composition or in any composition that is used to treat a bone matrix composition.

Another protease of use in the invention is bone morphogenetic protein 1 (BMP-1). As mentioned above, BMP-1 is a collagenolytic protein that has also been shown to cleave chordin (an inhibitor of BMP-2 and BMP-4). Thus in accordance with the present invention BMP-1 is of use to alter the physical structure of the matrix (e.g., by breaking down collagen) and/or to cleave specific inhibitory protein(s), e.g., chordin or noggin.

Proteins related to any of the proteases described herein, i.e., proteins or protein fragments having the same cleavage specificity, can also be used. It will be appreciated that variants having substantial sequence identity to naturally occurring protease can be used. For example, variants at least 80% identical over at least 50%, at least 60%, at least 70%, at least 80%, at least 90%, or 100% of the length of naturally occurring protease (or any known active fragment thereof that retains cleavage specificity) when aligned for maximum identity allowing gaps can be used.

Certain preferred proteases include members of the proprotein convertase (PPC) family of proteases, such as furin and related proteases. Members of this family of cellular enzymes cleave most prohormones and neuropeptide precursors. Numerous other cellular proteins, some viral proteins, and bacterial toxins that are transported by the constitutive secretory pathway are also targeted for maturation by PCs. Furin and other PC family members share structural similarities which include a heterogeneous ~10 kDa amino-terminal proregion, a highly conserved ~55 kDa subtilisin-like catalytic domain, and carboxyl-terminal domain that is heterogeneous in length and sequence. These enzymes become catalytically active following proregion cleavage within the appropriate cellular compartment.

Furin is the major processing enzyme of the secretory pathway and is localized in the trans-golgi network (van den Ouweland, A. M. W. et al. (1990) Nucl. Acid Res. 18, 664; Steiner, D. F. (1998) Curr. Opin. Chem. Biol. 2, 31-39). Substrates of furin include blood clotting factors, serum proteins and growth factor receptors such as the insulin-like growth factor receptor (Bravo D. A. et al. (1994) J. Biol. Chem. 269, 25830-258373). The minimal cleavage site for furin is Arg-X-X-Arg. However, the enzyme prefers the site Arg-X-(Lys/Arg)-Arg. An additional arginine at the P6 position appears to enhance cleavage (Krysan D. J. et al. (1999) J. Biol. Chem. 274, 23229-23234). Furin is inhibited by EGTA, α1-antitrypsin Portland (Jean, F. et al. (1998) Proc. Natl. Acad. Sci. USA 95, 7293-7298) and polyarginine compounds (Cameron, A. et al. (2000) J. Biol. Chem. 275, 36741-36749).

Furin has been shown to proteolytically process both pro-TGF and proBMP proteins, for example, proTGF-β and proBMP-4, respectively, resulting in the release of the active mature form for each molecule (Dubois et al., *American Journal of Pathology* (2001) 158(1):305-316; Cui et al., *The Embo Journal* (1998) 17(16):4735-4743; Cui et al., *Genes & Development* (2001) 15:2797-2802, each incorporated by reference herein). Furin has also been shown to cleave BMP-2, BMP-6, and BMP-7. For example, furin cleaves between amino acids 282 and 283 in mature human BMP-2. Newly synthesized human BMP-2 contains a signal sequence (amino acids 1-23), a propeptide (amino acids 24-282), and an active portion (amino acids 283-396). Furin cleaves mature BMP-2 (amino acids 24-396) between amino acids 282 and 283 to release the propeptide and the active molecule.

In accordance with certain embodiments of the invention treating DBM with PPCs such as furin and/or other proteases, which process immature TGF-β and/or BMP superfamily propeptides into their active mature forms and/or process active or inactive TGF-β and/or BMP superfamily polypeptides into smaller active fragments that are resistant to degradation or inactivation relative to the longer polypeptide, generates a bone matrix with increased osteoinductivity compared to a bone matrix lacking the protease, resulting in improved bone formation. The higher titers of the mature and/or degradation resistant species in these preparations increase the osteoinductive capacity of the bone matrix. Preferably, the activation of active factors and/or the generation of degradation-resistant active fragments within the bone matrix increases the overall osteoinductive activity of the bone matrix, compared to bone matrix lacking a protease.

Proteases such as PPCs can also be applied to cartilage repair matrices to activate peptides and protein fragments having chondrogenic activity. This yields a cartilage repair matrix having increased chondrogenic activity compared to a cartilage repair matrix lacking the protease. The activation of chondrogenic peptides and protein fragments within the cartilage repair matrix increases the overall chondrogenic activity of the matrix and results in improved cartilage formation, compared to a cartilage repair matrix lacking a protease.

According to the present invention, activation of a peptide or protein fragment can be either specific or non-specific. Cleavage of a protein, e.g., with a particular protease to generate active peptides and protein fragments is referred to as specific activation, or specific digestion or degradation. Non-specific activation can occur when protein digestion or degradation is caused by conditions such as changes in temperature or pH.

As disclosed herein, other changes or alterations in a peptides or protein fragment can also result in activation including, for example, conformational change, post-translational modification, a change in primary, secondary, tertiary and/or quaternary structure, release from the matrix, release from a binding protein, etc. Such changes can also occur specifically by contact with a specific enzyme or chemical, or non-specifically from changes in temperature or pH.

A bone matrix composition may be exposed to any of the enzymes, e.g., proteases described herein (and others) at a range of different concentrations, e.g., between 1 pg/ml-100 ug/ml. For example, a protease can be used at between 1 pg/ml-100 pg/ml, between 100 pg/ml and 1 ng/ml, between 1 ng/ml and 100 ng/ml, between 100 ng/ml and 1 ug/ml, between 100 ug/ml and 100 ug/ml, etc. A variety of different digestion buffers may be used (see, e.g., non-limiting examples in the table in Example 11). The time of digestion can vary according to the protease, amount of DBM, and desired degree of digestion. In general, suitable times range between 30 minutes to 72 hours, e.g., between 30 minutes to 1 hour, between 1 and 12 hours, between 12 and 24 hours, between 24 and 48 hours, between 48 and 72 hours, etc. It will be appreciated that these times are approximate. Determination of the optimal treatment times for any preparation may involve assay of the treated tissue preparation in one of the biological activity assays described herein or others known in the art.

The present invention provides bone and cartilage matrices along with kits and methods for preparing bone and cartilage matrices having an increased osteoinductive or chondrogenic activity, respectively, compared to matrices not exposed to a condition or treatment as described herein. In general, the invention provides methods of treating bone and cartilage matrices to activate inactive factors that are already present in the bone or cartilage matrix, to alter the physical structure of the matrix, to inactivate an inhibitor, etc.

III. Transcriptional and Post-Transcriptional Regulation of Bone or Cartilage Enhancing or Inhibiting Factors As discussed above in certain embodiments of the invention, cells migrate into the inventive bone or cartilage repair matrices after their implantation into the body. In certain embodiments of the invention cells (either autologous, allogeneic, or xenogeneic) are already present in the matrix prior to implantation, and additional cells may enter the matrix after implantation. In either case, certain of the cells preferably contribute to the development and/or strengthening of the matrix, e.g., via the deposition of new bone and/or cartilage components and/or the reorganization or remodeling of components already present in the matrix or newly synthesized. Other cells may contribute to development of blood vessels, etc.

As mentioned above, agents such as protein fragments, peptides, growth factors, hormones, etc., can influence the biological activity and/or functioning of these cells. It will also be appreciated that certain of the cells may themselves produce molecules such as proteins, hormones, growth factors, chemoattractants, cytokines, etc., that may influence either their own functional activity or that of other cells either in the matrix or elsewhere in the body. Among these molecules are various molecules that act positively to promote proper formation of bone or cartilage. These molecules include bone or cartilage growth factors or factors that inhibit the activity of inhibitors of bone or cartilage formation. Among these positively acting molecules are bone morphogenetic proteins such as BMP-2, BMP-3, BMP-4, BMP-5, BMP-6, BMP-7, BMP-8, BMP-9, BMP-10, BMP-11, BMP-12, and BMP-13, transforming growth factors (TGF) such as those from the TGF-β superfamily, e.g., TGF-β, osteogenic factors, vascularizing factors, macrophage colony stimulating factor (MCSF), insulin-like growth factor (e.g., IGF-1), angiogenic factors (e.g., vascular endothelial growth factor (e.g., VGEF), osteonectin, alpha-2-HS glycoprotein, osteocalcin, osteopontin, matrix GLA protein etc. For purposes of the present description, nucleic acids or proteins whose expression positively influences formation, development, or repair of bone or cartilage, such as bone or cartilage growth factors, will be referred to as bone/cartilage enhancing factors (BCEF). Cells may also produce negatively acting molecules, e.g., molecules whose presence interferes with or reduces proper formation of bone or cartilage. Certain cytokines may have this effect, including interleukins such as the interleukin-1 (IL-1) family of cytokines (e.g., IL-1α, IL-1β, IL-18, and IL-1ra) and various other bone growth inhibitors (e.g., epidermal growth factor, alpha-2-HS glycoprotein, heparin, noggin, chordin, and fetuin). For purposes of the present description, nucleic acids or proteins whose expression negatively influences formation or development of bone or cartilage will be referred to as bone/cartilage inhibitory factors (BCIF).

The inventors have recognized that by modulating the expression of certain BCEF and/or BCIF by cells within the matrix (or elsewhere in the body), it is possible to increase the osteoinductive, osteoconductive, and/or chondrogenic activity of a bone or cartilage repair matrix. Generally it will be desirable to increase expression of BCEF and/or decrease expression of BCIF although it may at times be desirable to decrease expression of BCEF and/or increase expression of BCIF. Accordingly, in certain embodiments of the invention the bone and cartilage repair matrices incorporate any of a variety of agents that influence the biological activity and/or functioning of cells by transcriptional or post-transcriptional regulation of the expression of BCEF and/or BCIF molecules such as those mentioned above.

IV. Bone and Cartilage Matrices and Matrix Compositions and Methods of Use Thereof A variety of tissue types may be subject to regeneration using matrix preparations of the present invention. Several non-limiting examples include cortical bone, cancellous bone, cortical-cancellous bone, cartilage, perichondrium, and perostium, etc. Those skilled in the art will appreciate that the shapes that the matrices of the present invention can take will vary depending on the defect they are meant to repair. Some exemplary matrices, described in detail below, include whole matrices, chips, fibers, powders particles, rods, strings, sheets, weaves, solids, cones, discs, wedges etc. Matrices of any tissue type or shape can be exposed to a biological of chemical agent or condition of the invention to increase the biological activity of the matrix. Furthermore, it will be appreciated that matrices of any tissue type or shape can be treated according to the inventive methods for increasing a biological activity described herein.

Demineralized bone matrix preparations have been used for many years in orthopaedic medicine to promote the formation of bone. For example, demineralized bone matrices have found use in the repair of fractures, congenital bone defects, iatrogenic bone defects, in the fusion of vertebrae, in joint replacement surgery, and in treating bone destruction due to underlying disease such as rheumatoid arthritis. Demineralized bone matrices are thought to promote bone formation in vivo by osteoconductive and osteoinductive processes. Osteoconduction occurs if the implanted material serves as a scaffold for the support of new bone growth. Osteoconduction is particularly significant when bone growth is desired across a large or "critical size" defect, across which bone healing would proceed only slowly or not at all. It is generally believed that the osteoconductive properties of demineralized bone matrix preparations are provided by the actual shape and coherence of the implant. Thus demineralized bone matrix compositions including entangled fibers tend to have superior osteoconductive properties as compared to less fibrous, more granular preparations. Stabilizing agents, which tend to preserve the shape and/or coherence of the demineralized bone matrix substituent, can lead to better bone forming properties.

Any of a variety of bone matrix preparations may be utilized in the practice of the present invention. In certain preferred embodiments demineralized bone matrix is used. Demineralized bone matrix prepared by any method may be employed including particulate or fiber-based preparations, mixtures of fiber and particulate preparations, fully or partially demineralized preparations, mixtures of fully and partially demineralized preparations, including surface demineralized preparations as described by Gertzman et al. (U.S. Pat. No. 6,326,018, issued Dec. 4, 2001; Reddi et al., *Proc. Natl. Acad. Sci. USA* (1972) 69:1601-1605; Lewandrowski et al., *Clin. Ortho. Rel. Res.*, (1995) 317:254-262; Lewandroski et al., *J. Biomed. Mater. Res.* (1996) 31:365-372; Lewandrowski et al. *Calcified Tiss. Int.*, (1997) 61:294-297; Lewandrowski et al., *J. Ortho. Res.* (1997) 15:748-756, incorporated herein by reference). Preferred demineralized bone matrix compositions are described by Dowd et al., U.S. Pat. No. 5,507,813, which is incorporated herein by reference. The DBM may be in the form of a section that substantially retains the shape of the original bone (or a portion thereof) from which it was derived.

In a one preferred demineralization procedure, the implant is subjected to an acid demineralization step followed by a defatting/disinfecting step. The implant is immersed in acid over time to effect demineralization. Acids that can be employed in this step include inorganic acids such as hydrochloric acid and as well as organic acids such as formic acid, acetic acid, peracetic acid, citric acid, propionic acid, etc. The depth of demineralization into the bone surface can be controlled by adjusting the treatment time, temperature of the demineralizing solution, concentration of the demineralizing solution, and agitation intensity during treatment.

The demineralized implant is rinsed with sterile water and/or buffered solution(s) to remove residual amounts of acid and thereby raise the pH. A preferred defatting/disinfectant solution is an aqueous solution of ethanol, the ethanol being a good solvent for lipids and the water being a good hydrophilic carrier to enable the solution to penetrate more deeply into the bone particles. The aqueous ethanol solution also disinfects the bone by killing vegetative microorganisms and viruses. Ordinarily, at least about 10 to 40 percent by weight of water (i.e., about 60 to 90 weight percent of defatting agent such as alcohol) should be present in the defatting disinfecting solution to produce optimal lipid removal and disinfection within the shortest period of time. The preferred concentration range of the defatting solution is from about 60 to about 85 weight percent alcohol and most preferably about 70 weight percent alcohol.

In addition to the demineralizing step, the bone is optionally subjected to a configuring step to form an implant. The configuring step can be employed using conventional equipment known to those skilled in the art to produce a wide variety of geometries, e.g., concave or convex surfaces, stepped surfaces, cylindrical dowels, wedges, blocks, screws, and the like. A surgically implantable material fabricated from elongated bone particles that have been demineralized, which may be shaped as a sheet, and processes for fabricating shaped materials from demineralized bone particles are disclosed in U.S. Pat. Nos. 5,507,813 and 6,436,138, respectively, the contents of which are incorporated by reference herein. Suitable sheets included those sold under the trade name Grafton® Flex, which must be wetted/hydrated prior to use in order to render them useful for implantation. Such sheets have recently been reported as effective in seeding human bone marrow stromal cells (BMSCs), which may be useful in the repair of large bone defects (see, e.g., Kasten, et al., "Comparison of Human Bone Marrow Stromal Cells Seeded on Calcium-Deficient Hydroxyapatite, Beta-tricalcium Phosphate and Demineralized Bone Matrix", *Biomaterials*, 24(15):2593-603, 2003). Also useful are demineralized bone and other matrix preparations comprising additives or carriers such as binders, fillers, plasticizers, wetting agents, surface active agents, biostatic acents, biocidal agents, and the like. Some exemplary additives and carriers include, polyhydroxyl compounds, polysaccharides, glycosaminoglycan proteins, nucleic acids, polymers, polaxomers, resins, clays, calcium salts, and/or derivatives thereof.

The bone used in creating the bone matrix may be obtained from any source of living or dead tissue. Often, it will be preferred that the source of bone be matched to the eventual recipient of the inventive composition. At a minimum, it is often desirable that the donor and recipient are of the same species, though even xenogenic sources are permitted. Thus for use in humans, it is generally preferred to use DBM derived at least in part from human bone. For example, the bone material may be at least 10%, 20%, 30%, 40%, 50%, 60%, 70%, 80%, 90% or more human bone material. In certain embodiments 100% of the bone material is human bone material.

Once a bone sample is obtained, it is milled, ground, pulverized, or otherwise reduced to particulate form. Following particulation, the demineralized bone matrix is treated to remove mineral from the bone. While hydrochloric acid is the industry-recognized demineralization agent of choice, the literature contains numerous reports of methods for preparing demineralized bone matrices (see, for example, Russell et al., *Orthopaedics* 22(5):524-531, May 1999; incorporated herein by reference). For the purposes of the present invention, any material that provides scaffolding containing active osteoinductive factors is considered demineralized bone matrix. The demineralized bone matrix may be prepared by methods known in the art or by other methods that can be developed by those of ordinary skill in the art without undue experimentation. In some instances, large fragments or even whole bone may be demineralized, and then particulated following demineralization. Demineralized bone prepared in this way is within the scope of the invention.

The matrix may be completely insoluble or may be slowly solubilized after implantation. Following implantation, preferred matrices resorb or degrade, remaining substantially intact for at least one to seven days, most preferably for two or four weeks or longer and often longer than 60 days. Bioactive agents may be endogenously present in the matrix as in the case of most demineralized bone, or they may be exogenously added to the matrix. Matrices may also comprise combinations of endogenous and exogenous bioactive agents.

The matrix may comprise a number of materials in combination, some or all of which may be in the form of fibers and/or particles (see, e.g., U.S. Ser. No. 10/271,140, filed Oct. 15, 2002, incorporated herein by reference). The matrix may comprise calcium phosphates, the preparation of which is well known to practitioners in the art (see, for example, Driessens et al. "Calcium phosphate bone cements" Wise, D. L., Ed. *Encyclopedic Handbook of Biomaterials and Bioengineering, Part B, Applications* New York: Marcel Decker; Elliott *Structure and Chemistry of the Apatites and Other Calcium Phosphates* Elsevier, Amsterdam, 1994; each of which is incorporated herein by reference). Calcium phosphate matrices include, but are not limited to, dicalcium phosphate dihydrate, monetite, tricalcium phospate, tetracalcium phosphate, hydroxyapatite, nanocrystalline hydroxyapatite, poorly crystalline hydroxyapatite, substituted hydroxyapatite, and calcium deficient hydroxyapatites.

As mentioned above, osteoinductive peptides and protein fragments can be generated and/or activated within a bone or cartilage matrix specifically (e.g., by digestion with a protease) or by application of non-specific conditions (e.g., temperature, pH, etc.). In one preferred embodiment, peptides and proteins fragments are generated or activated specifically by digestion with a particular protease. While not wishing to be bound by any theory, exemplary proteases that may increase a biological activity (e.g., osteoinductive activity) of a bone matrix either by generating peptides or protein fragments or by a different mechanism include, acid proteases, serine proteases, metalloproteases, cysteine proteases, glyconases, and glycosidases. Particularly useful proteases are those stable and effective in acidic conditions. It will be appreciated that the particular activity and efficacy of a protease will vary depending upon the reaction conditions employed during treatment of the bone matrix. It is thus important to select appropriate reaction conditions. A variety of different reaction conditions may be tested, e.g., using the in vitro and/or in vivo assays described herein, to identify optimum proteases and combinations thereof, and appropriate reaction conditions.

Growth factor binding proteins are specific regulatory factors that can play a major role in regulating the activity of peptides and protein fragments. Virtually every extracellular matrix growth factor is know to be associated with a binding protein that regulates its activity. Typical growth factor binding proteins include but are not limited to noggin, chrondin, follistatin, TGF-β binding protein, and insulin-like growth factor binding proteins. According to the invention, growth factor binding proteins can be used to regulate the activity of peptides and protein fragments having osteoinductive activity.

Cartilage is an avascular tissue composed of 5-10% by weight of living cells. There are three major types of cartilage in the body: hyaline, also known as articular cartilage; fibrocartilage; and elastic cartilage. Articular cartilage covers the epiphyses of the bone and, in synovial joints, lies within a fluid filled capsule. Articular cartilage is load-bearing tissue that distributes forces across joint surfaces, protects the more rigid underlying bone, and provides smooth articulation and bending of the joints during normal activities of daily living. Fibrocartilage composes the intervertebral discs separating the vertebrae of the spinal columns. Elastic cartilage is present in areas requiring extreme resilience, such as the tip of the nose.

The ability of cartilage to rapidly and reversibly change shape is attributable to a resilient and elastic matrix with a high content of highly soluble proteoglycans entrapped within collagen, an insoluble fiber network. Proteoglycans, collagen and other molecules present in the cartilage tissue are produced by mesenchymally-derived cartilage cells, the chondrocytes. Chondrocytes receive nutrients and dispose wastes by diffusion through the matrix and are believed to have limited mobility or ability to divide and regenerate damaged tissue.

Chondrocytes normally produce anti-angiogenesis factors. However, when large areas of cartilage are damaged, overgrowth by fibroblasts and neovascularization of the area may result in the formation of scar tissue or a callus instead of articular cartilage. A subsequent ingrowth of bone forming cells may result in calcium deposition in these areas, causing further deformation of the local area.

Subchondral bone supports the overlying articular cartilage and transmits load to and from cartilage, and therefore contributes to the structural and functional integrity of the cartilage. Some studies suggest restoration of subchondral bone in an osteochondral defect will create a beneficial mechanical environment for the remodeling of neo-cartilaginous tissue and its integration with the surrounding host cartilage. See Smith, et al., "Analysis of the Mechanical Environment in a Repairing Osteochondral Defect", Trans ORS, 47:442 (2001); Wayne, et al., "A u-p Finite Element Analysis of the Behaviors of a Repaired Cartilage Surface", Trans ORS, 37:75 (1991). However, most of the repair and implant strategies to treat an osteochondral defect to date utilize deformable materials that do not have sufficient osteo-conductivity and mechanical strength, which may compromise the results of the repair.

A variety of materials can be used as cartilage repair matrices, some of which include material obtained from autologous, allogenic, or xenogenic cartilage while others do not. Transfer of cartilage cells from healthy regions of the joint to diseased surfaces in order to restore joint function has also been attempted. In this context, cartilage cells or small regions of cartilage are placed in partial or full-thickness defects within the joint surface using an open surgical procedure. The cell construct is held in place by periosteal tissue that is sutured in place. However, implanting cells or resurfacing with autogenous or allograft cartilage in the absence of an organized extracellular matrix does not support normal weight bearing. In many cases, these grafts quickly become fibrillated and degrade. With any type of cartilage exchange, efficacy of repair will be greatly facilitated following restoration of an extra-cellular matrix structure of normal cartilage prior to use.

Other approaches for repairing cartilage seed cartilage cells on a collagen matrix that is subsequently implanted. For example, U.S. Pat. No. 6,080,194 describes a collagen template formed by combining a porous collagen sponge with a collagen membrane. Other methods involve implantation of cells. U.S. Pat. No. 5,786,217 describes methods and compositions for the ex vivo proliferation of cells and their implantation to repair articular cartilage defects; U.S. Pat. No. 5,206,023 discloses methods and compositions for treatment and repair of defects or lesions of the cartilage; and, U.S. Pat. No. 5,041,138 concerns neomorphogenesis of cartilage in vivo from cell culture for the growth and implantation of cartilaginous structures. However, these methods do not provide much physiological support to the implanted cells, and not much access to the natural blood supply, limiting these procedures to applications with respect to the size of the defect being treated and the amount of load bearing possible.

Different approaches have been performed to recruit progenitor cells or chondrocytes in an osteochondral or chondral defect, including penetration of subchondral bone in order to access mesenchymal stem cells (MSCs) in the bone marrow which have the potential to differentiate into cartilage and bone. Steadman, et al., "Microfracture: Surgical Technique and Rehabilitation to Treat Chondral Defects", Clin Orthop., 391 S:362-369 (2001). In addition, some factors in the body are believed to aid in the repair of cartilage. For example, it has been observed that transforming growth factors beta (TGF-b) have the capacity to recruit progenitor cells into a chondral defect from the synovium or elsewhere when TGF-b is loaded in the defect. Hunziker, et al., "Repair of Partial-Thickness Defects in Articular Cartilage: Cell Recruitment From the Synovial Membrane", J. Bone Joint Surg., 78-A: 721-733 (1996). However, technical problems associated with the application of growth factors as cartilage repair strategies include the uncertainty of the initial dosage and the timing of release of these extrinsic bioactive factors. Further, the interaction among multiple bioactors (growth factors, cytokines, transcription factors) in natural chondrogenic development is not well understood, which may be a contributing reason to the failure of using a single growth factor for therapeutic purposes.

U.S. Pat. Nos. 5,270,300 and 5,041,138 both describe a method for treating defects or lesions in cartilage which provides a matrix, possibly composed of collagen, with pores large enough to allow cell population, and which further contains growth factors or other factors (e.g. angiogenesis factors) appropriate for the type of tissue desired to be regenerated. U.S. Pat. Nos. 5,270,300 and 5,041,138 both teach the use of TGF-beta in the matrix as a proliferation and chemotactic agent at a lower concentration, and a subsequent release of the same factor at a higher concentration to induce differentiation of cartilage repair cells.

Alternative methods of treatment use "plugs" of viable cartilage from the edge joint that are implanted into the damaged areas. These have limited success, in that only small defects can be treated, and vascularization of the seeded plug is difficult.

One important deficiency in the prior methods is the lack of a means to induce high levels of cartilage expression in the cartilage cells at the site of implantation, and there is insufficient vascularization and angiogenesis of the implant. Accordingly, most of the proliferative cartilage cells die, resulting in poor repair of the defect.

In accordance with certain embodiments of the present invention, various agents are incorporated into a bone or cartilage matrix such as those described above, resulting in a matrix with improved osteogenic and/or chondrogenic activity. The incorporation of any peptides, protein fragments, proteases, and/or other molecules described herein into the inventive bone and cartilage matrix compositions, is generally accomplished by suspending the molecule or molecules of interest in an appropriately compatible buffer as will be known to those skilled in the art. This buffer may be mixed with lyophilized matrix in a relatively low liquid-to-solid volume ratio to form a slurry. The slurry is then lyophilized and used to prepare the desired formulations. One or more peptides, protein fragments, and/or proteases may also be combined with the bone or cartilage by soaking or immersing the bone or cartilage in a solution or dispersion of the desired bioactive agents. Alternatively or additionally, bioactive agents may be applied to the implant by spraying, dipping, soaking, etc. Any bioactive agent may be adsorbed to the bone or cartilage using such methods well known in the art.

As described herein, certain of the osteoinductive or chondrogenic factors found in a bone or cartilage matrix are in cryptic form and must be "activated" or "released" in order to be osteoinductive. The activation of osteoinductive factors may involve a conformational change, a post-translational modification, protein cleavage, a change in tertiary or quaternary structure, release from a binding protein, etc. In preferred embodiments, the factors are in a pre- or pro-form, which requires proteolytic cleavage to be active. The osteoinductive factors may also be associated with a binding protein or a protein of a bone or cartilage matrix. Proteolysis may also be involved in the activation or inactivation of a binding protein, which could result in activation of the osteoinductive peptide or protein fragment. Therefore, all treatments of a bone or cartilage matrix with any specific or non-specific condition may affect activation rates of osteoinductive peptides and protein fragments.

According to the present invention, the presence or activation of peptides and/or protein fragments having osteoinductive or chondrogenic activity may compensate for degradation of osteoinductive or chondrogenic proteins in the matrix, which may occur during preparation of the matrix. In certain preferred embodiments it is desirable to both inhibit the degradation of osteoinductive or chondrogenic factor and activate or add the osteoinductive or chondrogenic peptides or protein fragments of the invention. As previously mentioned, such factors as pH, ion concentration, or other factors which affect protein function and/or folding of the peptide or protein fragment may affect the activation of osteoinductive or chondrogenic factors found in bone or cartilage matrices. These factors also may affect the release of a factor from its binding protein. For example, where pH plays a role in the activation of a factor, the matrix composition may include a chemical compound such as a polymer which will break down over time and release an acid by-product; thereby, activating the factors within the matrix composition. Alternatively, a biodegradable polymer may release ions or a protease that is able to "activate" the osteoinductive factors of the matrix composition.

A variety of components or agents may be added to an improved bone or cartilage matrix in accordance with the present invention. A number of such components and agents are described below. For purposes of description, the components and agents are classified into various groups. However, this is not intended to place any limitation upon the purpose or function of the components and agents in the context of the inventive bone or cartilage matrices.

Osteoinducing Agents. Osteoinducing agents may be added in an activated or non-activated form. These agents may be added at anytime during the preparation of the inventive material. For example, in a demineralized bone matrix, the osteoinducing agent may be added after the demineralization step and prior to the addition of any stabilizing agents. In certain embodiments, the demineralized bone matrix is lyophilized in a solution containing the osteoinducing agent. In other embodiments, the osteoinducing agents are adhered onto a hydrated demineralized bone matrix and are not freely soluble. In other instances, the osteoinducing agent is added to a demineralized bone matrix after addition of any stabilizing agent so that the osteoinducing agent is available immediately upon implantation.

Osteoinducing agents include any agent that leads to or enhances the formation of bone. The osteoinducing agent may do this in any manner, for example, the agent may lead to the recruitment of cells responsible for bone formation, the agent may lead to the secretion of matrix which may subsequently undergo mineralization, the agent may lead to the decreased resorption of bone, etc. Particularly preferred osteoinducing agents include certain bone morphogenic proteins (BMPs) such as BMP-2, transforming growth factor (TGF-β), insulin-like growth factor (IGF-1), and angiogenic factors such as VEGF. In one preferred embodiment (see U.S. Ser. No. 10/271,140, filed Oct. 15, 2002, incorporated herein by reference), the osteoinducing agent is genetically engineered to comprise an amino acid sequence, which promotes the binding of the inducing agent to the demineralized bone matrix or the carrier. Sebald et al. in PCT/EP00/00637, incorporated herein by reference, describe the production of exemplary engineered growth factors, suitable for use with demineralized bone matrices.

Those skilled in the art will readily appreciate that the same principles can be applied to cartilage repair matrices. Chondrogenic agents include any agent that leads to or enhances the formation of cartilage. The chondrogenic agents may do this in any manner, for example, the agent may lead to the recruitment of cells responsible for cartilage formation, the agent may lead to the secretion of matrix, the agent may lead to the resorption of cartilage.

Carriers, Diffusion Barriers, and Stabilizing Agents. In certain embodiments of the invention one or more additional components is added to an improved bone or cartilage matrix, e.g., a DBM matrix. Among these additional components are any of a variety of agents that act as carriers, excipients, stabilizers, and/or diffusion barriers. In general, these additional components will be added to improve handling, wettability, or other physical aspects of the implant device. The additional materials may also serve to further augment the biological activity of the implant. Preferred carriers include hydroxylated and polyhydroxylated compounds as described in U.S. Pat. No. 5,073,373. As indicated therein, suitable carriers for the bone powder include liquid polyhydroxy compounds and their esters, polysaccharides, surface active agents, etc. Polyhydroxy compounds are preferred in certain embodiments of the invention. The preferred class of polyhydroxy compounds possesses up to about 12 carbon atoms and where their esters are concerned, are preferably the monoesters and diesters. Specific polyhydroxy compounds of the foregoing type include glycerol and its monoesters and diesters derived from low molecular weight carboxylic acids, e.g., monoacetin and diacetin (respectively, glycerol monoacetate and glycerol diacetate), ethylene glycol, diethylene glycol, triethylene glycol, 1,2-propanediol, trimethylolethane, trimethylolpropane, pentaerythritol, sorbitol, and the like. Of these, glycerol is especially preferred as it exhibits a particularly pronounced capability for dissolving osteogenic proteins present in the bone powder and enhancing the availability of these proteins at the bone repair site. Mixtures of the afore-discussed polyhydroxy compounds or esters, e.g., sorbitol dissolved in glycerol, glycerol combined with monoacetin and/or diacetin, etc., are also useful.

In other instances, certain of the DBM compositions comprise a polymer, which may perform any of the foregoing functions. Preferably, the polymer is metabolized over time, so that osteoinductive agents are unmasked and/or released from the DBM composition over time, or retarded in their degradation rate. Diffusion barriers of the invention may also work through alternative means by decreasing the diffusion of the activating enzymes to the factors present in the DBM composition. Preferably, such unmasking, release, controlled release, or controlled degradation occurs over a period longer than several hours, preferably longer than a day to several days, and possibly lasting weeks or even months. In certain preferred embodiments, the rates of degradation, release, and activation are balanced to yield a DBM composition with the desired level of osteoinductivity over time. Inventive compositions containing a diffusion barrier or stabilizing agent typically show osteoinductive activity for longer periods of time than is seen with comparable compositions lacking the stabilizing agent or diffusion barrier.

In some embodiments of the invention, the additional agent comprises a biodegradable polymer (e.g., that may inhibit or delay diffusion of osteoinductive agents out of the DBM composition, and/or block access of degrading and/or activating enzymes to the osteoinductive agents). Enzymes retarded in their diffusion to the included DBM may be capable of releasing the active factor from the matrix, and/or degrading or inactivating the active factor. They also may act by retarding diffusion of the active factors from the implant site. In these ways, the barriers provide for longer residence time of the active factors at the implant site. This is particularly useful for forming bone in higher species such as humans, where bone formation appears to require the presence of active factors for longer times.

Generally, the additional materials most suitable to serve as carriers, excipients, etc., will be easily mixed with DBM or synthetic matrix of choice to form a gel, paste, or putty-like consistency, although in some embodiments, the barrier/matrix formulation will be prepared as a relatively non-deformable solid (e.g., for matrix preparations to be used in posterior lateral spine fusion). In preferred embodiments, additional materials themselves degrade in a predictable manner. Resorbable polymers with known hydrolytic rates are useful as well as enzymatically degraded polymers. Particularly useful are lipase susceptible lipid based carriers such as fatty acids and phospholipids, which mix well with DBM. In certain DBM embodiments, the composition does not include phosphatidylcholine. Some particularly effective preparations provide prolonged stability by controlled unmasking of the osteoinductive factors. These preparations generally involve the use of two or more diffusion barriers with different degradation times affording at least two different rates of unmasking the same active factor.

Biodegradable polymers useful as carriers, excipients, etc., in preparing inventive stabilized matrix/growth factor compositions include natural polymers such as proteins (e.g., collagen) and polysaccharides (e.g., starch, modified starch, maltrin) as well as man-made resorbable polymers such as poly-orthoesters. These polymers when mixed with the inventive growth factor containing compositions retard diffusion of the host's degradative enzymes and/or water to the active factors contained within the composition, thereby retarding release and/or degrading of the active factor contained therein.

Polymers that may be included within inventive compositions include, for example, natural polymers such as lipids, polysaccharides, proteoglycans, and proteins. Preferred polysaccharides include starches, dextrans, and celluloses, and preferred proteins include collagen. Polysaccharides such as starches, dextrans, and celluloses may be unmodified or may be modified physically or chemically to affect one or more of their properties such as their characteristics in the hydrated state, their solubility, their susceptibility to degradation, or their half-life in vivo. Polysaccharides such as starches and celluloses are attractive as they also have known degradation rates. Generally, the celluloses degrade more slowly within the body, breaking down on the order of weeks or months, while many starch and lipid preparations degrade rapidly, on the order of hours or days. Starch in the natural state is a mixture of two polysaccharides, amylose and amylopectin. The susceptibility of the particular starch to the starch-degrading enzymes such as amylase, pectinases, and β-glucosidase is an important consideration in designing the inventive formulations. Those skilled in the art are aware of the variety of amylase susceptibilities of starches prepared from various plant sources and may apply this knowledge to produce formulations having a desired stability time. Preferred starches will degrade as much as 10% per day, preferably 50% per day, and most preferably greater than 90% per day. Those starches less susceptible to degradation by pectinase and/or amylase (amylase-resistant starch; Starch Australasia, Sydney, Australia) may be used to maximally extend the osteoinductive half-life in vivo to an even greater extent than improved DBM or synthetic growth factor/matrix formulations prepared from more enzyme susceptible starches. Some modified starches are less susceptible to degradation by amylase; therefore, improved DBM with modified starch would presumably have a longer half-life in vivo as compared to those improved DBM with unmodified starch. One preferred method to affect amylase susceptibility of starch is through the use of starch lipid combinations. Guidance for the combination of lipid and starch to affect amylase susceptibility is given by Crowe et al. "Inhibition of Enzymic Digestion of Amylose by Free Fatty Acids In Vitro Contributes to Resistant Starch Formation" *J. Nutr.* 130(8):2006-2008, August 2000; incorporated herein by reference. Similar considerations apply to lipids and their degradative enzymes the lipases. A large variety of mono-, di-, and triglycerides with varying degrees of susceptibility to lipase degradation are available from commercial sources. Some embodiments include one or more polymeric materials, preferably biodegradable, such as tyrosine polycarbonates, polyfumarates, tyrosine polyarylates, and poly-orthoesters such as polylactide, polygalactide, and co-polymers thereof. These polymers are biodegradable, and their properties can be modified by altering the chain length or degree of cross-linking of the polymer and/or the chemical structure of the monomers. Additionally, co-polymers can be prepared using combinations of resorbable polymers.

Water Removal. Following preparation of the inventive DBM composition, the composition may be stored in its hydrated form or in a lyophilized form with the endogenous water removed. The composition may contain from about 10% to about 99% water by weight. A lyophilized composition may have 50%, 60%, 70%, 80%, 90%, 95%, or 98% of the water removed from the original sample. In certain preferred embodiments, the water content is >10% by weight. The composition may be stored at or below room temperature to further increase the self-life of the inventive DBM composition. As would be appreciated by one of skill in this art, decreasing the temperature will increase the half-life of the osteoinductivity of the inventive DBM composition.

In certain embodiments of the invention the bone matrix composition comprises an excipient such as glycerol, which may act as a water substitute. Additional information regarding suitable water substitutes is found below and in U.S. Provisional Patent Application Ser. No. 60/539,555, filed Jan. 27, 2004.

Other Water Substitutes. Other agents know to decrease the activity of water or increase the viscosity of the water in DBM compositions may also be used to stabilize DBM compositions. For example, decreasing the water content in DBM compositions by lyophilization causes the viscosity of the remaining fluid to increase, thereby, slowing down diffusion of protease and osteoinductive agents in the DBM compositions. The increased viscosity of fluid in the DBM compositions can be also be accomplished by the addition water substitutes to the DBM compositions. Water substitutes may also inhibit chemical reactions in which water participates, or water is the required medium for the reaction. Water substitutes may include polyols such as glycerol, hydrophilic polymers, polyethylene glycol, hydrogels, hyaluronic acid, lipids, hydroxylated small molecules, DMSO, DMF, oils, emulsions of oil and water, emulsions of oil and degassed water, polysaccharides, etc. Preferably, the water substitutes are biocompatible. Without wishing to be bound by any particular theory, these water substitutes likely act to stabilize DBM compositions by decreasing the diffusion of osteoinductive agents to the enzymes that will degrade them. Water substitutes may also inhibit chemical reactions in which water participates or is the required medium for the reaction. Therefore, even at room temperature the resulting DBM compositions with water substitutes have a greater shelf-life than DBM compositions without water substitutes. The effect of water substitutes may be further increased by storing the DBM compositions at lower temperatures. Other stabilizing agents and/or other methods of stabilizing DBM compositions (e.g., lowering pH) may also be used in conjunction with water substitutes.

Examples of water substitutes include hydrogenated castor oil, bone marrow lipids, hydrogenated beef tallow, hydrogenated lard oil, cacao butter, fatty acid glycerol esters such as glycerol monolaurate, glycerol monomyristate, glycerol monopalmitate, glycerol monostearate, glycerol dilaurate, glycerol dimyristate, glycerol dipalmitate, glycerol distearate, glycerol trimyristate, glycerol tripalmitate, and glycerol tristearate. Examples of waxy materials that may be used as water substitutes include beeswax, carnauba wax, Japan wax, spermaceti, hydrocarbons such as paraffin, micro-crystalline wax, and fatty alcohols such as cetyl alcohol, and stearyl alcohol as well as higher fatty acids such as lauric acid, myristic acid, palmitic acid, stearic acid, behenic acid, and arachidic acid.

The addition of water substitutes to a composition also has the benefit of making the composition flowable and moldable.

Addition of Stabilizing Agents and Water Substitutes. The incorporation of stabilizing agents into the inventive formulations is generally accomplished by suspending the molecule or molecules of interest in an appropriately compatible buffer as will be known to those skilled in the art. This buffer is then mixed with matrix in a relatively low liquid-to-solid volume ratio to form a slurry. In certain embodiments, the buffer with the stabilizing agent(s) is mixed with lyophilized matrix. The slurry may then be lyophilized and used to prepare the desired DBM formulations.

Covalent Modification of DBM. The DBM may be covalently modified by the addition of polyethylene glycol or silylation.

Formulations and Preparations of Bone Matrix Compositions. Improved osteogenic and chondrogenic matrix compositions of the present invention may be adapted or formed for a particular use. The composition may be used to alter the physical, biological, or chemical properties of a bone or cartilage graft preparation. A physician would readily be able to determine the form needed for a particular application taking into account such factors as the type of injury, the site of injury, the patient's health, the risk of infection, etc.

Inventive compositions therefore may be prepared to have selected osteoinductivity or chondrogenic activity rates, or even to have different rates in different portions of an implant. In certain embodiments, an inventive formulation may include a mixture of active peptides or protein fragments, each with a different half-life. Such a mixture could extend the period of osteoinductivity or chondrogenic activity in the composition. The density distribution and/or type distribution of the peptides can be varied to selectively control properties such as the rate of remodeling and resorption of an implant.

In certain preferred embodiments of the invention, 1 cm$^3$ of compositions such as this can be formulated to stimulate bone growth in a human patient comparable to the bone growth induced by treatment with 0.1-10 ug of rhBMP-2 (recombinant human BMP-2) on a 1 cm$^3$ collagen sponge, and preferably comparable to 10-100 ug, and most preferably comparable to 0.1-100 mg rhBMP-2 on such a sponge. The effect on bone growth of these compositions can be compared to that of rhBMP-2 or other growth factors in an athymic rat model assay according to the method of Edwards et al. ("Osteoinduction of Human Demineralized Bone: Characterization in a Rat Model" Clinical Orthopeadics & Rel. Res., 357:219-228, December 1998) or using other accepted models.

Physical properties such as deformability and viscosity of the matrix may also be chosen depending on the particular clinical application. Those skilled in the art will appreciate that the particles of the bone matrix or cartilage may be mixed with materials and factors to improve other characteristics of the implant. For example, the improved matrix material may be mixed with other agents to improve wound healing. These agents may include drugs such as antibiotics and/or anti-inflammatory agents, proteins, peptides, polynucleotides, solvents, chemical compounds, and/or biological molecules.

The matrices (or other inventive bone or cartilage material) may also be formed into various shapes and configurations. As mentioned above, the matrices can, for example, be formed into rods, strings, sheets, weaves, solids, cones, discs, fibers, wedges etc. In certain embodiments, the shape and size of the particles in the bone or cartilage matrix composition affects the time course of osteoinductivity. For example, due to degradation of the bone or cartilage matrix material and diffusion rates of associated factors in vivo, with a cone or wedge shape, the tapered end may have osteoinductivity shortly after implantation of the matrix composition, whereas the thicker end may have activity later in the healing process (e.g., hours to days to weeks later). Also, a larger particle size may induce bone formation over a longer time course than smaller particles. Particles of different characteristics (e.g., composition, size, shape) may be used in the formation of these different shapes and configurations. For example, in a sheet of demineralized bone matrix, a layer of long half-life particles may be alternated between layers of shorter half-life particles (See U.S. Pat. No. 5,899,939, incorporated herein by reference). In a weave, strands composed of short half-life particles may be woven together with strands of longer half-lives.

In one preferred embodiment of the invention, fibrous demineralized bone matrix is shaped into a form as described in U.S. Pat. No. 5,507,813 and U.S. Ser. No. 10/271,140, filed Oct. 15, 2002, incorporated herein by reference. The shaped matrix is then embedded within a diffusion barrier type matrix, such that a portion of the matrix is left exposed free of the matrix material. The matrix is treated as described herein either before or after shaping. Devices prepared in this way from these matrices have a combination of immediate and longer lasting osteoinductive properties and are particularly useful in promoting bone mass formation in human postero-lateral spine fusion indications.

In another embodiment of the invention, demineralized bone matrix compositions have a pre-selected three-dimensional shape prepared by repeated application of individual layers of DBM, for example by 3-D printing as described by Cima et al. U.S. Pat. Nos. 5,490,962; and 5,518,680, each of which is incorporated herein by reference; and Sachs et al. U.S. Pat. No. 5,807,437, incorporated herein by reference. Different layers may include individual stabilized demineralized bone matrix preparations, or alternatively may include DBM layers treated with stabilizing agents after deposition of multiple layers. The matrix is treated as described herein either before or after shaping.

In the process of preparing improved inventive bone and cartilage matrix materials, the materials may be produced entirely aseptically or be sterilized to eliminate any infectious agents such as HIV, hepatitis B, or hepatitis C. The sterilization may be accomplished using antibiotics, irradiation, chemical sterilization (e.g., ethylene oxide), or thermal sterilization. Other methods known in the art of preparing bone and cartilage matrices, such as defatting, sonication, and lyophilization may also be used in preparing the improved matrix. Since the biological activity of various materials including demineralized bone is known to be detrimentally affected by most terminal sterilization processes, care must be taken when sterilizing the inventive compositions. In preferred embodiments, the matrix compositions described herein will be prepared aseptically or sterilized, see, e.g., U.S. Ser. No. 10/271,140, filed Oct. 15, 2002.

In addition to therapeutic uses involving implantation into a subject, the improved bone and cartilage matrices of the invention have a number of other uses. For example, they can be used to generate cell lines, tissues, or organs having osteogenic or chondrogenic properties. In particular, cells can be removed from a donor and cultured in the presence of an inventive composition. The invention includes such cells as well as tissues and organs derived therefrom. The cells, tissues, or organs may be implanted into the original donor after a period of culture in vitro or may be implanted into a different subject.

While not wishing to be bound by any theory, the improved bone matrices and compositions may more closely resemble the native environment that exists within developing, healing, or normal bone than alternative compositions. They may be useful as research reagents, e.g., as tissue culture systems in which to study the differentiation or other properties of mesenchymal cells. The invention thus includes kits for research use, which include one or more of the inventive matrices. The kits may also include cells, control matrices, growth or differentiation factors, media, instructions, etc.

V. Assays for Osteogenic, Osteoconductive, and Chondrogenic Activity

Bone formation may be tested in by various methods accepted in the art, for example, in athymic rats using the method of Edwards et al. ("Osteoinduction of Human Demineralized Bone: Characterization in a Rat Model" *Clinical Orthopeadics & Rel. Res.,* 357:219-228, December 1998; incorporated herein by reference). In other instances, osteoinduction is considered to occur through cellular recruitment and induction of the recruited cells to an osteogenic phenotype. Osteoinductivity may also be determined in tissue culture, e.g., as the ability to induce an osteogenic phenotype in culture cells (primary, secondary, cell lines or explants).

The invention provides tissue culture assays useful for assessing the ability of a treatment or condition to increase the ostegenic activity of a bone matrix, e.g., a DBM matrix (see Examples 10 and 11. The matrix is exposed to a treatment or condition, e.g., any of the treatments and/or conditions described herein, or combinations thereof. Cells are then exposed to the bone matrix, e.g., by adding the matrix to a tissue culture vessel containing the cells, by plating the cells on a matrix surface, etc. The exposure can continue for any suitable time period, e.g., minutes, hours, days, etc. The assay comprises testing the ability of the cell to (i) express a marker indicative of differentiation along a lineage typical of bone and/or cartilage-forming cells, e.g., an osteoblast, osteocyte, chondroblast, and/or chondrocyte lineage; and/or (ii) display a morphological characteristic indicative of differentiation along a lineage typical of bone and/or cartilage-forming cells, e.g., an osteoblast, osteocyte, chondroblast, and/or chondrocyte lineage; and/or (iii) fail to express a marker characteristic of a lineage other than a lineage typical of bone and/or cartilage-forming cells under conditions in which such expression would otherwise be observed; and/or (iv) fail to display a morphological characteristic indicative of differentiation along a lineage other than a lineage typical of bone and/or cartilage-forming cells. Cell phenotype and/or marker expression can be assessed in the presence or absence of the matrix and can be assessed at any time following exposure of the cells to the matrix.

Suitable cells for performing the inventive assay include, e.g., mesenchymal stem cells, mesenchymal cells, preosteoblastic cells, etc. As is known in the art, undifferentiated mesenchymal cells are able to differentiate along osteoblastic, chondrocyte, adipocyte, or myocyte pathways to form osteoblasts, chondrocytes, adipocytes, or myocytes. In general, mesenchymal cells suitable for use in the assay can be any cell line that is capable of differentiating along an osteoblast or chondrocyte lineage under appropriate conditions, e.g., when exposed to the appropriate growth factor(s), serum, etc. For example, preferred cells for use in the assay express osteoblast or chondroblast markers when exposed to osteoinductive growth factors. Preferably relatively undifferentiated mesenchymal cells are used. Cell lines (preferably clonal cell lines) or primary cells can be used. Primary cells are non-immortalized cell lines that are recovered directly from an animal and grown for a limited number of passages. The cells may be from any species, e.g., rodent (such as murine, rat, etc.), primate (such as monkey or human), dog, etc. In certain embodiments of the invention the cells are selected from the group consisting of W20-17, C2C12, C3H10T1/2, MC3T3-E1, RCJ, 2T3, and ST2 cells. Suitable cell lines are widely available among those of skill in the art. A number of suitable cell lines can be obtained from depositories such as the America Type Culture Collection (ATCC), Manassas, Va., 20108.

The treatment or condition may result in increased expression and/or synthesis of a marker characteristic of bone and/or cartilage forming cells. Suitable markers whose expression can be measured include, but are not limited to, alkaline phosphatase, Osterix, Cbfa-1 (core binding factor 1), dlx-5 (distal-less homeobox 5), MSX2, osteopontin, bone sialoprotein, osteocalcin, osteoblast specific factor 1, RANK ligand, Osteoprotegrin, Collagen Type I, etc. Any suitable measurement method can be used to measure expression of the marker, e.g., assaying an enzymatic reaction, immunological detection of protein, measuring mRNA levels, etc. The measurement can be qualitative (e.g., whether the marker is or is not detectable), semi-quantitative (e.g., +, ++, +++, with the number of + symbols correlating to the expression level), or quantitative (numerical).

The treatment or condition may cause the cells to display a morphological characteristic typical of bone and/or cartilage-forming cells, e.g., a rounded morphology (as opposed to elongated or fiber-shaped), which can also be assessed on a qualitative, semi-quantitative, or quantitative basis. The treatment or condition may cause the cells to fail to develop a morphological characteristic of a myogenic lineage such as the formation of myotubes and/or may cause the cells to fail to express one or more markers indicative of differentiation along a lineage other than a lineage typical of bone and/or cartilage-forming cells. For example, if the cells would normally express a marker such as MyoD, myogenin, Myf5, muscle-specific myosin, etc., or any of a number of related or different proteins characteristic of muscle cells or precursors thereof, but do not express the marker when exposed to the treatment or condition, the failure to express the marker may indicate that contact with the matrix induced the cells to differentiate along a lineage typical of bone and/or cartilage-forming cells rather than a myogenic lineage.

In any of the inventive assays, a variety of controls can be performed, i.e., the effect of a matrix that has been exposed to a treatment or condition can be compared with the effect of a control matrix. For example, the effect on cells of a matrix that has been exposed to the activity-enhancing treatment or condition can be compared with the effect of a comparable matrix (e.g., a matrix of essentially identical composition) that has not been exposed to the treatment or condition. The control matrix can be an "inactivated" matrix, e.g., a matrix that has been exposed to a condition that denatures endogenous growth and differentiation factors. The inactivating treatment may be, for example, exposure to a chaotropic agent such as guanidinium HCl, guanidinium isothyocyanate, exposure to extremes of heat, etc. Appropriate concentrations and time periods should be used to cause inactivation. Comparisons with cells that are not exposed to any matrix or that are exposed to any of a variety of other matrices, bioactive agents, etc., can be performed.

Assays can be performed using cells of any species. Tissue explants can also be used.

In certain embodiments of the invention an improved bone matrix composition, e.g., a DBM composition derived from human bone, induces expression of an osteoblastic marker such as alkaline phosphatase to a level at least 2-fold as great as that induced by BMP-2. The matrix may induce expression of an osteoblastic marker at a level approximately 10-fold as great as that induced by 15% fetal bovine serum (FBS). The matrix may induce expression of an osteoblastic marker at a level approximately 900-fold as great as that induced by 5% FBS. It will be appreciated that different treatment times and amounts will result in different degrees of effect. For example, the effect may be between 2 and 4-fold, between 5 and 10-fold, between 10 and 50-fold, between 10 and 100-fold, between 100 and 500-fold, between 500 and 1000-fold, or any intermediate range.

If desired, the tissue culture method can be correlated with an in vivo ectopic bone formation assay, e.g., as described by Zhang et al. ("A quantitative assessment of osteoinductivity of human demineralized bone matrix" *J. Periodontol.* 68(11): 1076-84, November 1997; incorporated herein by reference). Calibration of the in vitro assays against a proven in vivo ectopic bone formation model may be used to confirm that the ability of a compound to induce an apparent "osteogenic" phenotype in tissue culture is correlated with the induction of new bone formation in vivo. Certain BMPs, IGF, TGF-β, and various angiogenic factors are among the osteoinductive factors found to recruit cells from the marrow or perivascular space to the site of injury and then cause the differentiation of these recruited cells down a pathway responsible for bone formation. For example, DBM isolated from either bone or dentin have been found to be osteoinductive materials (Ray et al., "Bone implants" *J. Bone Joint Surgery* 39A: 1119, 1957; Urist, "Bone: formation by autoinduction" *Science* 150:893, 1965; each of which is incorporated herein by reference).

Osteoinductivity score refers to a score ranging from 0 to 4 as determined according to the method of Edwards et al.

(1998), supra, or an equivalent calibrated test. In the method of Edwards et al., a score of "0" represents no new bone formation; "1" represents 1%-25% of implant involved in new bone formation; "2" represents 26-50% of implant involved in new bone formation; "3" represents 51%-75% of implant involved in new bone formation; and "4" represents >75% of implant involved in new bone formation. In most instances, the score is assessed 28 days after implantation. However, the osteoinductivity score may be obtained at earlier time points such as 7, 14, or 21 days following implantation. In these instances it is important to include a normal control such as matrix powder without a carrier, and if possible, a positive control such as BMP. Occasionally osteoinductivity may also be scored at later time points such as 40, 60, or even 100 days following implantation. Percentage of osteoinductivity refers to an osteoinductivity score at a given time point expressed as a percentage of activity, of a specified reference score. Results of tests in animal models can be correlated with effects in human patients, and a comparable osteoinductivity score can be derived. A number of methods by which cartilage repair/growth can be assessed are known in the art. For example, morphological criteria (histology), compressive strength, biochemical composition, and imaging studies (e.g. MRI), have all proven useful in measuring cartilage repair/growth. (See, e.g., Hidaka C, et al., J Orthop Res. 2003 July; 21(4):573-83; Roberts S Arthritis Res Ther. 2003; 5(1):R60-73. Epub 2002 Nov. 13, etc., Kavalkovich, K., et al., "Chondrogenic activity of mesenchymal stem cells compared to articular chondrocytes", poster presented at the 47$^{th}$ Annual Meeting, Orthopaedic Research Society, February 25-28, San Francisco, Calif. (published in J. Bone Joint Surgery), Huang, W., et al., Proc. Natl. Acad. Sci., 98(1): 160-165, 2001 for examples.) According to one chondrogenic assay, chondrogenic media with 10 ng/ml TGF-β3, 40 µg/ml proline, 100 µg/ml pyruvate and 50 mg/ml ITS (insulin, transferrin and selenious acid) is added to the pellet culture, for a period of time, e.g., 21 days. Chondrocytic phenotype is assessed using safranin-O and H&E stainings and/or by measuring the expression of Type II and/or Type X collagen. The ability of any of the inventive compositions to achieve comparable results may be tested.

In certain embodiments of the invention the improved bone or cartilage matrix composition preferably produce bone or cartilage in an animal model and/or in human patients with similar timing and at a level at least 10%, 20%, 35%, 50%, 100%, 200%, 300%, or 400% or greater osteogenic, osteoinductive or chondrogenic activity than a bone or cartilage matrix that has not been exposed to a treatment or condition as described herein. Of course, one skilled in the art will appreciate that these values may vary slightly depending on the type of test used to measure the osteoinductivity or osteogenic or chondrogenic activity described above. According to the present invention, the test results may fall within the range of 10% to 35%, 35% to 50%, 50% to 100%, 100% to 200%, and 200% to 400%. In certain preferred embodiments, when a bone matrix composition is implanted into a bone defect site, such as a fracture, a congenital bone defect, an iatrogenic bone defect, a vertebral fusion, or a site of bone destruction due to underlying disease such as rheumatoid arthritis, the bone matrix composition has an osteoinductivity score of at least 1, 2, 3, or 4 in an animal model and/or in humans.

VI. Therapeutic Applications

Improved osteogenic and chondrogenic compositions of the present invention may be used to promote the healing of bone and cartilage injuries. The compositions may be used in any bone or cartilage of the body and on any type of injury. For example, specific bones that can be repaired using the inventive material include the ethmoid, frontal, nasal, occipital, parietal, temporal, mandible, maxilla, zygomatic, incus, stapes, malleus, cervical vertebrae, thoracic vertebrae, lumbar vertebrae, sacrum, sternum, ribs, clavicle, scapula, humerus, ulna, radius, carpal bones, metacarpal bones, phalanges, ileum, ischium, pubis, pelvis, femur, patella, tibia, fibula, calcaneus, talus, and metatarsal bones. Cartilage at any location within the body can be repaired, including both articular and non-articular cartilage. For example, cartilage in joints such as the knee, shoulder, hip, etc., can be repaired as can cartilage within the nose, in the spine, etc. The type of injury amenable to treatment with the improved matrices include bone or cartilage defects resulting from injury, brought about during the course of surgery, infection, malignancy, or developmental malformation. The inventive material may be useful in orthopaedic, neurosurgical, cosmetic, and oral and maxillofacial surgical procedures such as the repair of simple and compound fractures and non-unions, external and internal fixations, joint reconstructions such as arthrodesis, general arthroplasty, cup arthroplasty of the hip, femoral and humeral head replacement, femoral head surface replacement and total joint replacement, repairs of the vertebral column including spinal fusion and internal fixation, tumor surgery (e.g., deficit filling), discectomy, laminectomy, excision of spinal cord tumors, anterior cervical and thoracic operations, repair of spinal injuries, scoliosis, lordosis and kyphosis treatments, intermaxillary fixation of fractures, mentoplasty, temporomandibular joint replacement, alveolar ridge augmentation and reconstruction, inlay bone grafts, implant placement and revision, sinus lifts, etc.

In related embodiments, the compositions of the invention are particularly preferred for delivering osteoinductive or chondrogenic growth factors to the site of the bone or cartilage injury. Other preferred agents to be included in the bone or cartilage matrix for delivery include factors or agents that promote wound healing. However, inventive compositions may alternatively or additionally be used to deliver other pharmaceutical agents including antibiotics, anti-neoplastic agents, growth factors, hematopoietic factors, nutrients, etc. Bioactive agents that can be delivered using the inventive bone or cartilage matrix composition include non-collagenous proteins such as osteopontin, osteonectin, bone sialo proteins, fibronectin, laminin, fibrinogen, vitronectin, thrombospondin, proteoglycans, decorin, proteoglycans, beta-glycan, biglycan, aggrecan, veriscan, tenascin, matrix GLA protein hyaluronan; cells; amino acids; peptides; inorganic elements; inorganic compounds; organometallic compounds; cofactors for protein synthesis; cofactors for enzymes; vitamins; hormones; soluble and insoluble components of the immune system; soluble and insoluble receptors including truncated forms; soluble, insoluble, and cell surface bound ligands including truncated forms; chemokines, interleukins; antigens; bioactive compounds that are endocytosed; tissue or tissue fragments; endocrine tissue; enzymes such as collagenase, peptidases, oxidases, etc.; polymeric cell scaffolds with parenchymal cells; angiogenic drugs, polymeric carriers containing bioactive agents; encapsulated bioactive agents; bioactive agents in time-release form; collagen lattices; antigenic agents; cytoskeletal agents; cartilage fragments; living cells such as chondrocytes, osteoblasts, osteoclasts, fibroblasts, bone marrow cells, mesenchymal stem cells, etc.; tissue transplants; bioadhesives; bone morphogenic proteins (BMPs), transforming growth factor (TGF-β), insulin-like growth factor (IGF-1, IGF-2), platelet derived growth factor (PDGF); fibroblast growth factors (FGF), vascular endothelial growth factor (VEGF), epidermal growth factor (EGF), growth factor binding proteins, e.g., insulin-like growth factor binding protein (IGFBP-2, IGFBP-3, IGFBP-4, IGFBP-5, IGFBP-6); angiogenic agents; anticoagulants, bone promoters; cytokines; interleukins; genetic material; genes encoding bone promoting action; cells containing genes encoding bone promoting action; cells genetically altered by the hand of man; externally expanded autograft or xenograft cells; growth hormones such as somatotropin; bone digestors; anti-tumor agents; fibronectin; cellular attractants and attachment agents; immunosuppressants; bone resorption inhibitors and stimulators; mitogenic factors; bioactive factors that inhibit and stimulate second messenger molecules; cell adhesion molecules, e.g. cell-matrix and cell-cell adhesion molecules; secondary messengers; monoclonal antibodies specific to cell surface determinants on mesenchymal stem cells; portions of monoclonal antibodies specific to cell surface determinants on mesenchymal stem cells; clotting factors; polynucleotides; and combinations thereof. The amount of the bioactive agent included with the bone or cartilage matrix composition can vary widely and will depend on such factors as the agent being delivered, the site of administration, the patient's physiological condition, etc. The optimum levels being determined in a specific case based upon the intended use of the implant.

For example, inventive bone or cartilage matrix compositions may be prepared so that they include one or more compounds selected from the group consisting of drugs that act at synaptic and neuroeffector junctional sites (e.g., acetylcholine, methacholine, pilocarpine, atropine, scopolamine, physostigmine, succinylcholine, epinephrine, norepinephrine, dopamine, dobutamine, isoproterenol, albuterol, propranolol, serotonin); drugs that act on the central nervous system (e.g., clonazepam, diazepam, lorazepam, benzocaine, bupivacaine, lidocaine, tetracaine, ropivacaine, amitriptyline, fluoxetine, paroxetine, valproic acid, carbamazepine, bromocriptine, morphine, fentanyl, naltrexone, naloxone,); drugs that modulate inflammatory responses (e.g., aspirin, indomethacin, ibuprofen, naproxen, steroids, cromolyn sodium, theophylline); drugs that affect renal and/or cardiovascular function (e.g., furosemide, thiazide, amiloride, spironolactone, captopril, enalapril, lisinopril, diltiazem, nifedipine, verapamil, digoxin, isordil, dobutamine, lidocaine, quinidine, adenosine, digitalis, mevastatin, lovastatin, simvastatin, mevalonate); drugs that affect gastrointestinal function (e.g., omeprazole, sucralfate); antibiotics (e.g., tetracycline, clindamycin, amphotericin B, quinine, methicillin, vancomycin, penicillin G, amoxicillin, gentamicin, erythromycin, ciprofloxacin, doxycycline, acyclovir, zidovudine (AZT), ddC, ddI, ribavirin, cefaclor, cephalexin, streptomycin, gentamicin, tobramycin, chloramphenicol, isoniazid, fluconazole, amantadine, interferon,); anti-cancer agents (e.g., cyclophosphamide, methotrexate, fluorouracil, cytarabine, mercaptopurine, vinblastine, vincristine, doxorubicin, bleomycin, mitomycin C, hydroxyurea, prednisone, tamoxifen, cisplatin, decarbazine); immunomodulatory agents (e.g., interleukins, interferons, GM-CSF, TNFα, TNFβ, cyclosporine, FK506, azathioprine, steroids); drugs acting on the blood and/or the blood-forming organs (e.g., interleukins, G-CSF, GM-CSF, erythropoietin, vitamins, iron, copper, vitamin $B_{12}$, folic acid, heparin, warfarin, coumarin); hormones (e.g., growth hormone (GH), prolactin, luteinizing hormone, TSH, ACTH, insulin, FSH, CG, somatostatin, estrogens, androgens, progesterone, gonadotropin-releasing hormone (GnRH), thyroxine, triiodothyronine); hormone antagonists; agents affecting calcification and bone turnover (e.g., calcium, phosphate, parathyroid hormone (PTH), vitamin D, bisphosphonates, calcitonin, fluoride), vitamins (e.g., riboflavin, nicotinic acid, pyridoxine, pantothenic acid, biotin, choline, inositol, carnitine, vitamin C, vitamin A, vitamin E, vitamin K), gene therapy agents (e.g., viral vectors, nucleic-acid-bearing liposomes, DNA-protein conjugates, anti-sense agents); or other agents such as targeting agents etc.

In certain embodiments, the agent to be delivered is adsorbed to or otherwise associated with the matrix being implanted. The agent may be associated with the matrix of the bone or cartilage matrix composition through specific or non-specific interactions; or covalent or non-covalent interactions. Examples of specific interactions include those between a ligand and a receptor, a epitope and an antibody, etc. Examples of non-specific interactions include hydrophobic interactions, electrostatic interactions, magnetic interactions, dipole interactions, van der Waals interactions, hydrogen bonding, etc. In certain embodiments, the agent is attached to the matrix using a linker so that the agent is free to associate with its receptor or site of action in vivo. In other preferred embodiments the agent is either covalently or non-covalently attached to the matrix. In certain preferred embodiments, the agent to be delivered may be attached to a chemical compound such as a peptide that is recognized by the matrix of the bone or cartilage matrix composition. In another embodiment, the agent to be delivered is attached to an antibody, or fragment thereof, that recognizes an epitope found within the matrix of the bone or cartilage matrix composition. In certain embodiments at least two bioactive agents are attached to the bone or cartilage matrix composition. In other embodiments at least three bioactive agents are attached to the bone or cartilage matrix composition. A bioactive agent may be provided within the bone matrix composition in a sustained release format. For example, the bioactive agent may be encapsulated within biodegradable nanospheres, microspheres, etc.

These and other aspects of the present invention will be further appreciated upon consideration of the following Examples, which are intended to illustrate certain particular embodiments of the invention but are not intended to limit its scope, as defined by the claims.

EXAMPLES

Example 1

The Effect of Furin on Demineralized Bone Matrix

This example relates to the study of the effect of furin and other PPC's on the osteoinductive capacity of human demineralized bone matrix.

A solution of 100 mM HEPES containing 0.5% Triton X-100, 1 mM $CaCl_2$, pH 7.5 is prepared. Various amounts of human DBM (e.g., 40 mg) are incubated in the aforementioned HEPES buffer containing furin at concentrations of 0, 1, 5, 10, 20, 30, 40, 50, 60, 70, 80, 90 and 100 units per ml at temperatures ranging from 4° C. to 60° C. (e.g., 23° C., 37° C.) for periods ranging from 1 hour to 1 week (e.g., 24 hrs).

The above steps are repeated with the addition of 3 mM iodoacetic and/or 0.1 mM Benzamidine HCl in order to protect osteoinductivity of DBM. As a control, the experiment is repeated including 1 mM EGTA or the specific furin inhibitor $C_{34}H_{66}N_{11}O_5Cl$ (1 mM) in the HEPES Buffer. At the end of the incubation period the bone is washed with deionized $H_2O$ and lyophilized. 40 mg doses are implanted in the quadriceps of nude rats. The animals are euthanized after 28 days and the amounts of bone formation by furin treated DBM and control groups histologically and radiographically quantified (see, e.g., Kawai and Urist, *Clin. Orthop*. (1998) 233:262-267).

Example 2

Preparing Demineralized Bone Matrix (DBM)

DBM may be prepared using any method or technique known in the art (see Russell et al. *Orthopedics* 22(5):524-531, May 1999; incorporated herein by reference). The following is an exemplary procedure for preparing demineralized bone derived from Glowacki et al. "Demineralized Bone Implants" *Clinics in Plastic Surgery* 12(2):233-241, April 1985, which is incorporated herein by reference. Bones or bone fragments from donors are cleaned to remove any adherent periosteum, muscle, connective tissue, tendons, ligaments, and cartilage. Cancellous bone may be separated from dense cortical bone and processed as large pieces. Cortical bone may be cut into small pieces to improve the efficiency of subsequent washes and extractions. Denser bone from larger animals may need to be frozen and hammered in order to produce chips less than 1 cm. The resulting pieces of bone are thoroughly washed with cold, deionized water to remove marrow and soft tissue.

The cleaned bone is then extracted with frequent changes of absolute ethanol for at least 1 hour. Typically, a total of 4 liters of ethanol is used per 100 g of bone. The bone is then extracted with frequent changes of anhydrous diethyl ether in a fume hood for 1 hour. Typically, 2 liters of ether is used per 100 g of bone. The bone is dehydrated by these extractions of ethanol and ether and can be stored at room temperature.

The dehydrated bone is then frozen and then pulverized in a liquid nitrogen-impacting mill. Pulverized bone is then sieved into fractions of 75 to 250, 250 to 450, and greater than 450 microns. Bone particle fractions are then demineralized using 0.5 M hydrochloric acid (50 ml per gram) for 3 hours at room temperature or at 4° C. on magnetic stirrers with insulation to prevent overheating. Large chips of bone and blocks are extracted completely at 4° C. with frequent changes of 0.5 M hydrochloric acid. The demineralization process can be monitored radiographically, by ashing, or by nondecalcified histologic techniques (von Kossa stain).

The acid and liberated minerals are washed away with cold, deionized water until the pH of the wash matches the pH of the water. The water washes can be decanted from the large particles and chips of bone; however, the washes must be removed by centrifugation from the finer particles. The washing step requires approximately 500 ml of water per gram of starting bone particles. Demineralized bone powders are extracted with changes of absolute ethanol for 1 hour using 200 ml of ethanol per gram of starting bone particles. The material is extracted in a fume hood with changes of anhydrous ethyl ether for 1 hour with 100 ml of ether per gram of starting bone particles. After the last change of ether is removed, the demineralized bone powder is left overnight in the hood until all the residual ether has vaporized. The particles should be odorless, snow-white, and discrete. To sterilize the demineralized bone material, it may be treated with cold ethylene oxide or irradiated.

To test the bioactivity of the prepared DBM, 25 mg of the material is implanted into each of two thoracic subcutaneous pockets in shaved, anesthetized 28-day old male Charles River CD rats. The implanted specimens may then be harvested and inspected several days after implantation. The composition of the induced tissue can be quantified by histomorphometric analysis and be biochemical techniques.

Example 3

Another Method of Preparing DBM

DBM may be prepared using any method or techniques known in the art (See Russell et al., *Orthopedics* 22(5):524-531, May 1999; incorporated herein by reference).

Demineralized bone matrix is prepared from long bones. The diaphyseal region is cleaned of any adhering soft tissue and then ground in a mill. Ground material is sieved to yield a powder with particles approximately 100 μm to 500 μm in diameter. The particulate bone is demineralized to less than about 1% (by weight) residual calcium using a solution of Triton X-100 (Sigma Chemical Company, St Louis, Mo.) and 0.6N HCl at room temperature followed by a solution of fresh 0.6N HCl. The powder material is rinsed with deionized water until the pH was greater than 4.0. It then is soaked in 70% ethanol and freeze-dried to less than 5% residual moisture.

Example 4

Determining Time Course for Induction of Bone Growth by Intermuscular Implant

This Example characterizes the time course of induction of bone growth in an intermuscular site using the inventive materials, as compared with DBM base powder (as in Example 1), at time points of 7, 14, 28, and 35 days. This Example is adapted from the rat model for assessing osteoinduction of DBM found in Edwards et al. "Osteoinduction of Human Demineralized Bone: Characterization in a Rat Model" *Clinical Orthopaedics* 357:219-228, December 1998; incorporated herein by reference.

The study is conducted in athymic (nude) rats in order to minimize the potential for a cross-species incompatibility response to human tissue implants. The hind-limb intermuscular site is used for the initial determination of heterotopic bone induction properties because the site does not naturally contain bone.

Rats, for example, female homozygous rnu/rnu rats in the 50-75 g range are obtained. The rats are housed for one week for acclimatization purposes prior to surgery. Sterile microisolator cages are used throughout the investigation, with sterile water and rodent diet provided ad libitum.

Implant Placement: A single intermuscular (IM) site is utilized in each hind limb of 30 rats. To provide a common positive control over all animals, a single 40 mg sample of rat DBM powder is placed intramuscularly within the left pectoralis (LP) muscle of each rat. Animals are allowed normal activities following surgical procedures.

Implant Materials: DBM and test materials are kept at room temperature. Eight 145 mg samples of Test and eight 40-mg samples of DBM powder are tested for implantation times of 7, 14, and 28 days. Six samples of each are tested at 35 days. The 40 mg samples of DBM powder are rehydrated with 100 μl of sterile ALLOPREP™ (Ostetotech, Eatontown, N.J.). Each of the samples is packed into a 1 ml blunt cut syringe. Implantation is randomized so that a single animal does not receive two of the same implants.

Anesthesia: The rats are anesthetized with a mixture of ketamine (200 mg), xylazine (400 mg), and physiological saline (10 ml). The dosage was 3.5 ml/kg body weight administered intraperitoneally.

Procedure: Aseptic surgical procedures are carried out in a laminar airflow hood. A 1-cm skin incision is made on each upper hind limb using a lateral approach, and the skin is separated from the muscle by blunt dissection. A superficial incision aligned with the muscle plane is made to allow for insertion of the tips of the scissors. Blunt dissection is performed from this line deep into the muscle to create a pocket to hold the implanted material. A single suture is inserted to close the muscle pocket, and the skin is closed with metal clips.

Implantation of specimens in the left pectoralis muscles involved making a 1-cm skin incision over the chest, blunt dissection of the muscle to create a pocket, and positioning of the rat DBM powder using a blunt syringe. A single suture is inserted to close the muscle pocket, and the skin is closed with metal clips.

Rats are euthanized with $CO_2$ following the designated implantation time. Implant materials are located by palpation, retrieved by blunt dissection, and cleaned of the surrounding tissue by careful trimming. An observer blinded to implant type performed a macroscopic evaluation of the implant material. Color, vascularity, hardness, and integrity are scored according to the scheme outlined in the Table below. (The highest score for the most robust response would be a 4 while a specimen showing little or no osteoinductive potential would score a 0.) Experience with this model has shown a high correlation between visual observations and histological observations of implant performance only at the extremes of both ends of the scale.

| Macroscopic Observation Scoring Guidelines | | | |
|---|---|---|---|
| Color: | White (W) | Grey (G) | Red (R) |
| Vascularity: | None (N) | Some (S) | Robust (R) |
| Hardness: | Mushy (M) | Firm (F) | Hard (H) |
| Integrity: | Diffuse (D) | Flat (F) | Nodule (N) |
| Score: | 0 | 0.5 | 1 |

Histology: Retrieved materials are fixed in Neutral buffered formalin. After fixation in formalin, samples are decalcified in 10% formic acid, dehydrated in graded alcohols, embedded in JB-4 (glycol methacrylate, Polysciences, Inc., Warrington, Pa.) and sectioned. Five-micron sections are stained with toluidine blue and evaluated by light microscopy.

These explants are histologically evaluated using a semi-quantitative method. Briefly, a numerical score based on a five-point scale is assigned to each section of nodule: 4=more than 75% involved in new bone formation; 3=51-75% involved in new bone formation; 2=26-50% involved in new bone formation; 1=1-25% of the explant involved in new bone formation; and 0=no evidence for the process of endochondral bone formation including the presence of cartilage or chondrocytes, active osteoblasts, osteoid, newly formed and mineralized bone, and/or marrow and associated fat cells.

| Scoring of Histological Sections | |
|---|---|
| Score | New Bone Formation |
| 0 | No new bone formation |
| 1 | <25% new bone formation |
| 2 | 26-50% new bone formation |
| 3 | 51-75% new bone formation |
| 4 | >75% new bone formation |

Following histological analysis, average scores are calculated for each material type. Based on previous experience with this animal model, each group is assigned an assessment of osteoinductive potential based on the average histological score.

Example 5

Evaluating Efficacy of Inventive Compositions in Healing Bone Defects

Background Information: Morselized autogenous cancellous bone (ABG) has long been considered the "gold standard" for osteoinduction when a bone graft is required in an orthopedic clinical situation. Unfortunately, the amount of ABG available is limited, and there is at least a 5% surgical morbidity associated with the harvesting procedure. Demineralized bone matrix (DBM) has been shown to have equal to superior healing potential to ABG.

The rabbit ulna defect model has been modified and used in numerous projects to test the efficiency of osteoinductive and osteoconductive growth factors and matrices as substitute to autogenous bone graft. This study can evaluate the bone inducing capacity of the new DBM formulation grafting material in comparison to previous formulations and ABG.

Materials and Methods:
Study Design Summary:
A. Rabbit bilateral 2-cm ulnar defects.
Treatment groups:
  DBM+osteoinductive peptides or protein fragments
  DBM+protease
  DBM alone Autograft (Historical Data Used for Comparison)

Surgical Procedure: Six months old male New Zealand white rabbits are used. A 2.0 centimeter non-uniting defect is surgically created in the bilateral ulnae of all rabbits. After complete periostectomy, thorough defect wash, and partial diaphyseal wash, grafting is implanted (according to test groups) via open surgical technique into each defect. The wound is closed primarily in layers. When anesthesia is achieved, both forelimbs are shaved and prepared with the rabbit supine (limbs up) position. Longitudinal incisions (3-4 cm) are made over both ulnae and the diaphysis (midshaft) portion of the ulna is exposed. The distal osteotomy is made 1 cm from the ulnocarpal (wrist) joint and the proximal osteotomy made 3.0 cm from the ulnocarpal joint, to create a 2 cm defect. The osteotomies are created with a high speed burr. The resultant loose block of diaphyseal bone is excised with its periosteum intact. Due to the very adherent interosseous membrane of the rabbit forelimb, internal fixation may not be required. After irrigation with sterile saline to remove blood, bone, and marrow remnants, the implant material is placed in the defect. The deep fascial layer is closed as an envelope around the defect with 3-0 chromic suture. The skin is closed with interrupted nylon suture. A post-operative dressing/splint is applied and removed on the fourth post-operative day.

Radiographs: Antero-posterior radiographs may be obtained immediately post-operatively and additional radiographs are taken at 3, 6, 9, and 12 weeks. High resolution (Faxitron) radiographs may be taken of both limbs after excision and cleaned of soft tissue at either 6 or 12 weeks. Three blinded observers asses each time point for bone formation and remodeling.

Example 6

Osteoinduction in a Rabbit Model

Introduction and methods: Fifty-five male New Zealand White rabbits are assigned to three treatment groups. Test article is first prepared (e.g., DBM with a protease or with peptides and protein fragments having osteoinductivity). Those animals assigned to the Low Dose treatment group (n=20) receive 3.5 ml of the test article in the right paravertebral muscle following a protocol specified procedure. Animals assigned to the High Dose treatment group (n=20) receive 3.5 ml of the test article in the right paravertebral muscle and 7.0 ml of the test article in the subcutaneous tissue of each side of the dorsal thoracic area. Some animals are assigned to the Control treatment group and are implanted with 3.5 ml of control article (rehydrated DBM powder) in the right paravertebral muscle. At 7, 14, and 28 days post-implantation, animals from the Low and High Dose treatment groups and animals from the Control groups are humanely sacrificed. At 60 days post-implantation, the remaining animals are sacrificed. The implant sites are collected from each rabbit and fixed in 10% neutral buffered formalin (NBF). The test and control implant sites from the 60 days post-implantation study interval are placed in decalcification solutions for 3 days after adequate formalin fixation. All tissue samples are processed using standard histological techniques, sectioned at 5 μm, and stained with hematoxylin and eosin.

Example 7

Terminal Sterilization

This example describes a terminal sterilization method, which minimizes osteoinductivity loss in the inventive preparations.

The inventive DBM preparations are produced in a clean room environment from human tissue. The finished implants are placed in individual tray packages.

Each tray is placed in an Audionvac sealing apparatus (Audion Electro B. V., Weesp-Holland), which is supplied with a cylinder consisting of 50/50 hydrogen/argon gas. Before the tray packages are sealed, they are evacuated and backfilled with the gas mixture twice. Following sealing, the gas mixture remains in each tray package.

The packaged implants are then sealed packages and then treated with 15 KGy gamma radiation from a cobalt 60 source to reduce the bioburden of the implants to the desired level.

Example 8

Process of Making a Species-Specific Osteoimplant with Defined Dimensions

Long bones from human Rhesus Monkey, canine, and rabbit are used to prepare species-specific solid formed implant matrices. Bones are aseptically cleaned. The cortical bone is processed in the bone milling apparatus described in U.S. Pat. No. 5,607,269, incorporated herein by reference, to yield about 65 grams of elongate bone fibers. The elongate bone fibers are placed in a reactor and allowed to soak for about 5-10 minutes in 0.6 N HCl plus 20-2000 ppm nonionic surfactant solution. Following drainage of the HCl/surfactant, 0.6 N HCl at 15 ml per gram of total bone is introduced into the reactor along with the elongate bone fibers. The reaction proceeds for about 40-50 minutes. Following drainage through a sieve, the resulting demineralized elongate bone fibers are rinsed three times with sterile, deionized water at 15 ml per gram of total bone, being replaced at 15-minute intervals. Following drainage of the water, the bone fibers are covered in alcohol and allowed to soak for at least 30 minutes. The alcohol is then drained and the bone fibers are rinsed with sterile, deionized water. The bone fibers are then contacted with a mixture of about 4.5 ml glycerol per gram of dry bone fibers and about 10.5 ml sterile deionized water per gram of dry bone fibers s for at least 60 minutes. Excess liquid is drained and the resulting liquid composition containing approximately 11% (w/v) demineralized, elongate bone fibers was transferred to a 11 cm×11 cm mold containing a lid having a plurality of protruding indentations (approximately 1.5 cm×3.5 cm in width and length, and 4 mm in depth), the lid is gently placed on the mold such that the indentations become immersed into the fibers to exert as little pressure on the composition as possible. The dimensions of the protrusions can be made specific for the size of the osteoimplant required for the animal model of interest. The resulting cut pieces have specified dimensions of, e.g., 4.5 cm in length, 2.5 cm in width and about 8 mm in height (or thickness) with trough dimensions 3.5 cm in length, 1 cm in width and depth of the of 4 mm. The mold is then placed in an oven at 46° C. for 4 hours. The composition is then frozen overnight at −70° C. and then lyophilized for 48 hours. Following lyophilization, the mold is disassembled and the sponge-like formed composition is cut into individual pieces that contained troughs.

The resulting composition is cohesive, flexible, sponge-like with an obvious continuous three-dimensional structure with visible open pores, has a defined shape including the indentations made by the lid protrusions, does not require rehydration before use, but is rapidly hydratable and retained its shape once wetted with fluids and freezing is not required for storage.

Example 9

Osteoinduction of DBM Composition in an Athymic Rat Model

The purpose of this Example is to evaluate the osteoinductive potential of DBM compositions using a heterotopic osteoinductive 28-day implant model (Edwards et al., *Clin. Orthop. Rel. Res.* 357:219-228, 1998; Urist, *Science* 150: 893-899, 1965; each of which is incorporated by reference). The DBM composition includes cuboidal shaped DBM particles in combination with DBM fibers (See U.S. Ser. No. 60/159,774, filed Oct. 15, 1999; WO0232348; each of which is included herein by reference). Chondrocytes are the predominant cell type in the cube of the DBM following 28-day implantation. This study extends the implant time to 49 days to look evidence of continued bone remodeling within the demineralized cortical cube.

Materials and Methods: Equal volumes of crunch samples weighing approximately 600 mg are packaged in 2.5 ml blunt tipped syringes. Eighteen female athymic rats are obtained from Harlan Sprague Dawley Inc. (Indianapolis, Ind.). Animals' weights at the time of surgery are measured. 28-day and 49-day implants are evaluated.

The implant sites are assessed histologically. The fiber component is scored independently of the cubes and is assigned a numerical score based on a 5 point semiquantitative scale based on percent of fiber area involved in new bone formation. The cube portion is assigned a score based on the percent of central Haversian systems involved in new bone formation.

Example 10

Effects of Collagenase Treatment on DBM Activity and Properties in a Novel Tissue Culture System Materials and Methods Preparation of Standard DBM. Methods for preparing demineralized bone matrix have been described previously in the literature (Urist M R, Iwata H, Ceccotti P L, Dorfman R L, Boyd S D, McDowell R M, Chien C. Bone morphogenesis in implants of insoluble bone gelatin. Proc Natl Acad Sci USA. 1973 December; 70(12):3511-5; Sampath T K, Coughlin J E, Whetstone R M, Banach D, Corbett C, Ridge R J, Ozkaynak E, Oppermann H, Rueger D C. Bovine osteogenic protein is composed of dimers of OP-1 and BMP-2A, two members of the transforming growth factor-beta superfamily. J Biol Chem. 1990 Aug. 5; 265(22):13198-205. We prepared osteoinductive demineralized human bone matrix from cortical diaphyseal long bones free from marrow and adhering soft tissues using a method similar to that described in Edwards J T, Diegmann M H, Scarborough N L. Osteoinduction of human demineralized bone: characterization in a rat model. Clin Orthop. 1998 December; (357):219-28). As the osteoinductive growth factors in bone are unstable, the bone was kept in a frozen state prior to the cleaning and the demineralization steps. (If the bone is to be cleaned at room temperature, the cleaning should be done as quickly as possible (less than 2 hours) to avoid denaturing the osteoinductive factors.)

The bones were cut into small cylindrical segments and then powdered using a mill (e.g. Wiley wheat mill, Munson Mill, Fitz Mill). In our experiments we powdered the bone to a size ranging from 106 to 500 µm. The bone powder was defatted in 70% ethanol for 1 hour. Other organic solutions (e.g., a 1:1 solution of chloroform/methanol) and/or time periods could be used, e.g., 30 minutes-24 hours. The ethanol solution was poured off and the residue allowed to evaporate away from the bone. No residual organic material was observable following this process.

The defatted bone was then submerged in several volumes (~15 volumes) of 0.6N HCl and allowed to demineralize under agitation. The acid bath was changed at least once to allow demineralization to less than 1% residual calcium. The demineralization was typically carried out at temperatures ranging from 2° C. to 20° C. The process typically takes between 1 hour and several days depending on the particle size of the bone, the temperature of demineralization, and the number of times the acid batch is changed. In our case 2 hours was sufficient for the experiments described here. The residual acid was then washed from the bone with several volumes of distilled water and the material was lyophilized.

Collagenase Digestion of DBM. Human demineralized bone matrix 100-500 microns in size, was prepared as described immediately above. Some material was inactivated by repeated extraction with 4 M guanidine hydrochloride. Limited digestion with collagenase was carried out as follows: 1 gram of DBM or inactivated DBM was digested for a period of 1 hour at 37° C. in 3 ml of 50 mM Tris-HCl buffer, pH 7.4, containing 5 mM $CaCl_2$, and 80 units/ml purified bacterial collagenase (Worthington Biochemical, CLSPA collagenase). The residual matrix was then stirred for 1 hour in 45 ml 0.1N acetic acid at 4° C. After the acid treatment, the matrix was washed twice for 30 minutes with cold water and neutralized by washing for 30 minutes with cold PBS.

As an experimental control, one aliquot of DBM was treated as described except that collagenase was omitted from the digestion buffer. For all the various bone matrix treatment groups, the equivalent of 100 mg of dry demineralized bone was utilized.

Preparation of Human Bone Matrix Gelatin (BMG). BMG was prepared from osteoinductive DBM by the following method:

1. DBM particles were extracted with 10 volumes of 2 M $CaCl_2$ at 4° C. for 2 hrs.
2. The material was washed twice for 15 minutes with distilled water.
3. The material was extracted with 10 volumes 0.5 M EDTA, pH 7.4 at 4° C. for 2 hrs.
4. Step 2 was repeated.
5. The material was extracted with 4 volumes of 8 M LiCl at 4° C. for 18 hrs.
6. The material was washed twice with 10 volumes of cold distilled water for 30 minutes.
7. The recovered matrix was placed in sterile water at 55° C. for 1 hr.
8. The matrix was lyophilized.

Tissue Culture and Cell Treatment with DBM. C2C12 mouse myoblastic cells were purchased from ATCC. Passage 6 cells were plated in 24 well plates at a concentration of 30,000 cells per well (depending on experiment). Cells were either grown in Dulbecco's Modification of Eagles Media (Hyclone, SH30243.01) or Minimum Essential Alpha Medium (Gibco 12571-063) supplemented with L-glutamine, Fetal Bovine Serum (Hyclone, SH30071.02) and antibiotics (Penicillin/Streptomycin).

After overnight attachment the cells were exposed to various treatments. During the course of the experiments, 1 ml of culture media was added to each well. Recombinant human BMP-2 (R&D Systems, 355-BM-010) was added to the BMP treatment groups at a concentration of 100 ng/ml. DBM (collagenase treated and untreated, active and inactive) was added to the wells in Falcon 8.0 um cell culture inserts (Falcon, 353097). Prior to adding the DBM to the tissue culture inserts, it was pre-swollen with tissue culture media. The inserts were placed on top of the cells that adhered to the bottom of the tissue culture well.

Cells were grown for 6 days in a 37° C. incubator where $CO_2$ concentration was maintained at 5%. The media in each well was replenished at 48 hr intervals. Fresh BMP was added to BMP treatment wells; fresh culture media alone was added to all other wells. The tissue culture inserts containing DBM were temporarily removed for a minimal time period during addition of fresh medium. The DBM in the tissue culture inserts was not removed. No additional DBM was added. It is noted that the activity of the DBM may decrease over time (e.g., as factors diffuse out of the DBM). Therefore experiments in which the DBM in the tissue culture inserts is replaced during the experiments, e.g., at the time of adding fresh medium, may show even more significant effects on alkaline phosphatase expression.

Alkaline Phosphatase Assay. At the end of the treatment period the cell culture inserts were removed and media was aspirated from all wells. The wells were rinsed three times with phosphate buffered saline and the cells were lysed by adding 1 ml 10 mM Tris-HCl buffer, pH 7.4, containing 1 mM $MgCl_2$, 20 uM $ZnCl_2$, and 0.02% Triton x-100 followed by mechanical disruption and followed by three 20 second pulses of sonication on ice (Branson model 1510 sonicator).

The alkaline phosphatase activity of the lysate was then determined by standard techniques. In brief, a known volume of cell lysate (10 ul, 20 ul, or 50 ul depending on particular experiment) was added to 96 well assay plates and the total volume in each well was adjusted to 220 ul by adding 100 mM diethanolamine buffer, pH 10.5, containing 1 mM $MgCl_2$, and 7.6 mM p-Nitrophenol phosphate (substrate solution). The assay plate was incubated at 37° C. for 30 minutes and the reaction was stopped by addition of 20 ul of 240 mM NaOH. Using a microplate reader, the absorbance of each well was determined at 405 nm. After adjusting for the absorbance of the buffer blank, the alkaline phosphatase activity each sample was determined by comparison to absorbance of known concentrations of p-Nitrophenol standards.

In cases where specific alkaline phosphatase activity is reported, total protein concentration was measured using either the method of Bradford or the Pierce BCA assay.

Evaluating Solubility of DBM. C2C12 were initially cultured in the presence of 100 mg standard DBM (DBM) or collagenase treated DBM (Collagease DBM) placed in 8.0 um cell culture inserts. After 6 days of culture, the inserts were removed from the wells containing the cells, and the residual matrix was washed repeatedly with water and then lyophilized. The dry weight of the recovered matrix was measured and reported as percent DBM recovered.

Implantation of DBM and BMG into Rats. 40 mg of human DBM or 40 mg of human BMG was implanted in the quadriceps muscle of 6 week old female Harlan athymic rats (mu/mu). 28 days after surgery the nodules were recovered, and histological sections were prepared and stained with Toluidine Blue to allow visualization of residual bone matrix along with new osteoid, bone marrow, and cartilage.

Results and Discussion

When prepared properly, e.g., as described herein, demineralized bone matrix has the ability to induce heterotopic bone formation in several animal models including mice, rats, and rabbits (Urist M R. Bone: formation by autoinduction. Science. 1965 Nov. 12; 150(698):893-9). The bone and cartilage forming activity of DBM may be attributed at least in part to the presence of growth factors which diffuse from the matrix and stimulate the differentiation of relatively uncommitted cells along the osteoblastic and chondroblastic lineages (Urist M R, Silverman B F, Buring K, Dubuc F L, Rosenberg J M. The bone induction principle, *Clin Orthop.* 1967 July-August; 53:243-83). Not all animal species demonstrate similar ability to respond to demineralized bone matrix. In particular, the ability of DBM to induce bone formation in higher order species such as dogs (Caplanis N, Lee M B, Zimmerman G J, Selvig K A, Wikesjo U M. Effect of allogenic freeze-dried demineralized bone matrix on guided tissue regeneration in dogs. J Periodontol. 1998, August; 69(8):851-6) and squirrel monkeys (Aspenberg P, Wang E, Thomgren K G. Bone morphogenetic protein induces bone in the squirrel monkey, but bone matrix does not. *Acta Orthop Scand.* 1992 December; 63(6):619-22) has been questioned. These species differences could either result from the ability of hosts to respond or actual differences in the osteoinductive potential of DBM derived from the various species.

While various preparations of rat DBM have been shown to be effective in inducing cartilage differentiation in primary cultures of neonatal rat muscle (Nogami H, Urist M R. Substrata prepared from bone matrix for chondrogenesis in tissue culture. *J Cell Biol.* 1974 August; 62(2):510-9), our studies have indicated that standard preparations of human DBM, which are of most interest from a therapeutic standpoint, are not particularly potent in vitro. Specifically, in our experiments human DBM induced only a small increase in the expression of the osteoblast marker alkaline phosphatase in cultures of murine C2C12 or C3H10T1/2 cells. These results are consistent with the literature. For example, in one set of experiments, Han et al. demonstrated only a four fold increase in specific alkaline phosphatase activity of C2C12 cells treated with human DBM over that of cells treated with inactivated DBM (Han B, Tang B, Nimni M E. Quantitative and sensitive in vitro assay for osteoinductive activity of demineralized bone matrix. *J Orthop Res.* 2003 July; 21(4):648-54). Our attempts to replicate the method described in another publication (Peel S A, Hu Z M, Clokie C M. In search of the ideal bone morphogenetic protein delivery system: in vitro studies on demineralized bone matrix, purified, and recombinant bone morphogenetic protein. *J Craniofac Surg.* 2003 May; 14(3):284-91) yielded inconsistent results. In one experiment we were able to visualize an approximately four fold increase in alkaline phosphatase activity over controls. For example, as shown in FIG. 2, C2C12 cells cultured with DBM using a method corresponding to the work of Peel et al., in the presence of 5% or 15% fetal bovine serum display only low levels of alkaline phosphatase activity, indicating a lack of significant differentiation along the osteoblast lineage. We were not able to repeat these results. Thus it is evident that although rat DBM, rat bone matrix gelatin (BMG), and collagenase treated rat bone matrix gelatin (DBM exposed to LiCl) have chondrogenic potential in vitro, standard human DBM and human bone matrix gelatin (results for BMG not shown) appear to lack such potential. For example, standard human DBM and human bone matrix gelatin lack the ability to induce detectable levels of alkaline phosphatase in clonal cells.

Figure 3:
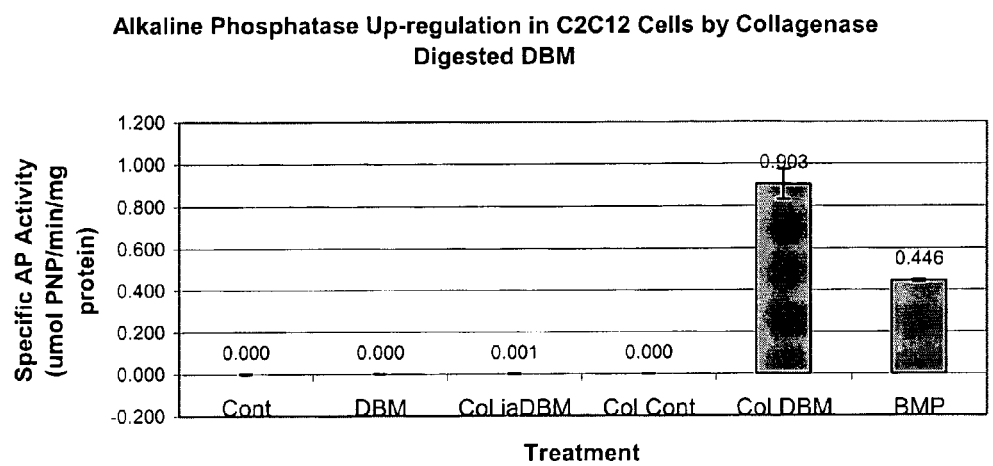
FIG. 3 is a bar graph showing specific alkaline phosphatase activity of C2C12 cells treated with various preparations of human demineralized bone matrix (DBM), fetal bovine serum (FBS), or bone morphogenetic protein-2 (BMP-2) for 6 days. The various groups are as follows: Cont: culture media only; DBM: 100 mg of human DBM; Col iaDBM: 100 mg Collagenase-treated GuHCl inactivated human DBM; Col Cont: 100 mg DBM incubated in digestion buffer lacking collagenase and undergoing washing and neutralization steps; Col DBM: 100 mg Collagenase treated human DBM, BMP: 100 ng BMP-2 (refreshed at each feeding). Cells were grown in DMEM supplemented with 10% FBS, 0.284 mM ascorbate 2-phosphate and 10 mM beta-glycerol phosphate.
Figure 4:
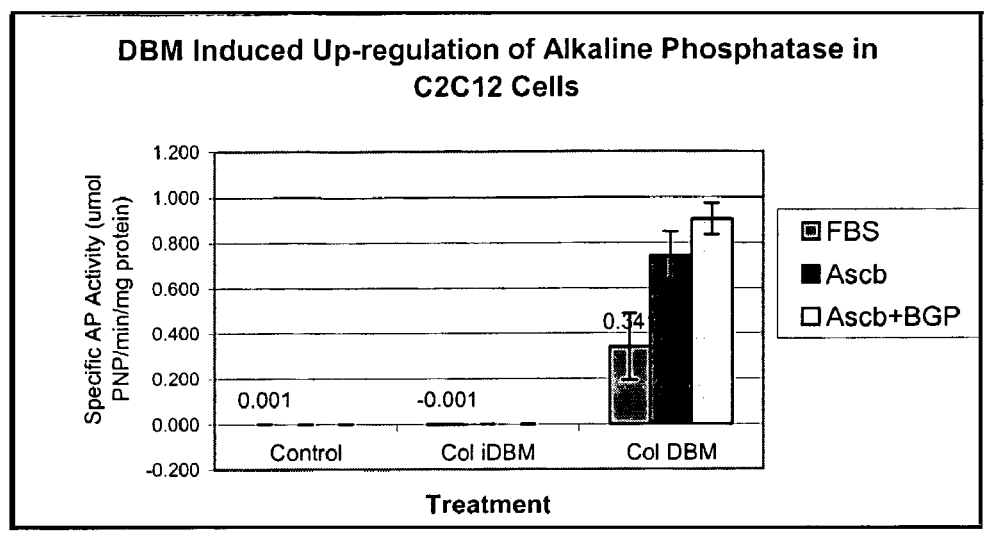
FIG. 4 is a bar graph showing the effect of ascorbate 2-phosphate (Ascb) and beta-glycerol phosphate (BGP) on the in vitro activity of collagenase-treated DBM. Treatment groups are labeled as in FIG. 3. Each group was cultured either in DMEM containing 10% FBS (leftmost bars in each set of 3), or DMEM containing 10% FBS supplemented with 0.284 mM ascorbate 2-phosphate (middle bars in each set of 3), or DMEM containing 10% FBS supplemented with 0.284 mM ascorbate 2-phosphate and 10 mM beta-glycerol phosphate (rightmost bars in each set of 3).

In an effort to increase the activity of human DBM, we exposed the material to collagenase treatment and assessed the effects of this treatment and others on the osteogenic and/or chondrogenic activity of DBM in a tissue culture system. In particular, we treated relatively undifferentiated mesenchymal cells with DBM (treated, untreated, or inactivated) and measured its effect on alkaline phosphatase activity of the cells. Our results indicate that collagenase has a profound effect on the activity of human DBM. In particular, the activity of human DBM in tissue culture can be markedly enhanced if the DBM undergoes limited digestion with purified bacterial collagenase. This increased potency is evidenced by increased expression of alkaline phosphatase activity in cultures of C2C12 cells treated with this modified DBM (FIG. 3). In FIG. 4 it can be seen that the presence of ascorbate 2-phosphate and beta-glycerol phosphate, which may positively influence expression of aspects of the osteoblastic and/or chondroblastic phenotype under certain conditions, enhances but is not essential for visualizing this activity. Standard preparations of human DBM with demonstrated osteoinductive ability in rats fail to induce this phenotype (FIG. 3, DBM group). The data presented graphically in FIGS. 3 and 4 is tabulated below.

TABLE

Specific alkaline phosphatase activity of C2C12 cells treated with various preparations of human DBM, FBS, or BMP-2 (data shown in FIG. 3).

| Treatment | Specific AP Activity (umol PNP/min/mg protein) |
|---|---|
| Cont | 0.000 |
| DBM | 0.000 |
| Col iaDBM | 0.001 |

TABLE-continued

Specific alkaline phosphatase activity of C2C12
cells treated with various preparations of human
DBM, FBS, or BMP-2 (data shown in FIG. 3).

| Treatment | Specific AP Activity (umol PNP/min/mg protein) |
| --- | --- |
| Col Cont | 0.000 |
| Col DBM | 0.903 |
| BMP | 0.446 |

TABLE

The effect of Ascorbate 2-phosphate (Ascb) and beta-glycerol
phosphate (BGP) on the in vitro activity of collagenase
treated DBM (data shown in FIG. 4).

| Treatment | Specific AP Activity (umol PNP/min/mg protein) |
| --- | --- |
| Control | 0.001 |
| Control + Ascb | 0.000 |
| Control + Ascb + BGP | 0.000 |
| Col iDBM | −0.001 |
| Col iDBM + Ascb | 0.001 |
| Co iDBM + Ascb + BGP | 0.001 |
| Col DBM | 0.341 |
| Col DBM + Ascb | 0.741 |
| Col DBM + Ascb + BGP | 0.903 |

Alkaline phosphatase activity in cells exposed to untreated or inactivated DBM was virtually undetectable. DBM that had been treated with collagenase caused an increase of at least 800-900-fold in alkaline phosphatase activity relative to the effect caused by inactivated collagenase-treated DBM. The fold increase in alkaline phosphatase activity resulting from exposure to collagenase-treated DBM relative to that resulting from (i) exposure to standard DBM or (ii) exposure to collagenase alone or (iii) exposure to tissue culture medium alone was even greater. Since alkaline phosphatase activity in these three control groups of cells was undetectably low, the actual upper bound for the fold increase was probably greater than 900. The increase was approximately 200-450-fold as great as that achieved by exposure of cells to 10% FBS.

Figure 5A:
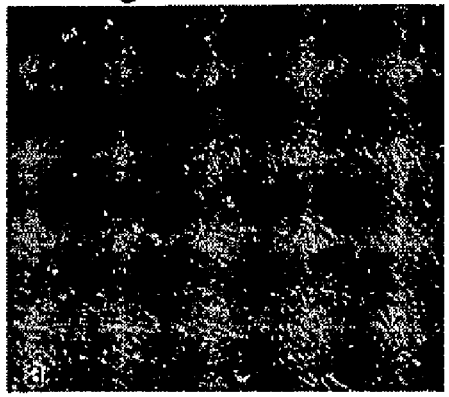
FIG. 5 shows phase contrast photomicrographs of C2C12 cells treated with a) 10% fetal bovine serum (untreated control), b) 100 mg collagenase treated inactivated human DBM, c) 100 mg collagenase-treated human DBM. All cells were cultured for 6 days in DMEM containing 10% FBS. Collagenase-treated human DBM and collagenase-treated inactivated DBM were added to 24-well plates using 8 um transwell inserts. Note the rounded morphology of the cells in FIG. 5c as compared with those in FIGS. 5a and 5b.
Figure 5B:
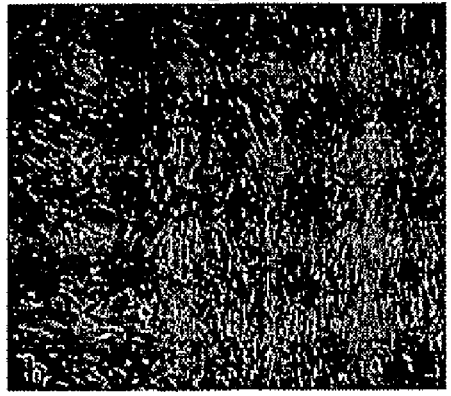
Figure 5C:
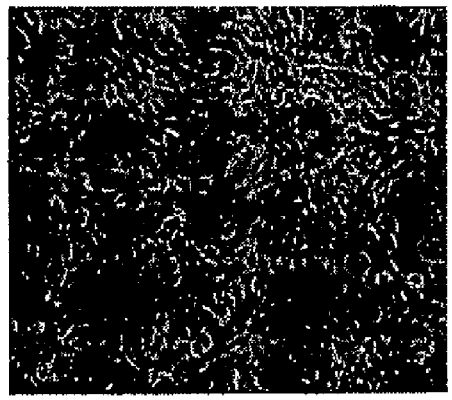

Gross changes in cell phenotype were also observed. Cells treated with collagenase digested human DBM became round and failed to form myotubes. Changes in cell shape can be seen in FIG. 5. Note the rounded morphology of the cells in FIG. 5c, which were treated with DBM that had been exposed to collagenase, relative to the morphology of the cells in FIGS. 4a and 4b, which were treated with either unmodified DBM (a) or collagenase-treated inactivated DBM (b) and exhibit a more elongated appearance.

Alkaline phosphatase activity can be visualized using a variety of substrates, including p-nitrophenyl phosphate. Here, it is reported as amount of p-nitrophenol phosphate converted to p-nitrophenol per minute at 37° C. In FIG. 3 and FIG. 4 alkaline phosphatase activity is normalized to total protein content, i.e., the data represents specific alkaline phosphatase activity. Typically alkaline phosphatase activity is normalized relative to cell number, total protein content, or DNA content. In some cases where standardized cell culture techniques are utilized, alkaline phosphatase activity may be reported per well, per dish, or per volume of cell lysate. Results that are not normalized are considered to be less reliable. Preferably alkaline phosphatase activity should be compared with that in untreated controls, as in these experiments.

Figure 6:
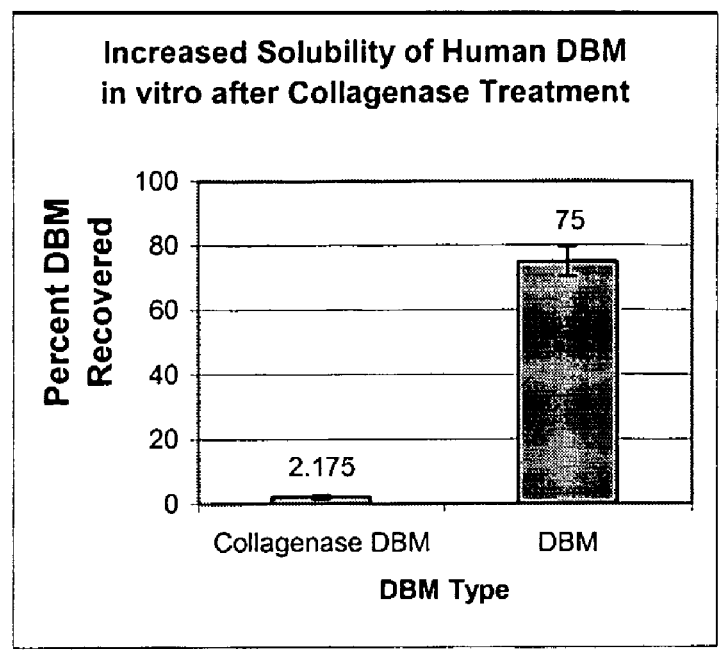
FIG. 6 is a bar graph that shows DBM residue recovered from cell culture inserts after 6 days of tissue culture.

The enhanced activity appears to be correlated with improved solubility of DBM in tissue culture. We found that the solubility of human DBM in tissue culture is markedly enhanced after treatment with collagenase. As seen in FIG. 6, after 6 days of culture collagenase-treated DBM exhibits approximately 34 fold greater solubility than standard DBM preparations. Because the DBM preparations were placed in tissue culture inserts, it is evident that direct cellular contact was not required for solubilization of DBM. The increased solubility of DBM may be a consequence of alterations in the structure resulting from the original collagenase treatment or may be due at least in part to residual collagenase activity that remains after acid treatment and neutralization.

Figure 7A:
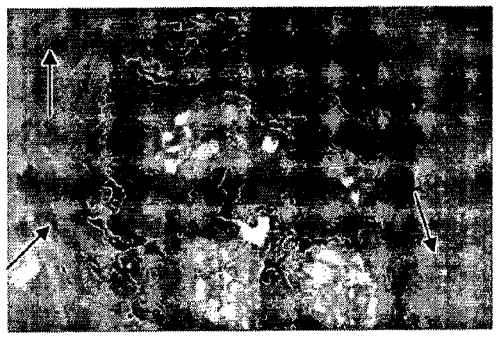
FIG. 7 shows Toluidine Blue stained histology sections of heterotopic nodules that resulted following implantation of human BMG (A) or human DBM (B) into rat muscle. 40 mg of human DBM or 40 mg of human BMG was implanted in the quadriceps muscle of 6 week old female Harlan athymic rats (mu/mu). 28 days after surgery the nodules were recovered, and histological sections were prepared and stained with Toluidine Blue to allow visualization of residual bone matrix (indicated by arrows), along with new osteoid, bone marrow, and cartilage.
Figure 7B:
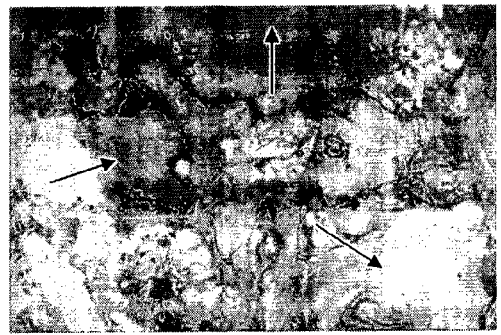

We evaluated the properties of human bone matrix gelatin prepared according to a method similar to that reported for preparation of rat bone matrix gelatin (Nogami and Urist. Transmembrane Bone Matrix Gelatin-Induced Differentiation of Bone. Calcif. Tiss. Res. 1975 19, 153-163; Urist M R, Iwata H, Ceccotti P L, Dorfman R L, Boyd S D, McDowell R M, Chien C. Bone morphogenesis in implants of insoluble bone gelatin. Proc Natl Acad Sci USA. 1973 December; 70(12):3511-5.). Human BMG did not exhibit the ability to induce significant alkaline phosphatase expression in C2C12 cells. Additionally, empirical observation did not lead us to believe that human BMG had significantly greater solubility in tissue culture media, e.g., as compared with standard human DBM. We compared the effects of implanting human BMG or human DBM into rat muscle. As shown in FIG. 7, while human BMG is capable of inducing heterotopic bone formation in athymic rats, significant amounts of insoluble residual matrix can be seen 28 days after implantation of either human BMG or human DBM into rat muscle. Without wishing to be bound by any theory, the increased solubility of collagenase-treated human DBM may result in a desirably reduced amount of residual DBM following implantation into a subject.

Example 11

Enhancement of DBM Activity by Treatment with Multiple Proteases

DBM is prepared as described in Example 10. Following collagenase treatment the DBM is washed to remove residual collagenase. The DBM is then exposed to one of a variety of proteases. Without wishing to be bound by any theory, the proteases may cleave a specific protein (e.g., BMP-2, BMP-4, etc.) to release active peptides or protein fragments having osteoinductive, osteogenic, and/or chondrogenic activity, thereby increasing the osteoinductive, osteogenic, and/or chondrogenic activity. A variety of different treatment conditions (e.g., concentrations, digestion buffers, and treatment durations) may be used. Exemplary proteases and conditions are provided in the Table below.

| Enzyme | Concentration | Digestion Buffer | Treatment Duration |
| --- | --- | --- | --- |
| BMP-1 | 1 pg/ml-100 ug/ml | 25 mM HEPES, 0.01% BRIJ 35 5 mM $CaCl_2$, pH 7.5 | 30 minutes-72 hours |
| Pepsin | 1 ng/ml-100 ug/ml | 20 mM sodium acetate, pH 4.5 | 30 minutes-72 hours |
| Trypsin | 1 ng/ml-100 ug/ml | 50 mM Tris-HCl 20 mM $CaCl_2$ pH 8.0 | 30 minutes-72 hours |

-continued

| Enzyme | Concentration | Digestion Buffer | Treatment Duration |
|---|---|---|---|
| Papain | 1 ng/ml-100 ug/ml | 5 mM L-cysteine, 100 mM Na$_2$HPO$_4$, 5 mM EDTA, pH 7.5 | 30 minutes-72 hours |
| Cathepsin C | 1 ng/ml-100 ug/ml | 100 mM sodium phosphate buffer, pH 6.0, 1.3 mM EDTA, 25 mM cysteine•HCl | 30 minutes-72 hours |
| Cathepsin K | 1 ng/ml-100 ug/ml | 100 mM sodium acetate, (pH 5.5) 20 mM L-cysteine, and 5 mM EDTA | 30 minutes-72 hours |
| Furin | 1 pg/ml-100 ug/ml | 100 mM HEPES (pH 7.5) 0.5% Triton X-100, 1 mM CaCl$_2$, with or without 1 mM 2-mercaptoethanol | 30 minutes-72 hours |

Other Embodiments

The foregoing has been a description of certain non-limiting preferred embodiments of the invention. Those of ordinary skill in the art will appreciate that various changes and modifications to this description may be made without departing from the spirit or scope of the present invention, as defined in the following claims.

We claim:

1. A modified bone matrix comprising a bone matrix that has been exposed to collagenase to produce a modified bono matrix, wherein the level of at least one biological activity of the modified bone matrix is increased relative to its level in an unmodified control bone matrix, and wherein the at least one biological activity is selected from the group consisting of osteoinductive activity, osteogenic activity, and chondrogenic activity.

2. The modified bone matrix of claim 1, wherein the biological activity is osteoinductive activity.

3. The modified bone matrix of claim 1, wherein the biological activity is osteogenic activity.

4. The modified bone matrix of claim 3, wherein a digestion is performed at about 37 degrees Celsius.

5. The modified bone matrix of claim 1, wherein the biological activity is chondrogenic activity.

6. The modified bone matrix of claim 1, wherein the bone matrix is demineralized bone matrix derived at least in part from human bone.

7. The modified bone matrix of claim 1, wherein the bone matrix comprises mineralized bone matrix, partially demineralized bone matrix, demineralized bone matrix, deorganified bone matrix, anorganic matrix, or a mixture thereof.

8. The modified bone matrix of claim 1, wherein the bone matrix comprises a mineralized, partially demineralized, demineralized, deorganified, or anorganic bone section.

9. The modified bone matrix of claim 1, wherein undifferentiated mesenchymal cells treated with the modified bone matrix display increased expression of a marker indicative of osteoblastic or chondrocytic differentiation relative to cells treated with the unmodified control bone matrix.

10. The modified bone matrix of claim 9, wherein the marker is alkaline phosphatase.

11. The modified bone matrix of claim 9, wherein expression of the marker is within a factor of 2 relative to that induced by treating the undifferentiated cells with BMP-2.

12. The modified bone matrix of claim 9, wherein expression of the marker is increased by a factor of approximately 200-450 relative to expression induced by treating the undifferentiated cells with 10% fetal bovine serum.

13. The modified bone matrix of claim 9, wherein expression of the marker is increased by a factor of between approximately 20-900 relative to expression induced by treating the undifferentiated cells with an inactivated bone matrix.

14. The modified bone matrix of claim 1, wherein solubility of the modified bone matrix is greater than solubility of the unmodified bone matrix.

15. The modified bone matrix of claim 1, wherein one or more integrin binding sites is modified relative to an integrin binding site in a control bone matrix.

16. The modified bone matrix of claim 1, wherein the modified bone matrix has osteoinductive activity in an animal species in which the unmodified bone matrix is not osteoinductive.

17. The modified bone matrix of claim 16, wherein the species is selected from the group consisting of: dog, squirrel monkey, and human.

18. The modified bone matrix of claim 1, further comprising one or more bioactive agents selected from the group consisting of: small molecules, chemical compounds, cells, polynucleotides, proteins, protein fragments, peptides, drugs, viruses, antibiotics, anti-neoplastic agents, growth factors, hematopoietic factors, hormones, wound healing factors, and nutrients.

19. The modified bone matrix of claim 1 further comprising an agent selected from the group consisting of: carriers, stabilizing agents, diffusion barrier agents, and water reducing agents.

20. A device for bone repair comprising the modified bone matrix of claim 1, optionally including one or more additional components, formed into a device having a shape suitable for implantation into a subject.

21. A method of treating a subject comprising the step of: implanting the modified bone matrix of claim 1 into a subject at a site of a bone or cartilage defect.

22. A method of preparing a cell composition for implantation into a subject comprising steps of:
obtaining a cell from a subject;
culturing the cell in vitro;
contacting the cell with the modified bone matrix of claim 1.

* * * * *